(12) United States Patent
Yang et al.

(10) Patent No.: US 10,563,222 B2
(45) Date of Patent: Feb. 18, 2020

(54) PROMOTERS FOR HIGH LEVEL EXPRESSION

(71) Applicant: AGENCY FOR SCIENCE, TECHNOLOGY AND RESEARCH, Singapore (SG)

(72) Inventors: Yuansheng Yang, Singapore (SG); Cheng Leong Steven Ho, Singapore (SG); Shiyi Goh Fang, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 15/319,730

(22) PCT Filed: Jun. 17, 2015

(86) PCT No.: PCT/SG2015/050166
§ 371 (c)(1),
(2) Date: Dec. 16, 2016

(87) PCT Pub. No.: WO2015/195049
PCT Pub. Date: Dec. 23, 2015

(65) Prior Publication Data
US 2017/0130244 A1    May 11, 2017

(30) Foreign Application Priority Data

Jun. 18, 2014 (SG) ............................ 10201403371T

(51) Int. Cl.
C12N 15/85    (2006.01)
(52) U.S. Cl.
CPC .......... *C12N 15/85* (2013.01); *C12N 2830/15* (2013.01); *C12N 2830/42* (2013.01); *C12N 2830/60* (2013.01)

(58) Field of Classification Search
None
See application file for complete search history.

(56) References Cited

U.S. PATENT DOCUMENTS

| | | | |
|---|---|---|---|
| 7,537,768 B2 * | 5/2009 | Luke | A61K 39/145 424/186.1 |
| 8,377,653 B2 * | 2/2013 | Silla | C07K 14/005 435/320.1 |
| 9,114,108 B2 * | 8/2015 | Bublot | A61K 39/12 |
| 2003/0232414 A1 | 12/2003 | Moore | |
| 2008/0160048 A1 * | 7/2008 | Fuller | C07K 14/005 424/275.1 |
| 2010/0216188 A1 * | 8/2010 | Hui | C12N 15/85 435/69.1 |

FOREIGN PATENT DOCUMENTS

| | | |
|---|---|---|
| WO | WO 2009/048197 A1 | 4/2009 |
| WO | WO 2010/072676 A1 | 7/2010 |
| WO | WO 2012/074277 A2 | 6/2012 |
| WO | WO 2014/133468 A1 | 9/2014 |
| WO | WO 2014/134657 A1 | 9/2014 |

OTHER PUBLICATIONS

PCT Notification of Transmittal of the International Search Report and the Written Opinion of the International Searching Authority, or the Declaration for PCT Counterpart Application No. PCT/SG2015/050166, 18 pp., (Sep. 7, 2015).
Michael S. Neuberger, et al., "The intron requirement for immunoglobulin gene expression is dependent upon the promoter", Nucleic Acids Research, vol. 16, No. 14, pp. 6713-6724, (1988).
Ahmed Amine Khamlichi, et al., "The effect of intron sequences on expression levels of Ig cDNAs", Gene, vol. 150, No. 2, pp. 387-390, (1994).
Mariati, et al., "Evaluating post-transcriptional regulatory elements for enhancing transient gene expression levels in CHO K1 and HEK293 cells", Protein Expression and Purification, vol. 69, No. 1, pp. 9-15, (2010).
Mariati, et al., "Evaluating regulatory elements of human cytomegalovirus major immediate early gene for enhancing transgene expression levels in CHO K1 and HEK293 cells", Journal of Biotechnology, vol. 147, Nos. 3-4, pp. 160-163, (2010).
Stephen F. Altschul, et al., "Basic Local Alignment Search Tool", Journal of Molecular Biology, vol. 215, pp. 403-410, (1990).
PCT Notification Concerning Transmittal of International Preliminary Report on Patentability for PCT Application No. PCT/SG2015/0501666, 12 pgs. (dated Dec. 29, 2016).
Promega Corporation, "pCI-neo Mammalian Expression Vector: Instructions for Use of Product E1841", Technical Bulletin, Sep. 2009, 1-12.
Mariati et al., "Evaluating post-transcriptional regulatory elements for enhancing transient gene expression levels in CHO K1 and HEK293 cells", Protein Expression and Purification, vol. 69 Aug. 27, 2009, pp. 9-15.

* cited by examiner

Primary Examiner — Nancy J Leith
(74) Attorney, Agent, or Firm — Womble Bond Dickinson (US) LLP

(57) ABSTRACT

The present invention provides for functional chimeric gene regulatory units capable of driving strong and sustained heterologous gene expression.

12 Claims, 2 Drawing Sheets
Specification includes a Sequence Listing.

(A)

(B)

A

B

SEQUENCE LISTING

<160> NUMBER OF SEQ ID NOS: 76

<210> SEQ ID NO 1
<211> LENGTH: 377
<212> TYPE: DNA
<213> ORGANISM: Human cytomegalovirus

<400> SEQUENCE: 1

| | | | | | | |
|---|---|---|---|---|---|---|
| tgacattgat | tattgagtag | ttattaatag | taatcaatta | cggggtcatt | agttcatagc | 60 |
| ccatatatgg | agttccgcgt | tacataactt | acggtaaatg | gcccgcctgg | ctgaccgccc | 120 |
| aacgacccc  | gcccattgac | gtcaataatg | acgtatgttc | ccatagtaac | gccaataggg | 180 |
| actttccatt | gacgtcaatg | ggtggagtat | ttacggtaaa | ctgcccactt | ggcagtacat | 240 |
| caagtgtatc | atatgccaag | tacgccccct | attgacgtca | atgacggtaa | atggcccgcc | 300 |
| tggcattatg | cccagtacat | gaccttatgg | gactttccta | cttggcagta | catctacgta | 360 |
| ttagtcatcg | ctattac | | | | | 377 |

<210> SEQ ID NO 2
<211> LENGTH: 422
<212> TYPE: DNA
<213> ORGANISM: Mouse cytomegalovirus 1

<400> SEQUENCE: 2

| | | | | | | |
|---|---|---|---|---|---|---|
| agtcaatggg | aaaaacccat | tggagccaag | tacactgact | caatagggac | tttccattgg | 60 |
| gttttgccca | gtacataagg | tcataggggt | gtgagtcaac | aggaaagtcc | cattggagcc | 120 |
| aagtacattg | agtcaatagg | actttccaa  | tgggttttgc | ccagtacata | aggtcaatgg | 180 |
| gaggtaagcc | aatgggtttt | tcccattact | ggcacgtata | ctgagtcatt | agggactttc | 240 |
| caatgggttt | tgcccagtac | ataaggtcaa | tagggggtgaa | tcaacaggaa | agtcccattg | 300 |
| gagccaagta | cactgagtca | atagggactt | tccattgggt | tttgcccagt | acaaaaggtc | 360 |
| aatagggggt | gagtcaatgg | gttttccca  | ttattggcac | gtacataagg | tcaatagggg | 420 |
| tg | | | | | | 422 |

<210> SEQ ID NO 3
<211> LENGTH: 168
<212> TYPE: DNA
<213> ORGANISM: Simian virus 40

<400> SEQUENCE: 3

| | | | | | | |
|---|---|---|---|---|---|---|
| tgtggaatgt | gtgtcagtta | gggtgtggaa | agtccccagg | ctccccagca | ggcagaagta | 60 |
| tgcaaagcat | gcatctcaat | tagtcagcaa | ccaggtgtgg | aaagtcccca | ggctccccag | 120 |
| caggcagaag | tatgcaaagc | atgcatctca | attagtcagc | aaccatag | | 168 |

<210> SEQ ID NO 4
<211> LENGTH: 222
<212> TYPE: DNA
<213> ORGANISM: Human cytomegalovirus

<400> SEQUENCE: 4

| | | | | | | |
|---|---|---|---|---|---|---|
| catggtgatg | cggttttggc | agtacatcaa | tgggcgtgga | tagcggtttg | actcacgggg | 60 |
| atttccaagt | ctccacccca | ttgacgtcaa | tgggagtttg | ttttggcacc | aaaatcaacg | 120 |
| ggactttcca | aaatgtcgta | acaactccgc | cccattgacg | caaatgggcg | gtaggcgtgt | 180 |
| acggtgggag | gtctatataa | gcagagctcg | tttagtgaac | cg | | 222 |

<210> SEQ ID NO 5
<211> LENGTH: 285
<212> TYPE: DNA
<213> ORGANISM: Mouse cytomegalovirus 1

<400> SEQUENCE: 5

```
agtcattggg tttttccagc caatttaatt aaaacgccat gtactttccc accattgacg      60
tcaatgggct attgaaacta atgcaacgtg acctttaaac ggtactttcc catagctgat     120
taatgggaaa gtaccgttct cgagccaata cacgtcaatg ggaagtgaaa gggcagccaa     180
aacgtaacac cgccccggtt ttccctggaa attccatatt ggcacgcatt ctattggctg     240
agctgcgttc acgtgggtat aagaggcgcg accagcgtcg gtacc                     285
```

<210> SEQ ID NO 6
<211> LENGTH: 109
<212> TYPE: DNA
<213> ORGANISM: Simian virus 40

<400> SEQUENCE: 6

```
tcccgcccct aactccgccc atcccgcccc taactccgcc cagttccgcc cattctccgc      60
cccatggctg actaattttt tttatttatg cagaggccga ggccgcctc                 109
```

<210> SEQ ID NO 7
<211> LENGTH: 203
<212> TYPE: DNA
<213> ORGANISM: Homo sapiens

<400> SEQUENCE: 7

```
cgtgaggctc cggtgcccgt cagtgggcag agcgcacatc gcccacagtc cccgagaagt      60
tggggggagg ggtcggcaat tgaaccggtg cctagagaag gtggcgcggg gtaaactggg     120
aaagtgatgt cgtgtactgg ctccgccttt tcccgaggg tgggggagaa ccgtatataa      180
gtgcagtagt cgccgtgaac gtt                                              203
```

<210> SEQ ID NO 8
<211> LENGTH: 276
<212> TYPE: DNA
<213> ORGANISM: Gallus gallus

<400> SEQUENCE: 8

```
tcgaggtgag ccccacgttc tgcttcactc tccccatctc ccccccctcc cacccccaa       60 ttttgtattt atttattttt taattatttt gtgcagcgat ggggcgggg ggggggggg      120 cgcgcgccag gcggggcggg gcggggcgag gggcggggcg gggcgaggcg gagaggtgcg     180
gcggcagcca atcagagcgg cgcgctccga aagtttcctt ttatggcgag cggcggcgg     240 cggcggccct ataaaaagcg aagcgcgcgg cgggcg                               276
```

<210> SEQ ID NO 9
<211> LENGTH: 955
<212> TYPE: DNA
<213> ORGANISM: Human cytomegalovirus

<400> SEQUENCE: 9

```
tcagatcgcc tggagacgcc atccacgctg ttttgacctc catagaagac accgggaccg      60
atccagcctc cgcggccggg aacggtgcat tggaacgcgg attccccgtg ccaagagtga     120
cgtaagtacc gcctatagac tctataggca caccccttg gctcttatgc atgctatact      180
gtttttggct tggggcctat acaccccgc ttccttatgc tataggtgat ggtatagctt      240
```

| | |
|---|---:|
| agcctatagg tgtgggttat tgaccattat tgaccactcc cctattggtg acgatacttt | 300 |
| ccattactaa tccataacat ggctctttgc cacaactatc tctattggct atatgccaat | 360 |
| actctgtcct tcagagactg acacggactc tgtattttta caggatgggg tcccatttat | 420 |
| tatttacaaa ttcacatata caacaacgcc gtcccccgtg cccgcagttt ttattaaaca | 480 |
| tagcgtggga tctccacgcg aatctcgggt acgtgttccg gacatgggct cttctccggt | 540 |
| agcggcggag cttccacatc cgagccctgg tcccatgcct ccagcggctc atggtcgctc | 600 |
| ggcagctcct tgctcctaac agtggaggcc agacttaggc acagcacaat gcccaccacc | 660 |
| accagtgtgc cgcacaaggc cgtggcggta gggtatgtgt ctgaaaatga gcgtggagat | 720 |
| tgggctcgca cggctgacgc agatggaaga cttaaggcag cggcagaaga agatgcaggc | 780 |
| agctgagttg ttgtattctg ataagagtca gaggtaactc ccgttgcggt gctgttaacg | 840 |
| gtggagggca gtgtagtctg agcagtactc gttgctgccg cgcgcgccac cagacataat | 900 |
| agctgacaga ctaacagact gttcctttcc atgggtcttt tctgcagtca ccgtc | 955 |

<210> SEQ ID NO 10
<211> LENGTH: 985
<212> TYPE: DNA
<213> ORGANISM: Homo sapiens

<400> SEQUENCE: 10

| | |
|---|---:|
| cttttctcgca acgggtttgc cgccagaaca caggtaagtg ccgtgtgtgg ttcccgcggg | 60 |
| cctggcctct ttacgggtta tggcccttgc gtgccttgaa ttacttccac gcccctggct | 120 |
| gcagtacgtg attcttgatc ccgagcttcg ggttggaagt gggtgggaga gttcgaggcc | 180 |
| ttgcgcttaa ggagccccctt cgcctcgtgc ttgagttgag gcctggcctg ggcgctgggg | 240 |
| ccgccgcgtg cgaatctggt ggcaccttcg cgcctgtctc gctgctttcg ataagtctct | 300 |
| agccatttaa aattttgat gacctgctgc gacgcttttt ttctggcaag atagtcttgt | 360 |
| aaatgcgggc caagatctgc acactggtat ttcgtttttt ggggccgcgg gcggcgacgg | 420 |
| ggcccgtgcg tcccagcgca catgttcggc gaggcgggc ctgcgagcgc ggccaccgag | 480 |
| aatcggacgg gggtagtctc aagctggccg gcctgctctg gtgcctggcc tcgcgccgcc | 540 |
| gtgtatcgcc ccgccctggg cggcaaggct ggcccggtcg gcaccagttg cgtgagcgga | 600 |
| aagatggccg cttccggcc ctgctgcagg gagctcaaaa tggaggacgc ggcgctcggg | 660 |
| agagcgggcg ggtgagtcac ccacacaaag gaaaagggcc tttccgtcct cagccgtcgc | 720 |
| ttcatgtgac tccacggagt accgggcgcc gtccaggcac ctcgattagt tctcgagctt | 780 |
| ttggagtacg tcgtctttag gttgggggga ggggtttat gcgatggagt ttccccacac | 840 |
| tgagtgggtg gagactgaag ttaggccagc ttggcacttg atgtaattct ccttggaatt | 900 |
| tgccctttt gagtttggat cttggttcat tctcaagcct cagacagtgg ttcaaagttt | 960 |
| ttttcttcca tttcaggtgt cgtga | 985 |

<210> SEQ ID NO 11
<211> LENGTH: 999
<212> TYPE: DNA
<213> ORGANISM: Gallus gallus

<400> SEQUENCE: 11

| | |
|---|---:|
| ggagtcgctg cgttgccttc gccccgtgcc ccgctccgcg ccgcctcgcg ccgcccgccc | 60 |
| cggctctgac tgaccgcgtt actcccacag gtgagcgggc gggacggccc ttctcctccg | 120 |
| ggctgtaatt agcgcttggt ttaatgacgg ctcgtttctt ttctgtggct gcgtgaaagc | 180 |

```
cttaaagggc tccgggaggg cccttttgtgc ggggggagc ggctcgggg gtgcgtgcgt      240 gtgtgtgtgc gtggggagcg ccgcgtgcgg cccgcgctgc ccggcggctg tgagcgctgc      300
gggcgcggcg cggggctttg tgcgctccgc gtgtgcgcga ggggagcgcg gccggggggcg     360 gtgccccgcg gtgcgggggg gctgcgaggg gaacaaaggc tgcgtgcggg gtgtgtgcgt      420 ggggggggtga gcaggggggtg tgggcgcggc ggtcgggctg taaccccccc ctgcaccccc    480
ctccccgagt tgctgagcac ggcccggctt cgggtgcggg gctccgtgcg gggcgtggcg      540
cggggctcgc cgtgccgggc ggggggtggc ggcaggtggg ggtgccgggc ggggcggggc      600
cgcctcgggc cggggagggc tcgggggagg ggcgcggcgg ccccggagcg ccggcggctg      660
tcgaggcgcg gcgagccgca gccattgcct tttatggtaa tcgtgcgaga gggcgcaggg      720
acttcctttg tcccaaatct ggcggagccg aaatctggga ggcgccgccg caccccctct      780
agcgggcgcg ggcgaagcgg tgcggcgccg gcaggaagga aatgggcggg gagggccttc      840
gtgcgtcgcc gcgccgccgt cccttctcc atctccagcc tcggggctgc cgcagggggga    900 cggctgcctt cgggggggac ggggcagggc ggggttcggc ttctggcgtg tgaccggcgg      960
ggtttatatc ttcccttctc tgttcctccg cagccagcc                            999

<210> SEQ ID NO 12
<211> LENGTH: 620
<212> TYPE: DNA
<213> ORGANISM: Artificial Sequence
<220> FEATURE:
<223> OTHER INFORMATION: gene regulatory unit

<400> SEQUENCE: 12
acgcgttgac attgattatt gagtagttat taatagtaat caattacggg gtcattagtt       60
catagcccat atatggagtt ccgcgttaca taacttacgg taaatggccc gcctggctga     120
ccgcccaacg acccccgccc attgacgtca ataatgacgt atgttcccat agtaacgcca     180
atagggactt tccattgacg tcaatgggtg agtatttac ggtaaactgc ccacttggca      240
gtacatcaag tgtatcatat gccaagtacg ccccctattg acgtcaatga cggtaaatgg     300
cccgcctggc attatgccca gtacatgacc ttatgggact ttcctacttg gcagtacatc     360
tacgtattag tcatcgctat taccatggtg atgcggtttt ggcagtacat caatgggcgt     420
ggatagcggt ttgactcacg gggatttcca agtctccacc ccattgacgt caatgggagt     480
ttgttttggc accaaaatca acgggacttt ccaaaatgtc gtaacaactc cgccccattg     540
acgcaaatgg gcggtaggcg tgtacggtgg gaggtctata taagcagagc tcgtttagtg     600
aaccggcggc cgcaggatcc                                                 620

<210> SEQ ID NO 13
<211> LENGTH: 728
<212> TYPE: DNA
<213> ORGANISM: Artificial Sequence
<220> FEATURE:
<223> OTHER INFORMATION: gene regulatory unit

<400> SEQUENCE: 13
acgcgtagtc aatgggaaaa acccattgga gccaagtaca ctgactcaat agggactttc       60
cattgggttt tgcccagtac ataaggtcaa taggggtga gtcaacagga aagtcccatt      120
ggagccaagt acattgagtc aatagggact ttccaatggg ttttgcccag tacataaggt     180
caatgggagg taagccaatg ggttttttccc attactggca cgtatactga gtcattaggg    240
```

```
actttccaat gggttttgcc cagtacataa ggtcaatagg ggtgaatcaa caggaaagtc      300
ccattggagc caagtacact gagtcaatag ggactttcca ttgggttttg cccagtacaa      360
aaggtcaata gggggtgagt caatgggttt tcccattat tggcacgtac ataaggtcaa       420
taggggtgag tcattgggtt tttccagcca atttaattaa aacgccatgt actttcccac      480
cattgacgtc aatgggctat tgaaactaat gcaacgtgac ctttaaacgg tacttttcca     540
tagctgatta atgggaaagt accgttctcg agcaatacaa cgtcaatggg aagtgaaagg     600
gcagccaaaa cgtaacaccg ccccggtttt ccctggaaat tccatattgg cacgcattct     660
attggctgag ctgcgttcac gtgggtataa gaggcgcgac cagcgtcggt accgcggccg     720
caggatcc                                                               728

<210> SEQ ID NO 14
<211> LENGTH: 298
<212> TYPE: DNA
<213> ORGANISM: Artificial Sequence
<220> FEATURE:
<223> OTHER INFORMATION: gene regulatory unit

<400> SEQUENCE: 14
acgcgttgtg gaatgtgtgt cagttagggt gtggaaagtc cccaggctcc ccagcaggca      60
gaagtatgca aagcatgcat ctcaattagt cagcaaccag gtgtggaaag tccccaggct     120
ccccagcagg cagaagtatg caaagcatgc atctcaatta gtcagcaacc atagtcccgc     180
ccctaactcc gcccatcccg cccctaactc cgcccagttc cgcccattct ccgccccatg     240
gctgactaat ttttttatt tatgcagagg ccgaggccgc ctcgcggccg caggatcc       298

<210> SEQ ID NO 15
<211> LENGTH: 1200
<212> TYPE: DNA
<213> ORGANISM: Artificial Sequence
<220> FEATURE:
<223> OTHER INFORMATION: gene regulatory unit

<400> SEQUENCE: 15
acgcgtcgtg aggctccggt gcccgtcagt gggcagagcg cacatcgccc acagtccccg      60
agaagttggg gggaggggtc ggcaattgaa ccggtgccta gagaaggtgg cgcggggtaa     120
actgggaaag tgatgtcgtg tactggctcc gccttttttcc cgagggtggg ggagaaccgt     180
atataagtgc agtagtcgcc gtgaacgttc tttttcgcaa cgggtttgcc gccagaacac     240
aggtaagtgc cgtgtgtggt tcccgcgggc ctggcctctt tacgggttat ggcccttgcg     300
tgccttgaat tacttccacg ccctggctg cagtacgtga ttcttgatcc cgagcttcgg     360
gttggaagtg ggtgggagag ttcgaggcct tgcgcttaag gagccccttc gcctcgtgct     420
tgagttgagg cctggcctgg gcgctggggc cgccgcgtgc gaatctggtg gcaccttcgc     480
gcctgtctcg ctgctttcga taagtctcta gccatttaaa atttttgatg acctgctgcg     540 acgcttttt tctggcaaga tagtcttgta aatgcgggcc aagatctgca cactggtatt      600 tcggttttg gggccgcggg cggcgacggg gccgtgcgt cccagcgcac atgttcggcg       660
aggcggggcc tgcgagcgcg gccaccgaga atcggacggg ggtagtctca agctggccgg     720
cctgctctgg tgcctggcct cgcgccgccg tgtatcgccc cgccctgggc ggcaaggctg     780
gcccggtcgg caccagttgc gtgagcggaa agatggccgc ttcccggccc tgctgcaggg     840
agctcaaaat ggaggacgcg cgcgctcggga gagcgggcgg gtgagtcacc cacacaaagg    900
aaaagggcct ttccgtcctc agccgtcgct tcatgtgact ccacggagta ccgggcgccg     960
```

```
tccaggcacc tcgattagtt ctcgagcttt tggagtacgt cgtctttagg ttggggggag    1020
gggttttatg cgatggagtt tccccacact gagtgggtgg agactgaagt taggccagct    1080
tggcacttga tgtaattctc cttggaattt gcccttttg agtttggatc ttggttcatt    1140
ctcaagcctc agacagtggt tcaaagtttt tttcttccat ttcaggtgtc gtgaggatcc    1200

<210> SEQ ID NO 16
<211> LENGTH: 1293
<212> TYPE: DNA
<213> ORGANISM: Artificial Sequence
<220> FEATURE:
<223> OTHER INFORMATION: gene regulatory unit

<400> SEQUENCE: 16
acgcgtacta gttcgaggtg agccccacgt tctgcttcac tctccccatc tcccccccct     60
ccccaccccc aatttgtat ttatttattt tttaattatt ttgtgcagcg atggggcgg     120 gggggggggg ggcgcgcgcc aggcggggcg gggcggggcg aggggcgggg cggggcgagg    180
cggagaggtg cggcggcagc caatcagagc ggcgcgctcc gaaagtttcc ttttatggcg    240
aggcggcggc ggcggcggcc ctataaaaag cgaagcgcgc ggcgggcggg agtcgctgcg    300
ttgccttcgc cccgtgcccc gctccgcgcc gcctcgcgcc gcccgccccg gctctgactg    360
accgcgttac tcccacaggt gagcgggcgg gacggccctt ctcctccggg ctgtaattag    420
cgcttggttt aatgacggct cgtttctttt ctgtggctgc gtgaaagcct taaagggctc    480
cgggagggcc ctttgtgcgg gggggagcgg ctcgggggt gcgtgcgtgt gtgtgtgcgt    540
ggggagcgcc gcgtgcggcc cgcgctgccc ggcggctgtg agcgctgcgg gcgcggcgcg    600
gggctttgtg cgctccgcgt gtgcgcgagg ggagcgcggc cggggcggt gccccgcggt    660 gcgggggggc tgcgagggga acaaaggctg cgtgcgggt gtgtgcgtgg ggggtgagc    720 aggggtgtg ggcgcggcgg tcgggctgta acccccccct gcaccccct ccccgagttg    780 ctgagcacgg cccggcttcg ggtgcgggc tccgtgcggg gcgtggcgcg gggctcgccg    840
tgccgggcgg ggggtggcgg caggtggggg tgccgggcgg ggcggggccg cctcgggccg    900
gggagggctc gggggagggg cgcggcggcc ccggagcgcc ggcggctgtc gaggcgcggc    960
gagccgcagc cattgccttt tatggtaatc gtgcgagagg gcgcagggac ttcctttgtc   1020
ccaaatctgg cggagccgaa atctggggagg cgccgccgca ccccctctag cgggcgcggg   1080
cgaagcggtg cggcgccggc aggaaggaaa tgggcgggga gggccttcgt gcgtcgccgc   1140
gccgccgtcc ccttctccat ctccagcctc ggggctgccg cagggggacg gctgccttcg   1200 gggggacgg ggcagggcgg ggttcggctt ctggcgtgtg accggcgggg tttatatctt   1260
cccttctctg ttcctccgca gccagccgga tcc                                 1293

<210> SEQ ID NO 17
<211> LENGTH: 683
<212> TYPE: DNA
<213> ORGANISM: Artificial Sequence
<220> FEATURE:
<223> OTHER INFORMATION: chimeric gene regulatory unit

<400> SEQUENCE: 17
acgcgttgac attgattatt gagtagttat taatagtaat caattacggg gtcattagtt     60
catagcccat atatggagtt ccgcgttaca taacttacgg taaatggccc gcctggctga    120
ccgcccaacg acccccgccc attgacgtca ataatgacgt atgttcccat agtaacgcca    180
```

```
atagggactt tccattgacg tcaatgggtg gagtatttac ggtaaactgc ccacttggca    240
gtacatcaag tgtatcatat gccaagtccg cccctattg acgtcaatga cggtaaatgg    300
cccgcctggc attatgccca gtacatgacc ttacgggact ttcctacttg gcagtacatc    360
tacgtattag tcatcgctat tacagtcatt gggttttcc agccaattta attaaaacgc    420
catgtacttt cccaccattg acgtcaatgg gctattgaaa ctaatgcaac gtgacccttta   480 aacggtactt tcccatagct gattaatggg aaagtaccgt tctcgagcca atacacgtca    540
atgggaagtg aaagggcagc caaaacgtaa caccgccccg ttttccctg gaaattccat     600 attggcacgc attctattgg ctgagctgcg ttcacgtggg tataagaggc gcgaccagcg    660
tcggtaccgc ggccgcagga tcc                                           683

<210> SEQ ID NO 18
<211> LENGTH: 507
<212> TYPE: DNA
<213> ORGANISM: Artificial Sequence
<220> FEATURE:
<223> OTHER INFORMATION: chimeric gene regulatory unit

<400> SEQUENCE: 18
acgcgttgac attgattatt gactagttat taatagtaat caattacggg gtcattagtt     60
catagcccat atatggagtt ccgcgttaca taacttacgg taaatggccc gcctggctga    120
ccgcccaacg accccgccc attgacgtca ataatgacgt atgttcccat agtaacgcca    180
atagggactt tccattgacg tcaatgggtg gagtatttac ggtaaactgc ccacttggca    240
gtacatcaag tgtatcatat gccaagtacg cccctattg acgtcaatga cggtaaatgg    300
cccgcctggc attatgccca gtacatgacc ttatgggact ttcctacttg gcagtacatc    360
tacgtattag tcatcgctat tactcccgcc cctaactccg cccatcccgc cctaactcc     420 gcccagttcc gcccattctc cgccccatgg ctgactaatt ttttttattt atgcagaggc    480
cgaggccgcc tcgcggccgc aggatcc                                       507

<210> SEQ ID NO 19
<211> LENGTH: 607
<212> TYPE: DNA
<213> ORGANISM: Artificial Sequence
<220> FEATURE:
<223> OTHER INFORMATION: chimeric gene regulatory unit

<400> SEQUENCE: 19
acgcgttgac attgattatt gactagttat taatagtaat caattacggg gtcattagtt     60
catagcccat atatggagtt ccgcgttaca taacttacgg taaatggccc gcctggctga    120
ccgcccaacg accccgccc attgacgtca ataatgacgt atgttcccat agtaacgcca    180
atagggactt tccattgacg tcaatgggtg gagtatttac ggtaaactgc ccacttggca    240
gtacatcaag tgtatcatat gccaagtacg cccctattg acgtcaatga cggtaaatgg    300
cccgcctggc attatgccca gtacatgacc ttatgggact ttcctacttg gcagtacatc    360
tacgtattag tcatcgctat tacactagtc gtgaggctcc ggtgcccgtc agtgggcaga    420
gcgcacatcg cccacagtcc ccgagaagtt gggggaggg tcggcaatt gaaccggtgc     480 ctagagaagg tggcgcgggg taaactggga aagtgatgtc gtgtactggc tccgcctttt    540
tcccgagggt gggggagaac cgtatataag tgcagtagtc gccgtgaacg ttgcggccgc    600
aggatcc                                                             607
```

<210> SEQ ID NO 20
<211> LENGTH: 677
<212> TYPE: DNA
<213> ORGANISM: Artificial Sequence
<220> FEATURE:
<223> OTHER INFORMATION: chimeric gene regulatory unit

<400> SEQUENCE: 20

```
acgcgttgac attgattatt gactagttat taatagtaat caattacggg gtcattagtt      60
catagcccat atatggagtt ccgcgttaca taacttacgg taaatggccc gcctggctga     120
ccgcccaacg accccgccc attgacgtca ataatgacgt atgttcccat agtaacgcca      180
atagggactt tccattgacg tcaatgggtg gagtatttac ggtaaactgc ccacttggca     240
gtacatcaag tgtatcatat gccaagtacg cccctattg acgtcaatga cggtaaatgg      300
cccgcctggc attatgccca gtacatgacc ttatgggact ttcctacttg gcagtacatc     360
tacgtattag tcatcgctat tacactagtt cgaggtgagc cccacgttct gcttcactct     420
ccccatctcc cccccctccc cacccccaat tttgtattta tttattttt aattattttg      480
tgcagcgatg ggggcggggg gggggggggc gcgcgccagg cggggcgggg cggggcgagg     540
ggcggggcgg ggcgaggcgg agaggtgcgg cggcagccaa tcagagcggc gcgctccgaa     600
agtttccttt tatggcgagg cggcggcggc ggcggcccta taaaaagcga agcgcgcggc     660
gggcggccgc aggatcc                                                    677
```

<210> SEQ ID NO 21
<211> LENGTH: 671
<212> TYPE: DNA
<213> ORGANISM: Artificial Sequence
<220> FEATURE:
<223> OTHER INFORMATION: chimeric gene regulatory unit

<400> SEQUENCE: 21

```
acgcgtagtc aatgggaaaa acccattgga gccaagtaca ctgactcaat agggactttc      60
cattgggttt tgcccagtac ataaggtcaa taggggtga gtcaacagga aagtcccatt      120
ggagccaagt acattgagtc aatagggact ttccaatggg ttttgcccag tacataaggt     180
caatgggagg taagccaatg ggttttccc attactggca cgtatactga gtcattaggg      240
actttccaat gggttttgcc cagtacataa ggtcaatagg ggtgaatcaa caggaaagtc     300
ccattggagc caagtacact gagtcaatag ggactttcca ttgggttttg cccagtacaa     360
aaggtcaata gggggtgagt caatgggttt ttcccattat tggcacgtac ataaggtcaa     420
taggggtgac tagtcatggt gatgcggttt tggcagtaca ccaatgggcg tggatagcgg     480
tttgactcac ggggatttcc aagtctccac cccattgacg tcaatgggag tttgttttgg     540
caccaaaatc aacgggactt tccaaaatgt cgtaataacc ccgccccgtt gacgcaaatg     600
ggcggtaggc gtgtacggtg ggaggtctat ataagcagag ctcgtttagt gaaccggcgg     660
ccgcaggatc c                                                          671
```

<210> SEQ ID NO 22
<211> LENGTH: 558
<212> TYPE: DNA
<213> ORGANISM: Artificial Sequence
<220> FEATURE:
<223> OTHER INFORMATION: chimeric gene regulatory unit

<400> SEQUENCE: 22

```
acgcgtagtc aatgggaaaa acccattgga gccaagtaca ctgactcaat agggactttc      60
```

```
cattgggttt tgcccagtac ataaggtcaa tagggggtga gtcaacagga aagtcccatt    120
ggagccaagt acattgagtc aatagggact ttccaatggg ttttgcccag tacataaggt    180
caatgggagg taagccaatg ggttttccc attactggca cgtatactga gtcattaggg     240
actttccaat gggttttgcc cagtacataa ggtcaatagg ggtgaatcaa caggaaagtc    300
ccattggagc caagtacact gagtcaatag ggactttcca ttgggttttg cccagtacaa    360
aaggtcaata gggggtgagt caatgggttt ttcccattat tggcacgtac ataaggtcaa    420 tagggggtgac tagttcccgc ccctaactcc gcccatcccg ccctaactc cgcccagttc    480 cgcccattct ccgccccatg gctgactaat ttttttttatt tatgcagagg ccgaggccgc    540
ctcgcggccg caggatcc                                                   558

<210> SEQ ID NO 23
<211> LENGTH: 652
<212> TYPE: DNA
<213> ORGANISM: Artificial Sequence
<220> FEATURE:
<223> OTHER INFORMATION: chimeric gene regulatory unit

<400> SEQUENCE: 23
acgcgtagtc aatgggaaaa acccattgga gccaagtaca ctgactcaat agggactttc    60
cattgggttt tgcccagtac ataaggtcaa tagggggtga gtcaacagga aagtcccatt    120
ggagccaagt acattgagtc aatagggact ttccaatggg ttttgcccag tacataaggt    180
caatgggagg taagccaatg ggttttccc attactggca cgtatactga gtcattaggg     240
actttccaat gggttttgcc cagtacataa ggtcaatagg ggtgaatcaa caggaaagtc    300
ccattggagc caagtacact gagtcaatag ggactttcca ttgggttttg cccagtacaa    360
aaggtcaata gggggtgagt caatgggttt ttcccattat tggcacgtac ataaggtcaa    420 tagggggtgac tagtcgtgag gctccggtgc ccgtcagtgg gcagagcgca catcgcccac    480
agtccccgag aagttggggg gagggggtcgg caattgaacc ggtgcctaga gaaggtggcg    540
cggggtaaac tgggaaagtg atgtcgtgta ctggctccgc cttttttccccg agggtggggg    600 agaaccgtat ataagtgcag tagtcgccgt gaacgttgcg gccgcaggat cc             652

<210> SEQ ID NO 24
<211> LENGTH: 722
<212> TYPE: DNA
<213> ORGANISM: Artificial Sequence
<220> FEATURE:
<223> OTHER INFORMATION: chimeric gene regulatory unit

<400> SEQUENCE: 24
acgcgtagtc aatgggaaaa acccattgga gccaagtaca ctgactcaat agggactttc    60
cattgggttt tgcccagtac ataaggtcaa tagggggtga gtcaacagga aagtcccatt    120
ggagccaagt acattgagtc aatagggact ttccaatggg ttttgcccag tacataaggt    180
caatgggagg taagccaatg ggttttccc attactggca cgtatactga gtcattaggg     240
actttccaat gggttttgcc cagtacataa ggtcaatagg ggtgaatcaa caggaaagtc    300
ccattggagc caagtacact gagtcaatag ggactttcca ttgggttttg cccagtacaa    360
aaggtcaata gggggtgagt caatgggttt ttcccattat tggcacgtac ataaggtcaa    420 tagggggtgac tagttcgagg tgagcccac gttctgcttc actctcccca tctcccccc     480 ctccccaccc ccaattttgt atttattttat ttttttaatta ttttgtgcag cgatgggggc    540 ggggggggggg gggcgcgcg ccaggcgggg cggggcgggg cgaggggcgg ggcggggcga    600
```

```
ggcggagagg tgcggcggca gccaatcaga gcggcgcgct ccgaaagttt cctttatgg      660 cgaggcggcg gcggcggcgg ccctataaaa agcgaagcgc gcggcgggcg gccgcaggat      720
cc                                                                     722
```

<210> SEQ ID NO 25
<211> LENGTH: 418
<212> TYPE: DNA
<213> ORGANISM: Artificial Sequence
<220> FEATURE:
<223> OTHER INFORMATION: chimeric gene regulatory unit

<400> SEQUENCE: 25

```
acgcgttgtg gaatgtgtgt cagttagggt gtggaaagtc cccaggctcc ccagcaggca       60
gaagtatgca aagcatgcat ctcaattagt cagcaaccag gtgtggaaag tccccaggct      120
ccccagcagg cagaagtatg caaagcatgc atctcaatta gtcagcaacc atagactagt      180
catggtgatg cggttttggc agtacaccaa tgggcgtgga tagcggtttg actcacgggg      240
atttccaagt ctccaccca ttgacgtcaa tgggagtttg ttttggcacc aaaatcaacg       300
ggactttcca aatgtcgta ataacccgc ccgttgacg caaatgggcg gtaggcgtgt         360
acggtgggag gtctatataa gcagagctcg tttagtgaac cgtgcggccg caggatcc        418
```

<210> SEQ ID NO 26
<211> LENGTH: 480
<212> TYPE: DNA
<213> ORGANISM: Artificial Sequence
<220> FEATURE:
<223> OTHER INFORMATION: chimeric gene regulatory unit

<400> SEQUENCE: 26

```
acgcgttgtg gaatgtgtgt cagttagggt gtggaaagtc cccaggctcc ccagcaggca       60
gaagtatgca aagcatgcat ctcaattagt cagcaaccag gtgtggaaag tccccaggct      120
ccccagcagg cagaagtatg caaagcatgc atctcaatta gtcagcaacc atagactagt      180
agtcattggg ttttccagc caatttaatt aaaacgccat gtactttccc accattgacg       240
tcaatgggct attgaaacta atgcaacgtg acctttaaac ggtactttcc catagctgat      300
taatgggaaa gtaccgttct cgagccaata cacgtcaatg ggaagtgaaa gggcagccaa     360
aacgtaacac cgccccggtt ttccctggaa attccatatt ggcacgcatt ctattggctg     420
agctgcgttc acgtgggtat aagaggcgcg accagcgtcg gtaccgcggc cgcaggatcc     480
```

<210> SEQ ID NO 27
<211> LENGTH: 398
<212> TYPE: DNA
<213> ORGANISM: Artificial Sequence
<220> FEATURE:
<223> OTHER INFORMATION: chimeric gene regulatory unit

<400> SEQUENCE: 27

```
acgcgttgtg gaatgtgtgt cagttagggt gtggaaagtc cccaggctcc ccagcaggca       60
gaagtatgca aagcatgcat ctcaattagt cagcaaccag gtgtggaaag tccccaggct      120
ccccagcagg cagaagtatg caaagcatgc atctcaatta gtcagcaacc atagactagt      180
cgtgaggctc cggtgcccgt cagtgggcag agcgcacatc gcccacagtc cccgagaagt      240 tgggggagg ggtcggcaat tgaaccggtg cctagagaag gtggcgcggg gtaaactggg       300
aaagtgatgt cgtgtactgg ctccgccttt tcccgagggg tgggggagaa ccgtatataa      360
```

```
gtgcagtagt cgccgtgaac gttgcggccg caggatcc                              398
```

<210> SEQ ID NO 28
<211> LENGTH: 471
<212> TYPE: DNA
<213> ORGANISM: Artificial Sequence
<220> FEATURE:
<223> OTHER INFORMATION: chimeric gene regulatory unit

<400> SEQUENCE: 28

```
acgcgttgtg gaatgtgtgt cagttagggt gtggaaagtc cccaggctcc ccagcaggca      60
gaagtatgca aagcatgcat ctcaattagt cagcaaccag gtgtggaaag tccccaggct     120
ccccagcagg cagaagtatg caaagcatgc atctcaatta gtcagcaacc atagactagt     180
tcgaggtgag ccccacgttc tgcttcactc tccccatctc ccccccctcc ccaccccaa      240
ttttgtattt atttattttt taattatttt gtgcagcgat ggggggcgggg ggggggggg     300
cgcgcgccag gcggggcggg gcggggcgag gggcggggcg gggcgaggcg gagaggtgcg     360
gcggcagcca atcagagcgg cgcgctccga aagtttcctt ttatggcgag gcggcggcgg     420
cggcggccct ataaaagcg aagcgcgcgg cgggcggcgg ccgcaggatc c                471
```

<210> SEQ ID NO 29
<211> LENGTH: 1566
<212> TYPE: DNA
<213> ORGANISM: Artificial Sequence
<220> FEATURE:
<223> OTHER INFORMATION: chimeric gene regulatory unit

<400> SEQUENCE: 29

```
acgcgttgac attgattatt gactagttat taatagtaat caattacggg gtcattagtt      60
catagcccat atatggagtt ccgcgttaca taacttacgg taaatggccc gcctggctga     120
ccgcccaacg acccccgccc attgacgtca ataatgacgt atgttcccat agtaacgcca     180
atagggactt tccattgacg tcaatgggtg gagtatttac ggtaaactgc ccacttggca     240
gtacatcaag tgtatcatat gccaagtccg cccctattg acgtcaatga cggtaaatgg     300
cccgcctggc attatgccca gtacatgacc ttacgggact tcctacttg gcagtacatc     360
tacgtattag tcatcgctat taccatggtg atgcggtttt ggcagtacac caatgggcgt     420
ggatagcggt ttgactcacg gggatttcca agtctccacc ccattgacgt caatgggagt     480
ttgttttggc accaaaatca acgggacttt ccaaaatgtc gtaataaccc cgccccgttg     540
acgcaaatgg gcggtaggcg tgtacggtgg aggtctata taagcagagc tgtttagtg      600
aaccgtcaga tcgcctggag acgccatcca cgctgtttg acctccatag aagacaccgg     660
gaccgatcca gcctccgcgg ccgggaacgg tgcattggaa cgcggattcc ccgtgccaag     720
agtgacgtaa gtaccgccta tagactctat aggcacaccc ctttggctct tatgcatgct     780
atactgtttt tggcttgggg cctatacacc cccgcttcct tatgctatag gtgatggtat     840
agcttagcct ataggtgtgg gttattgacc attattgacc actccctat ggtgacgat       900
actttccatt actaatccat aacatggctc tttgccacaa ctatctctat tggctatatg     960
ccaatactct gtccttcaga gactgacacg gactctgtat ttttacagga tggggtccca    1020
tttattattt acaaattcac atatacaaca acgccgtccc cgtgcccgc agtttttatt     1080
aaacatagcg tgggatctcc acgcgaatct cgggtacgtg ttccggacat gggctcttct    1140
ccggtagcgc ggagcttcc acatccgagc cctggtccca tgcctccagc ggctcatggt    1200
cgctcggcag ctccttgctc ctaacagtgg aggccagact taggcacagc acaatgccca    1260
```

```
ccaccaccag tgtgccgcac aaggccgtgg cggtagggta tgtgtctgaa aatgagcgtg   1320
gagattgggc tcgcacggct gacgcagatg gaagacttaa ggcagcggca gaagaagatg   1380
caggcagctg agttgttgta ttctgataag agtcagaggt aactcccgtt gcggtgctgt   1440
taacggtgga gggcagtgta gtctgagcag tactcgttgc tgccgcgcgc gccaccagac   1500
ataatagctg acagactaac agactgttcc tttccatggg tctttctgc  agtcaccgtc   1560 ggatcc                                                              1566
```

<210> SEQ ID NO 30
<211> LENGTH: 1636
<212> TYPE: DNA
<213> ORGANISM: Artificial Sequence
<220> FEATURE:
<223> OTHER INFORMATION: chimeric gene regulatory unit

<400> SEQUENCE: 30

```
acgcgttgac attgattatt gactagttat aatagtaat  caattacggg gtcattagtt     60
catagcccat atatggagtt ccgcgttaca aacttacgg  taaatggccc gcctggctga   120
ccgcccaacg accccgccc  attgacgtca ataatgacgt atgttcccat agtaacgcca   180
atagggactt tccattgacg tcaatgggtg gagtattac  ggtaaactgc ccacttggca   240
gtacatcaag tgtatcatat gccaagtacg ccccctattg acgtcaatga cggtaaatgg   300
cccgcctggc attatgccca gtacatgacc ttatgggact ttcctacttg gcagtacatc   360
tacgtattag tcatcgctat tacagtcatt gggttttcc  agccaattta attaaaacgc   420
catgtacttt cccaccattg acgtcaatgg gctattgaaa ctaatgcaac gtgacccttta  480 aacggtactt tcccatagct gattaatggg aaagtaccgt tctcgagcca atacacgtca   540
atgggaagtg aaagggcagc caaaacgtaa caccgccccg ttttccctg  gaaattccat   600 attggcacgc attctattgg ctgagctgcg ttcacgtggg tataagaggc gcgaccagcg   660
tcggtaccgg cggccgctca gatcgcctgg agacgccatc cacgctgttt tgacctccat   720
agaagacacc gggaccgatc cagcctccgc ggccgggaac ggtgcattgg aacgcggatt   780
ccccgtgcca agagtgacgt aagtaccgcc tatagactct ataggcacac ccctttggct   840
cttatgcatg ctatactgtt tttggcttgg ggcctataca ccccgctcc  ttatgctata    900 ggtgatggta tagcttagcc tataggtgtg ggttattgac cattattgac cactccccta   960
ttggtgacga tactttccat tactaatcca taacatggct ctttgccaca actatctcta  1020
ttggctatat gccaatactc tgtccttcag agactgacac ggactctgta ttttacagg  1080 atggggtccc atttattatt tacaaattca catatacaac aacgccgtcc ccgtgcccg   1140 cagtttttat taaacatagc gtgggatctc cacgcgaatc tcgggtacgt gttccggaca  1200
tgggctcttc tccggtagcg gcggagcttc cacatccgag ccctggtccc atgcctccag  1260
cggctcatgg tcgctcggca gctccttgct cctaacagtg gaggccagac ttaggcacag  1320
cacaatgccc accaccacca gtgtgccgca caaggccgtg gcggtagggt atgtgtctga  1380
aaatgagctc ggagattggg ctcgcaccgt gacgcagatg gaagacttaa ggcagcggca  1440
gaagaagatg caggcagctg agttgttgta ttctgataag agtcagaggt aactcccgtt  1500
gcggtgctgt taacggtgga gggcagtgta gtctgagcag tactcgttgc tgccgcgcgc  1560
gccaccagac ataatagctg acagactaac agactgttcc tttccatggg tctttctgc   1620 agtcaccgtc ggatcc                                                  1636
```

<210> SEQ ID NO 31
<211> LENGTH: 1459
<212> TYPE: DNA
<213> ORGANISM: Artificial Sequence
<220> FEATURE:
<223> OTHER INFORMATION: chimeric gene regulatory unit

<400> SEQUENCE: 31

```
acgcgttgac attgattatt gactagttat taatagtaat caattacggg gtcattagtt      60
catagcccat atatggagtt ccgcgttaca taacttacgg taaatggccc gcctggctga     120
ccgcccaacg accccccgcc cattgacgtca ataatgacgt atgttcccat agtaacgcca    180
atagggactt tccattgacg tcaatgggtg gagtatttac ggtaaactgc ccacttggca    240
gtacatcaag tgtatcatat gccaagtacg cccccattg acgtcaatga cggtaaatgg     300
cccgcctggc attatgccca gtacatgacc ttatgggact ttcctacttg gcagtacatc    360
tacgtattag tcatcgctat tactcccgcc cctaactccg cccatcccgc cctaactcc     420
gcccagttcc gcccattctc cgccccatgg ctgactaatt ttttttattt atgcagaggc    480
cgaggccgcc tcgcggccgc tcagatcgcc tggagacgcc atccacgctg ttttgacctc    540
catagaagac accgggaccg atccagcctc cgcggccggg aacggtgcat tggaacgcgg    600
attccccgtg ccaagagtga cgtaagtacc gcctatagac tctataggca cacccctttg    660
gctcttatgc atgctatact gtttttggct tgggcctat acaccccgc tccttatgct     720
ataggtgatg gtatagctta gcctataggt gtgggttatt gaccattatt gaccactccc    780
ctattggtga cgatactttc cattactaat ccataacatg gctctttgcc acaactatct    840
ctattggcta tatgccaata ctctgtcctt cagagactga cacggactct gtattttac    900
aggatggggt cccatttatt atttacaaat tcacatatac aacaacgccg tccccgtgc    960
ccgcagtttt tattaaacat agcgtgggat ctccacgcga atctcgggta cgtgttccgg   1020
acatgggctc ttctccggta gcggcggagc ttccacatcc gagccctggt cccatgcctc   1080
cagcggctca tggtcgctcg gcagctcctt gctcctaaca gtggaggcca gacttaggca   1140
cagcacaatg cccaccacca ccagtgtgcc gcacaaggcc gtggcggtag gtatgtgtc    1200
tgaaaatgag ctcggagatt gggctcgcac cgtgacgcag atggaagact taaggcagcg   1260
gcagaagaag atgcaggcag ctgagttgtt gtattctgat aagagtcaga ggtaactccc   1320
gttgcggtgc tgttaacggt ggagggcagt gtagtctgag cagtactcgt tgctgccgcg   1380
cgcgccacca gacataatag ctgacagact aacagactgt tcctttccat gggtcttttc   1440
tgcagtcacc gtcggatcc                                                1459
```

<210> SEQ ID NO 32
<211> LENGTH: 1559
<212> TYPE: DNA
<213> ORGANISM: Artificial Sequence
<220> FEATURE:
<223> OTHER INFORMATION: chimeric gene regulatory unit

<400> SEQUENCE: 32

```
acgcgttgac attgattatt gactagttat taatagtaat caattacggg gtcattagtt      60
catagcccat atatggagtt ccgcgttaca taacttacgg taaatggccc gcctggctga    120
ccgcccaacg accccccgcc cattgacgtca ataatgacgt atgttcccat agtaacgcca   180
atagggactt tccattgacg tcaatgggtg gagtatttac ggtaaactgc ccacttggca    240
gtacatcaag tgtatcatat gccaagtacg cccccattg acgtcaatga cggtaaatgg     300
```

```
cccgcctggc attatgccca gtacatgacc ttatgggact ttcctacttg gcagtacatc      360
tacgtattag tcatcgctat tacactagtc gtgaggctcc ggtgcccgtc agtgggcaga      420
gcgcacatcg cccacagtcc ccgagaagtt ggggggaggg gtcggcaatt gaaccggtgc      480
ctagagaagg tggcgcgggg taaactggga aagtgatgtc gtgtactggc tccgcctttt      540
tcccgagggt gggggagaac cgtatataag tgcagtagtc gccgtgaacg ttgcggccgc      600
tcagatcgcc tggagacgcc atccacgctg ttttgacctc catagaagac accgggaccg      660
atccagcctc cgcggccggg aacggtgcat tggaacgcgg attccccgtg ccaagagtga      720
cgtaagtacc gcctatagac tctataggca caccccttt g gctcttatgc atgctatact      780 gttttt ggct tggggcctat acaccccgc tccttatgct ataggtgatg gtatagctta      840
gcctataggt gtgggttatt gaccattatt gaccactccc ctattggtga cgatactttc      900
cattactaat ccataacatg gctctttgcc acaactatct ctattggcta tatgccaata      960
ctctgtcctt cagagactga cacggactct gtattt ttac aggatggggt cccatttatt     1020
atttacaaat tcacatatac aacaacgccg tcccccgtgc ccgcagtttt tattaaacat      1080
agcgtgggat ctccacgcga atctcgggta cgtgttccgg acatgggctc ttctccggta      1140
gcggcggagc ttccacatcc gagccctggt cccatgcctc cagcggctca tggtcgctcg      1200
gcagctcctt gctcctaaca gtggaggcca gacttaggca cagcacaatg cccaccacca      1260
ccagtgtgcc gcacaaggcc gtggcggtag gtatgtgtc tgaaaatgag ctcggagatt      1320
gggctcgcac cgtgacgcag atggaagact taaggcagcg gcagaagaag atgcaggcag      1380
ctgagttgtt gtattctgat aagagtcaga ggtaactccc gttgcggtgc tgttaacggt      1440
ggagggcagt gtagtctgag cagtactcgt tgctgccgcg cgcgccacca gacataatag      1500
ctgacagact aacagactgt tcctttccat gggtcttttc tgcagtcacc gtcggatcc      1559
```

<210> SEQ ID NO 33
<211> LENGTH: 1630
<212> TYPE: DNA
<213> ORGANISM: Artificial Sequence
<220> FEATURE:
<223> OTHER INFORMATION: chimeric gene regulatory unit

<400> SEQUENCE: 33

```
acgcgttgac attgattatt gactagttat taatagtaat caattacggg gtcattagtt       60
catagcccat atatggagtt ccgcgttaca taacttacgg taaatggccc gcctggctga      120
ccgcccaacg acccccgccc attgacgtca ataatgacgt atgttcccat agtaacgcca      180
atagggactt tccattgacg tcaatgggtg gagtatttac ggtaaactgc ccacttggca      240
gtacatcaag tgtatcatat gccaagtacg ccccctattg acgtcaatga cggtaaatgg      300
cccgcctggc attatgccca gtacatgacc ttatgggact ttcctacttg gcagtacatc      360
tacgtattag tcatcgctat tacactagtt cgaggtgagc cccacgttct gcttcactct      420
ccccatctcc cccccctccc cacccccaat tttgtattta ttttttttt aattattttg      480 tgcagcgatg ggggcggggg ggggggggggc gcgcgccagg cggggcgggg cgggcgaggg      540
ggcggggcgg ggcgaggcgg agaggtgcgg cggcagccaa tcagagcggc gcgctccgaa      600
agtttccttt tatggcgagg cggcggcggc ggcggcccta taaaaagcga agcgcgcggc      660
gggcggccgc atcagatcgc ctggagacgc catccacgct gttttgacct ccatagaaga      720
caccgggacc gatccagcct ccgcggccgg gaacggtgca ttggaacgcg gattccccgt      780
```

| | |
|---|---|
| gccaagagtg acgtaagtac cgcctataga ctctataggc acaccccttt ggctcttatg | 840 |
| catgctatac tgttttggc ttggggccta tacaccccg ctccttatgc tataggtgat | 900 |
| ggtatagctt agcctatagg tgtgggttat tgaccattat tgaccactcc cctattggtg | 960 |
| acgatacttt ccattactaa tccataacat ggctctttgc cacaactatc tctattggct | 1020 |
| atatgccaat actctgtcct tcagagactg acacggactc tgtattttta caggatgggg | 1080 |
| tcccatttat tatttacaaa ttcacatata caacaacgcc gtccccgtg cccgcagttt | 1140 |
| ttattaaaca tagcgtggga tctccacgcg aatctcgggt acgtgttccg gacatgggct | 1200 |
| cttctccggt agcggcggag cttccacatc cgagccctgg tcccatgcct ccagcggctc | 1260 |
| atggtcgctc ggcagctcct tgctcctaac agtggaggcc agacttaggc acagcacaat | 1320 |
| gcccaccacc accagtgtgc cgcacaaggc cgtggcggta gggtatgtgt ctgaaaatga | 1380 |
| gctcggagat tgggctcgca ccgtgacgca gatggaagac ttaaggcagc ggcagaagaa | 1440 |
| gatgcaggca gctgagttgt tgtattctga taagagtcag aggtaactcc cgttgcggtg | 1500 |
| ctgttaacgg tggagggcag tgtagtctga gcagtactcg ttgctgccgc gcgcgccacc | 1560 |
| agacataata gctgacagac taacagactg ttcctttcca tgggtctttt ctgcagtcac | 1620 |
| cgtcggatcc | 1630 |

<210> SEQ ID NO 34
<211> LENGTH: 1680
<212> TYPE: DNA
<213> ORGANISM: Artificial Sequence
<220> FEATURE:
<223> OTHER INFORMATION: chimeric gene regulatory unit

<400> SEQUENCE: 34

| | |
|---|---|
| acgcgtagtc aatgggaaaa acccattgga gccaagtaca ctgactcaat agggactttc | 60 |
| cattgggttt tgcccagtac ataaggtcaa taggggtga gtcaacagga aagtcccatt | 120 |
| ggagccaagt acattgagtc aataggggact ttccaatggg ttttgcccag tacataaggt | 180 |
| caatgggagg taagccaatg ggttttttccc attactggca cgtatactga gtcattaggg | 240 |
| actttccaat gggttttgcc cagtacataa ggtcaatagg ggtgaatcaa caggaaagtc | 300 |
| ccattggagc caagtacact gagtcaatag ggactttcca ttgggttttg cccagtacaa | 360 |
| aggtcaata gggggtgagt caatgggttt ttcccattat tggcacgtac ataaggtcaa | 420 |
| tagggggtgag tcattgggtt tttccagcca atttaattaa aacgccatgt actttcccac | 480 |
| cattgacgtc aatgggctat tgaaactaat gcaacgtgac cttttaaacgg tacttttccca | 540 |
| tagctgatta atgggaaagt accgttctcg agccaataca cgtcaatggg aagtgaaagg | 600 |
| gcagccaaaa cgtaacaccg ccccggtttt ccctggaaat tccatattgg cacgcattct | 660 |
| attggctgag ctgcgttcac gtgggtataa gaggcgcgac cagcgtcggt accgcggccg | 720 |
| ctcagatcgc ctgagacgc catccacgct gttttgacct ccatagaaga caccgggacc | 780 |
| gatccagcct ccgcggccgg gaacggtgca ttggaacgcg gattccccgt gccaagagtg | 840 |
| acgtaagtac cgcctataga ctctataggc acaccccttt ggctcttatg catgctatac | 900 |
| tgttttggc ttggggccta tacaccccg ctccttatgc tataggtgat ggtatagctt | 960 |
| agcctatagg tgtgggttat tgaccattat tgaccactcc cctattggtg acgatacttt | 1020 |
| ccattactaa tccataacat ggctctttgc cacaactatc tctattggct atatgccaat | 1080 |
| actctgtcct tcagagactg acacggactc tgtattttta caggatgggg tcccatttat | 1140 |
| tatttacaaa ttcacatata caacaacgcc gtccccgtg cccgcagttt ttattaaaca | 1200 |

| | |
|---|---:|
| tagcgtggga tctccacgcg aatctcgggt acgtgttccg gacatgggct cttctccggt | 1260 |
| agcggcggag cttccacatc cgagccctgg tcccatgcct ccagcggctc atggtcgctc | 1320 |
| ggcagctcct tgctcctaac agtggaggcc agacttaggc acagcacaat gcccaccacc | 1380 |
| accagtgtgc cgcacaaggc cgtggcggta gggtatgtgt ctgaaaatga gctcggagat | 1440 |
| tgggctcgca ccgtgacgca gatggaagac ttaaggcagc ggcagaagaa gatgcaggca | 1500 |
| gctgagttgt tgtattctga taagagtcag aggtaactcc cgttgcggtg ctgttaacgg | 1560 |
| tggagggcag tgtagtctga gcagtactcg ttgctgccgc gcgcgccacc agacataata | 1620 |
| gctgacagac taacagactg ttcctttcca tgggtctttt ctgcagtcac cgtcggatcc | 1680 |

<210> SEQ ID NO 35
<211> LENGTH: 1614
<212> TYPE: DNA
<213> ORGANISM: Artificial Sequence
<220> FEATURE:
<223> OTHER INFORMATION: chimeric gene regulatory unit

<400> SEQUENCE: 35

| | |
|---|---:|
| acgcgtagtc aatgggaaaa acccattgga gccaagtaca ctgactcaat agggactttc | 60 |
| cattgggttt tgcccagtac ataaggtcaa taggggtgtga gtcaacagga aagtcccatt | 120 |
| ggagccaagt acattgagtc aatagggact ttccaatggg ttttgcccag tacataaggt | 180 |
| caatgggagg taagccaatg ggttttccc attactggca cgtatactga gtcattaggg | 240 |
| actttccaat gggttttgcc cagtacataa ggtcaatagg ggtgaatcaa caggaaagtc | 300 |
| ccattggagc caagtacact gagtcaatag ggactttcca ttgggttttg cccagtacaa | 360 |
| aaggtcaata gggggtgagt caatgggttt ttcccattat tggcacgtac ataaggtcaa | 420 |
| tagggggtgac tagtcatggt gatgcggttt tggcagtaca ccaatgggcg tggatagcgg | 480 |
| tttgactcac ggggatttcc aagtctccac cccattgacg tcaatgggag tttgttttgg | 540 |
| caccaaaatc aacgggactt tccaaaatgt cgtaataacc ccgccccgtt gacgcaaatg | 600 |
| ggcggtaggc gtgtacggtg ggaggtctat ataagcagag ctcgtttagt gaaccgcaga | 660 |
| tcgcctggag acgccatcca cgctgttttg acctccatag aagacaccgg gaccgatcca | 720 |
| gcctccgcgg ccgggaacgg tgcattggaa cgcggattcc ccgtgccaag agtgacgtaa | 780 |
| gtaccgccta tagactctat aggcacaccc ctttggctct tatgcatgct atactgtttt | 840 |
| tggcttgggg cctatacacc cccgctcctt atgctatagg tgatggtata gcttagccta | 900 |
| taggtgtggg ttattgacca ttattgacca ctcccctatt ggtgacgata ctttccatta | 960 |
| ctaatccata acatggctct ttgccacaac tatctctatt ggctatatgc caatactctg | 1020 |
| tccttcagag actgacacgg actctgtatt tttacaggat ggggtcccat ttattattta | 1080 |
| caaattcaca tatacaacaa cgccgtcccc cgtgcccgca gttttttatta aacatagcgt | 1140 |
| gggatctcca cgcgaatctc gggtacgtgt tccggacatg gctcttctc cggtagcggc | 1200 |
| ggagcttcca catccgagcc ctggtcccat gcctccagcg gctcatggtc gctcggcagc | 1260 |
| tccttgctcc taacagtgga ggccagactt aggcacagca caatgccac caccaccagt | 1320 |
| gtgccgcaca aggccgtggc ggtagggtat gtgtctgaaa atgagctcgg agattgggct | 1380 |
| cgcaccgtga cgcagatgga agacttaagg cagcggcaga agaagatgca ggcagctgag | 1440 |
| ttgttgtatt ctgataagag tcagaggtaa ctcccgttgc ggtgctgtta acggtggagg | 1500 |
| gcagtgtagt ctgagcagta ctcgttgctg ccgcgcgcgc caccagacat aatagctgac | 1560 |

| agactaacag actgttcctt tccatgggtc ttttctgcag tcaccgtcgg atcc | 1614 |

<210> SEQ ID NO 36
<211> LENGTH: 1510
<212> TYPE: DNA
<213> ORGANISM: Artificial Sequence
<220> FEATURE:
<223> OTHER INFORMATION: chimeric gene regulatory unit

<400> SEQUENCE: 36

| acgcgtagtc aatgggaaaa acccattgga gccaagtaca ctgactcaat agggactttc | 60 |
|---|---|
| cattgggttt tgcccagtac ataaggtcaa taggggtga gtcaacagga aagtcccatt | 120 |
| ggagccaagt acattgagtc aatagggact ttccaatggg ttttgcccag tacataaggt | 180 |
| caatgggagg taagccaatg ggttttcccc attactggca cgtatactga gtcattaggg | 240 |
| actttccaat gggttttgcc cagtacataa ggtcaatagg ggtgaatcaa caggaaagtc | 300 |
| ccattggagc caagtacact gagtcaatag ggactttcca ttgggttttg cccagtacaa | 360 |
| aggtcaata gggggtgagt caatgggttt ttcccattat tggcacgtac ataaggtcaa | 420 |
| taggggtgac tagttcccgc ccctaactcc gcccatcccg ccctaactc gcccagttc | 480 |
| cgcccattct ccgccccatg gctgactaat tttttttatt tatgcagagg ccgaggccgc | 540 |
| ctcgcggccg ctcagatcgc ctggagacgc catccacgct gttttgacct ccatagaaga | 600 |
| caccgggacc gatccagcct ccgcggccgg gaacggtgca ttggaacgcg gattccccgt | 660 |
| gccaagagtg acgtaagtac cgcctataga ctctataggc acaccccttt ggctcttatg | 720 |
| catgctatac tgttttttggc ttggggccta tacaccccg ctccttatgc tataggtgat | 780 |
| ggtatagctt agcctatagg tgtgggttat tgaccattat tgaccactcc cctattggtg | 840 |
| acgatacttt ccattactaa tccataacat ggctctttgc cacaactatc tctattggct | 900 |
| atatgccaat actctgtcct tcagagactg acacggactc tgtattttta caggatgggg | 960 |
| tcccatttat tatttacaaa ttcacatata caacaacgcc gtccccgtg cccgcagttt | 1020 |
| ttattaaaca tagcgtggga tctccacgcg aatctcgggt acgtgttccg gacatgggct | 1080 |
| cttctccggt agcggcggag cttccacatc cgagccctgg tcccatgcct ccagcggctc | 1140 |
| atggtcgctc ggcagctcct tgctcctaac agtggaggcc agacttaggc acagcacaat | 1200 |
| gcccaccacc accagtgtgc cgcacaaggc cgtggcggta gggtatgtgt ctgaaaatga | 1260 |
| gctcggagat tgggctcgca ccgtgacgca gatggaagac ttaaggcagc ggcagaagaa | 1320 |
| gatgcaggca gctgagttgt tgtattctga taagagtcag aggtaactcc cgttgcggtg | 1380 |
| ctgttaacgg tggagggcag tgtagtctga gcagtactcg ttgctgccgc gcgcgccacc | 1440 |
| agacataata gctgacagac taacagactg ttcctttcca tgggtctttt ctgcagtcac | 1500 |
| cgtcggatcc | 1510 |

<210> SEQ ID NO 37
<211> LENGTH: 1604
<212> TYPE: DNA
<213> ORGANISM: Artificial Sequence
<220> FEATURE:
<223> OTHER INFORMATION: chimeric gene regulatory unit

<400> SEQUENCE: 37

| acgcgtagtc aatgggaaaa acccattgga gccaagtaca ctgactcaat agggactttc | 60 |
|---|---|
| cattgggttt tgcccagtac ataaggtcaa taggggtga gtcaacagga aagtcccatt | 120 |
| ggagccaagt acattgagtc aatagggact ttccaatggg ttttgcccag tacataaggt | 180 |

```
caatgggagg taagccaatg ggttttccc attactggca cgtatactga gtcattaggg      240
actttccaat gggttttgcc cagtacataa ggtcaatagg ggtgaatcaa caggaaagtc      300
ccattggagc caagtacact gagtcaatag ggactttcca ttgggttttg cccagtacaa      360
aaggtcaata gggggtgagt caatgggttt ttcccattat tggcacgtac ataaggtcaa      420
taggggtgac tagtcgtgag gctccggtgc ccgtcagtgg gcagagcgca catcgcccac      480
agtccccgag aagttggggg gaggggtcgg caattgaacc ggtgcctaga gaaggtggcg      540
cggggtaaac tgggaaagtg atgtcgtgta ctggctccgc cttttccccg agggtggggg      600
agaaccgtat ataagtgcag tagtcgccgt gaacgttgcg gccgctcaga tcgcctggag      660
acgccatcca cgctgttttg acctccatag aagacaccgg gaccgatcca gcctccgcgg      720
ccgggaacgg tgcattggaa cgcggattcc ccgtgccaag agtgacgtaa gtaccgccta      780
tagactctat aggcacaccc ctttggctct tatgcatgct atactgtttt tggcttgggg      840
cctatacacc cccgctcctt atgctatagg tgatggtata gcttagccta taggtgtggg      900
ttattgacca ttattgacca ctcccctatt ggtgacgata ctttccatta ctaatccata      960
acatggctct ttgccacaac tatctctatt ggctatatgc caatactctg tccttcagag     1020
actgacacgg actctgtatt tttacaggat ggggtcccat ttattattta caaattcaca     1080
tatacaacaa cgccgtcccc cgtgcccgca gttttttatta aacatagcgt gggatctcca     1140
cgcgaatctc gggtacgtgt tccggacatg ggctcttctc cggtagcggc ggagcttcca     1200
catccgagcc ctggtccat gcctccagcg gctcatggtc gctcggcagc tccttgctcc      1260
taacagtgga ggccagactt aggcacagca caatgcccac caccaccagt gtgccgcaca     1320
aggccgtggc ggtagggtat gtgtctgaaa atgagctcgg agattgggct cgcaccgtga     1380
cgcagatgga agacttaagg cagcggcaga agaagatgca ggcagctgag ttgttgtatt     1440
ctgataagag tcagaggtaa ctcccgttgc ggtgctgtta acggtggagg gcagtgtagt     1500
ctgagcagta ctcgttgctg ccgcgcgcgc caccagacat aatagctgac agactaacag     1560
actgttcctt tccatgggtc ttttctgcag tcaccgtcgg atcc                      1604
```

<210> SEQ ID NO 38
<211> LENGTH: 1682
<212> TYPE: DNA
<213> ORGANISM: Artificial Sequence
<220> FEATURE:
<223> OTHER INFORMATION: chimeric gene regulatory unit

<400> SEQUENCE: 38

```
acgcgtagtc aatgggaaaa acccattgga gccaagtaca ctgactcaat agggactttc       60
cattgggttt tgcccagtac ataaggtcaa taggggtgat gtcaacagga aagtcccatt      120
ggagccaagt acattgagtc aatagggact ttccaatggg ttttgcccag tacataaggt      180
caatgggagg taagccaatg ggttttccc attactggca cgtatactga gtcattaggg      240
actttccaat gggttttgcc cagtacataa ggtcaatagg ggtgaatcaa caggaaagtc      300
ccattggagc caagtacact gagtcaatag ggactttcca ttgggttttg cccagtacaa      360
aaggtcaata gggggtgagt caatgggttt ttcccattat tggcacgtac ataaggtcaa      420
taggggtgac tagttcgagg tgagccccac gttctgcttc actctcccca tctccccccc      480
ctccccaccc ccaattttgt atttattat ttttaatta ttttgtgcag cgatgggggc        540
gggggggggg ggggcgcgcg ccaggcgggg cggggcgggg cgaggggcgg ggcggggcga      600
```

```
ggcggagagg tgcggcggca gccaatcaga gcggcgcgct ccgaaagttt cctttatgg      660 cgaggcggcg gcggcggcgg ccctataaaa agcgaagcgc gcggcgggcg gccgcgcggc      720
cgctcagatc gcctggagac gccatccacg ctgttttgac ctccatagaa gacaccggga      780
ccgatccagc ctccgcggcc gggaacggtg cattggaacg cggattcccc gtgccaagag      840
tgacgtaagt accgcctata gactctatag gcacacccct ttggctctta tgcatgctat      900 actgttttg  gcttgggccc tatacacccc cgctccttat gctataggtg atggtatagc      960
ttagcctata ggtgtgggtt attgaccatt attgaccact cccctattgg tgacgatact     1020
ttccattact aatccataac atggctcttt gccacaacta tctctattgg ctatatgcca     1080
atactctgtc cttcagagac tgacacggac tctgtatttt tacaggatgg ggtcccattt     1140
attatttaca aattcacata caacaacgcc gtcccccg tgcccgcagt ttttattaaa       1200
catagcgtgg gatctccacg cgaatctcgg gtacgtgttc cggacatggg ctcttctccg     1260
gtagcggcgg agcttccaca tccgagccct ggtcccatgc ctccagcggc tcatggtcgc     1320
tcggcagctc cttgctccta acagtggagg ccagacttag gcacagcaca atgcccacca     1380
ccaccagtgt gccgcacaag gccgtggcgg tagggtatgt gtctgaaaat gagctcggag     1440
attgggctcg caccgtgacg cagatggaag acttaaggca gcggcagaag aagatgcagg     1500
cagctgagtt gttgtattct gataagagtc agaggtaact cccgttgcgg tgctgttaac     1560
ggtggagggc agtgtagtct gagcagtact cgttgctgcc gcgcgcgcca ccagacataa     1620
tagctgacag actaacagac tgttcctttc catgggtctt ttctgcagtc accgtcggat     1680
cc                                                                   1682
```

<210> SEQ ID NO 39
<211> LENGTH: 1250
<212> TYPE: DNA
<213> ORGANISM: Artificial Sequence
<220> FEATURE:
<223> OTHER INFORMATION: chimeric gene regulatory unit

<400> SEQUENCE: 39

```
acgcgttgtg gaatgtgtgt cagttagggt gtggaaagtc cccaggctcc ccagcaggca       60
gaagtatgca aagcatgcat ctcaattagt cagcaaccag gtgtggaaag tccccaggct      120
ccccagcagg cagaagtatg caaagcatgc atctcaatta gtcagcaacc atagtcccgc      180
ccctaactcc gcccatcccg ccctaactc cgcccagttc cgcccattct ccgccccatg      240
gctgactaat ttttttatt tatgcagagg ccgaggccgc ctcgcggccg ctcagatcgc      300
ctggagacgc catccacgct gttttgacct ccatagaaga caccgggacc gatccagcct     360
ccgcggccgg gaacggtgca ttggaacgcg gattccccgt gccaagagtg acgtaagtac     420
cgcctataga ctctataggc acaccccttt ggctcttatg catgctatac tgttttggc     480 ttggggccta tacaccccg ctccttatgc tataggtgat ggtatagctt agcctatagg      540
tgtgggttat tgaccattat tgaccactcc ctattggtg acgatacttt ccattactaa      600
tccataacat ggctctttgc cacaactatc tctattggct atatgccaat actctgtcct     660
tcagagactg acacggactc tgtatttta caggatgggg tcccatttat tatttacaaa     720
ttcacatata caacaacgcc gtcccccgtg cccgcagttt ttattaaaca tagcgtggga     780
tctccacgcg aatctcgggt acgtgttccg gacatgggct cttctccggt agcggcggag     840
cttccacatc cgagccctgg tcccatgcct ccagcggctc atggtcgctc ggcagctcct     900
tgctcctaac agtggaggcc agacttaggc acagcacaat gcccaccacc accagtgtgc     960
```

```
cgcacaaggc cgtggcggta gggtatgtgt ctgaaaatga gctcggagat tgggctcgca    1020
ccgtgacgca gatggaagac ttaaggcagc ggcagaagaa gatgcaggca gctgagttgt    1080
tgtattctga taagagtcag aggtaactcc cgttgcggtg ctgttaacgg tggagggcag    1140
tgtagtctga gcagtactcg ttgctgccgc gcgcgccacc agacataata gctgacagac    1200
taacagactg ttcctttcca tgggtctttt ctgcagtcac cgtcggatcc                1250

<210> SEQ ID NO 40
<211> LENGTH: 1360
<212> TYPE: DNA
<213> ORGANISM: Artificial Sequence
<220> FEATURE:
<223> OTHER INFORMATION: chimeric gene regulatory unit

<400> SEQUENCE: 40
acgcgttgtg gaatgtgtgt cagttagggt gtggaaagtc cccaggctcc ccagcaggca      60
gaagtatgca aagcatgcat ctcaattagt cagcaaccag gtgtggaaag tccccaggct    120
ccccagcagg cagaagtatg caaagcatgc atctcaatta gtcagcaacc atagactagt    180
catggtgatg cggttttggc agtacaccaa tgggcgtgga tagcggtttg actcacgggg    240
atttccaagt ctccacccca ttgacgtcaa tgggagtttg ttttggcacc aaaatcaacg    300
ggactttcca aaatgtcgta taacccccgc cccgttgacg caaatgggcg gtaggcgtgt    360
acggtgggag gtctatataa gcagagctcg tttagtgaac cgcagatcgc ctggagacgc    420
catccacgct gttttgacct ccatagaaga caccgggacc gatccagcct ccgcggccgg    480
gaacggtgca ttggaacgcg gattcccgt gccaagagtg acgtaagtac cgcctataga    540
ctctataggc acacccettt ggctcttatg catgctatac tgttttggc ttggggccta    600 tacaccccg ctccttatgc tataggtgat ggtatagctt agcctatagg tgtgggttat    660
tgaccattat tgaccactcc cctattggtg acgatacttt ccattactaa tccataacat    720
ggctctttgc cacaactatc tctattggct atatgccaat actctgtcct tcagagactg    780
acacggactc tgtattttta caggatgggg tcccatttat tatttacaaa ttcacatata    840
caacaacgcc gtcccccgtg cccgcagttt ttattaaaca tagcgtggga tctccacgcg    900
aatctcgggt acgtgttccg gacatgggct cttctccggt agcggcggag cttccacatc    960
cgagccctgg tccatgcctc cagcggctc atggtcgctc ggcagctcct tgctcctaac   1020
agtggaggcc agacttaggc acagcacaat gcccaccacc accagtgtgc cgcacaaggc   1080
cgtggcggta gggtatgtgt ctgaaaatga gctcggagat tgggctcgca ccgtgacgca   1140
gatggaagac ttaaggcagc ggcagaagaa gatgcaggca gctgagttgt tgtattctga   1200
taagagtcag aggtaactcc cgttgcggtg ctgttaacgg tggagggcag tgtagtctga   1260
gcagtactcg ttgctgccgc gcgcgccacc agacataata gctgacagac taacagactg   1320
ttcctttcca tgggtctttt ctgcagtcac cgtcggatcc                           1360

<210> SEQ ID NO 41
<211> LENGTH: 1432
<212> TYPE: DNA
<213> ORGANISM: Artificial Sequence
<220> FEATURE:
<223> OTHER INFORMATION: chimeric gene regulatory unit

<400> SEQUENCE: 41
acgcgttgtg gaatgtgtgt cagttagggt gtggaaagtc cccaggctcc ccagcaggca      60
```

```
gaagtatgca aagcatgcat ctcaattagt cagcaaccag gtgtggaaag tccccaggct    120 cccccagcagg cagaagtatg caaagcatgc atctcaatta gtcagcaacc atagactagt    180
agtcattggg ttttccagc caatttaatt aaaacgccat gtactttccc accattgacg    240
tcaatgggct attgaaacta atgcaacgtg acctttaaac ggtactttcc catagctgat    300
taatgggaaa gtaccgttct cgagccaata cacgtcaatg ggaagtgaaa gggcagccaa    360
aacgtaacac cgccccggtt ttccctggaa attccatatt ggcacgcatt ctattggctg    420
agctgcgttc acgtgggtat aagaggcgcg accagcgtcg gtaccgcggc cgctcagatc    480
gcctggagac gccatccacg ctgttttgac ctccatagaa gacaccggga ccgatccagc    540
ctccgcggcc gggaacggtg cattggaacg cggattcccc gtgccaagag tgacgtaagt    600
accgcctata gactctatag gcacacccct ttggctctta tgcatgctat actgtttttg    660
gcttggggcc tatacacccc cgctccttat gctataggtg atggtatagc ttagcctata    720
ggtgtgggtt attgaccatt attgaccact cccctattgg tgacgatact ttccattact    780
aatccataac atggctcttt gccacaacta tctctattgg ctatatgcca atactctgtc    840
cttcagagac tgacacggac tctgtatttt tacaggatgg ggtcccattt attatttaca    900
aattcacata tacaacaacg ccgtcccccg tgcccgcagt ttttattaaa catagcgtgg    960
gatctccacg cgaatctcgg gtacgtgttc cggacatggg ctcttctccg gtagcggcgg    1020
agcttccaca tccgagccct ggtcccatgc ctccagcggc tcatggtcgc tcggcagctc    1080
cttgctccta acagtggagg ccagacttag gcacagcaca atgcccacca ccaccagtgt    1140
gccgcacaag gccgtggcgg tagggtatgt gtctgaaaat gagctcggag attgggctcg    1200
caccgtgacg cagatggaag acttaaggca gcggcagaag aagatgcagg cagctgagtt    1260
gttgtattct gataagagtc agaggtaact cccgttgcgg tgctgttaac ggtggagggc    1320
agtgtagtct gagcagtact cgttgctgcc gcgcgcgcca ccagacataa tagctgacag    1380
actaacagac tgttccttc catgggtctt ttctgcagtc accgtcggat cc    1432
```

<210> SEQ ID NO 42
<211> LENGTH: 1350
<212> TYPE: DNA
<213> ORGANISM: Artificial Sequence
<220> FEATURE:
<223> OTHER INFORMATION: chimeric gene regulatory unit

<400> SEQUENCE: 42

```
acgcgttgtg gaatgtgtgt cagttagggt gtggaaagtc cccaggctcc ccagcaggca    60
gaagtatgca aagcatgcat ctcaattagt cagcaaccag gtgtggaaag tccccaggct    120 cccccagcagg cagaagtatg caaagcatgc atctcaatta gtcagcaacc atagactagt    180
cgtgaggctc cggtgcccgt cagtgggcag agcgcacatc gcccacagtc cccgagaagt    240
tggggggagg ggtcggcaat tgaaccggtg cctagagaag gtggcgcggg gtaaactggg    300
aaagtgatgt cgtgtactgg ctccgccttt ttcccgaggg tgggggagaa ccgtatataa    360
gtgcagtagt cgccgtgaac gttgcggccg ctcagatcgc ctggagacgc catccacgct    420
gttttgacct ccatagaaga caccgggacc gatccagcct ccgcggccgg gaacggtgca    480
ttggaacgcg gattccccgt gccaagagtg acgtaagtac cgcctataga ctctataggc    540
acaccccttt ggctcttatg catgctatac tgttttggc ttggggccta tacaccccg    600 ctccttatgc tataggtgat ggtatagctt agcctatagg tgtgggttat tgaccattat    660
tgaccactcc cctattggtg acgatacttt ccattactaa tccataacat ggctctttgc    720
```

```
cacaactatc tctattggct atatgccaat actctgtcct tcagagactg acacggactc    780 tgtatttta  caggatgggg tcccatttat tatttacaaa ttcacatata caacaacgcc    840
gtcccccgtg cccgcagttt ttattaaaca tagcgtggga tctccacgcg aatctcgggt    900
acgtgttccg gacatgggct cttctccggt agcggcggag cttccacatc cgagccctgg    960
tcccatgcct ccagcggctc atggtcgctc ggcagctcct tgctcctaac agtggaggcc   1020
agacttaggc acagcacaat gcccaccacc accagtgtgc cgcacaaggc cgtggcggta   1080
gggtatgtgt ctgaaaatga gctcggagat tgggctcgca ccgtgacgca gatggaagac   1140
ttaaggcagc ggcagaagaa gatgcaggca gctgagttgt tgtattctga taagagtcag   1200
aggtaactcc cgttgcggtg ctgttaacgg tggagggcag tgtagtctga gcagtactcg   1260
ttgctgccgc gcgcgccacc agacataata gctgacagac taacagactg ttcctttcca   1320
tgggtctttt ctgcagtcac cgtcggatcc                                    1350

<210> SEQ ID NO 43
<211> LENGTH: 1423
<212> TYPE: DNA
<213> ORGANISM: Artificial Sequence
<220> FEATURE:
<223> OTHER INFORMATION: chimeric gene regulatory unit

<400> SEQUENCE: 43
acgcgttgtg gaatgtgtgt cagttagggt gtggaaagtc cccaggctcc ccagcaggca     60
gaagtatgca aagcatgcat ctcaattagt cagcaaccag gtgtggaaag tccccaggct    120
ccccagcagg cagaagtatg caaagcatgc atctcaatta gtcagcaacc atagactagt    180
tcgaggtgag ccccacgttc tgcttcactc tcccccatctc ccccccctcc ccaccccaa    240 ttttgtattt atttattttt taattatttt gtgcagcgat gggggcgggg gggggggggg    300
cgcgcgccag gcggggcggg gcggggcgag gggcggggcg gggcgaggcg gagaggtgcg    360
gcggcagcca atcagagcgg cgcgctccga aagtttcctt ttatggcgag gcggcggcgg    420
cggcggccct ataaaaagcg aagcgcgcg  cgggcggcgg ccgctcagat cgcctggaga    480
cgccatccac gctgttttga cctccataga agacaccggg accgatccag cctccgcggc    540
cgggaacggt gcattggaac gcggattccc cgtgccaaga gtgacgtaag taccgcctat    600
agactctata ggcacacccc tttggctctt atgcatgcta tactgttttt ggcttggggc    660
ctatacaccc ccgctcctta tgctataggt gatggtatag cttagcctat aggtgtgggt    720
tattgaccat tattgaccac tcccctattg gtgacgatac tttccattac taatccataa    780
catggctctt tgccacaact atctctattg gctatatgcc aatactctgt ccttcagaga    840
ctgacacgga ctctgtatttt tacaggatg gggtcccatt tattatttac aaattcacat    900
atacaacaac gccgtccccc gtgcccgcag ttttttattaa acatagcgtg gatctccac    960 gcgaatctcg ggtacgtgtt ccggacatgg gctcttctcc ggtagcggcg gagcttccac   1020
atccgagccc tggtcccatg cctccagcgg ctcatggtcg ctcggcagct ccttgctcct   1080
aacagtggag gccagactta ggcacagcac aatgcccacc accaccagtg tgccgcacaa   1140
ggccgtggcg gtagggtatg tgtctgaaaa tgagctcgga gattgggctc gcaccgtgac   1200
gcagatggaa gacttaaggc agcggcagaa gaagatgcag gcagctgagt tgttgtattc   1260
tgataagagt cagaggtaac tcccgttgcg gtgctgttaa cggtggaggg cagtgtagtc   1320
tgagcagtac tcgttgctgc cgcgcgcgcc accagacata atagctgaca gactaacaga   1380
```

```
ctgttcctttt ccatgggtct tttctgcagt caccgtcgga tcc              1423

<210> SEQ ID NO 44
<211> LENGTH: 1604
<212> TYPE: DNA
<213> ORGANISM: Artificial Sequence
<220> FEATURE:
<223> OTHER INFORMATION: chimeric gene regulatory unit

<400> SEQUENCE: 44
acgcgttgac attgattatt gagtagttat taatagtaat caattacggg gtcattagtt   60
catagcccat atatggagtt ccgcgttaca taacttacgg taaatggccc gcctggctga  120
ccgcccaacg accccgccc attgacgtca ataatgacgt atgttcccat agtaacgcca  180
atagggactt tccattgacg tcaatgggtg gagtatttac ggtaaactgc ccacttggca  240
gtacatcaag tgtatcatat gccaagtccg cccctattg acgtcaatga cggtaaatgg  300
cccgcctggc attatgccca gtacatgacc ttacgggact ttcctacttg gcagtacatc  360
tacgtattag tcatcgctat taccatggtg atgcggtttt ggcagtacac caatgggcgt  420
ggatagcggt ttgactcacg gggatttcca agtctccacc ccattgacgt caatgggagt  480
ttgttttggc accaaaatca acgggacttt ccaaaatgtc gtaataaccc cgccccgttg  540
acgcaaatgg gcggtaggcg tgtacggtgg gaggtctata taagcagagc tcgtttagtg  600
aaccggcggc cgccttttc gcaacgggtt tgccgccaga acacaggtaa gtgccgtgtg  660
tggttcccgc gggcctggcc tctttacggg ttatggccct gcgtgccttg aattacttc  720 cacgccctg gctgcagtac gtgattcttg atcccgagct tcgggttgga agtgggtggg  780
agagttcgag gccttgcgct taaggagccc cttcgcctcg tgcttgagtt gaggcctggc  840
ctgggcgctg gggccgccgc gtgcgaatct ggtggcacct tcgcgcctgt ctcgctgctt  900
tcgataagtc tctagccatt taaaattttt gatgacctgc tgcgacgctt ttttttctggc  960 aagatagtct tgtaaatgcg ggccaagatc tgcacactgg tatttcggtt tttgggccg 1020 cgggcggcga cggggcccgt gcgtcccagc gcacatgttc ggcgaggcgg ggcctgcgag 1080
cgcggccacc gagaatcgga cggggtagt ctcaagctgg ccggcctgct ctggtgcctg 1140
gcctcgcgcc gccgtgtatc gccccgccct gggcggcaag gctggccccgg tcggcaccag 1200 ttgcgtgagc ggaaagatgg ccgcttcccg gccctgctgc agggagctca aaatggagga 1260
cgcggcgctc gggagagcgg gcgggtgagt cacccacaca aaggaaaagg gccttttccgt 1320 cctcagccgt cgcttcatgt gactccacgg agtaccgggc gccgtccagg cacctcgatt 1380
agttctcgag cttttggagt acgtcgtctt taggttgggg ggaggggttt tatgcgatgg 1440
agtttcccca cactgagtgg gtggagactg aagttaggcc agcttggcac ttgatgtaat 1500
tctccttgga atttgccctt tttgagtttg gatcttggtt cattctcaag cctcagacag 1560
tggttcaaag tttttttctt ccatttcagg tgtcgtgagg atcc             1604

<210> SEQ ID NO 45
<211> LENGTH: 1667
<212> TYPE: DNA
<213> ORGANISM: Artificial Sequence
<220> FEATURE:
<223> OTHER INFORMATION: chimeric gene regulatory unit

<400> SEQUENCE: 45
acgcgttgac attgattatt gagtagttat taatagtaat caattacggg gtcattagtt   60
catagcccat atatggagtt ccgcgttaca taacttacgg taaatggccc gcctggctga  120
```

```
ccgcccaacg accccegccc attgacgtca ataatgacgt atgttcccat agtaacgcca        180
atagggactt tccattgacg tcaatgggtg gagtatttac ggtaaactgc ccacttggca        240
gtacatcaag tgtatcatat gccaagtccg cccctattg acgtcaatga cggtaaatgg         300
cccgcctggc attatgccca gtacatgacc ttacgggact ttcctacttg gcagtacatc        360
tacgtattag tcatcgctat tacagtcatt gggttttcc agccaattta attaaaacgc         420
catgtacttt cccaccattg acgtcaatgg gctattgaaa ctaatgcaac gtgacccttta       480 aacggtactt tcccatagct gattaatggg aaagtaccgt tctcgagcca atacacgtca        540
atgggaagtg aaagggcagc caaaacgtaa caccgccccg gttttccctg gaaattccat        600
attggcacgc attctattgg ctgagctgcg ttcacgtggg tataagaggc gcgaccagcg        660
tcggtaccgc ggccgccttt ttcgcaacgc gtttgccgcc agaacacagg taagtgccgt        720
gtgtggttcc cgcgggcctg gcctctttac gggttatggc ccttgcgtgc cttgaattac        780
ttccacgccc ctggctgcag tacgtgattc ttgatcccga gcttcgggtt ggaagtgggt        840
gggagagttc gaggccttgc gcttaaggag ccccttcgcc tcgtgcttga gttgaggcct        900
ggcctgggcg ctggggccgc cgcgtgcgaa tctggtggca ccttcgcgcc tgtctcgctg        960
ctttcgataa gtctctagcc atttaaaatt tttgatgacc tgctgcgacg ctttttttct       1020
ggcaagatag tcttgtaaat gcgggccaag atctgcacac tggtatttcg gtttttgggg      1080
ccgcgggcgg cgacggggcc cgtgcgtccc agcgcacatg ttcggcgagg cggggcctgc      1140
gagcgcggcc accgagaatc ggacgggggt agtctcaagc tggccggcct gctctggtgc      1200
ctggcctcgc gccgccgtgt atcgccccgc cctgggcggc aaggctggcc cggtcggcac      1260
cagttgcgtg agcggaaaga tggccgcttc ccggccctgc tgcagggagc tcaaaatgga      1320
ggacgcggcg ctcgggagag cgggcgggtg agtcacccac acaaaggaaa agggcctttc      1380
cgtcctcagc cgtcgcttca tgtgactcca cggagtaccg ggcgccgtcc aggcacctcg      1440
attagttctc gagcttttgg agtacgtcgt ctttaggttg gggggagggg ttttatgcga      1500
tggagtttcc ccacactgag tgggtggaga ctgaagttag gccagcttgg cacttgatgt      1560
aattctcctt ggaatttgcc cttttttgagt ttggatcttg gttcattctc aagcctcaga     1620
cagtggttca agttttttt cttccatttc aggtgtcgtg aggatcc                     1667
```

<210> SEQ ID NO 46
<211> LENGTH: 1491
<212> TYPE: DNA
<213> ORGANISM: Artificial Sequence
<220> FEATURE:
<223> OTHER INFORMATION: chimeric gene regulatory unit

<400> SEQUENCE: 46

```
acgcgttgac attgattatt gactagttat taatagtaat caattacggg gtcattagtt         60
catagcccat atatggagtt ccgcgttaca taacttacgg taaatggccc gcctggctga       120
ccgcccaacg accccgccc attgacgtca ataatgacgt atgttcccat agtaacgcca        180
atagggactt tccattgacg tcaatgggtg gagtatttac ggtaaactgc ccacttggca        240
gtacatcaag tgtatcatat gccaagtacg cccctattg acgtcaatga cggtaaatgg         300
cccgcctggc attatgccca gtacatgacc ttatgggact ttcctacttg gcagtacatc        360
tacgtattag tcatcgctat tactcccgcc cctaactccg cccatcccgc cctaactcc         420 gcccagttcc gcccattctc cgccccatgg ctgactaatt ttttttattt atgcagaggc        480
```

```
cgaggccgcc tcgcggccgc cttttttcgca acgggtttgc cgccagaaca caggtaagtg      540
ccgtgtgtgg ttcccgcggg cctggcctct ttacgggtta tggcccttgc gtgccttgaa      600
ttacttccac gcccctggct gcagtacgtg attcttgatc ccgagcttcg ggttggaagt      660
gggtgggaga gttcgaggcc ttgcgcttaa ggagccccct cgcctcgtgc ttgagttgag      720
gcctggcctg ggcgctgggg ccgccgcgtg cgaatctggt ggcaccttcg cgcctgtctc      780
gctgctttcg ataagtctct agccatttaa aattttttgat gacctgctgc gacgcttttt      840
ttctggcaag atagtcttgt aaatgcgggc caagatctgc acactggtat ttcggttttt      900
ggggccgcgg gcggcgacgg ggcccgtgcg tcccagcgca catgttcggc gaggcggggc      960
ctgcgagcgc ggccaccgag aatcggacgg gggtagtctc aagctggccg gcctgctctg     1020
gtgcctggcc tcgcgccgcc gtgtatcgcc ccgccctggg cggcaaggct ggcccggtcg     1080
gcaccagttg cgtgagcgga aagatggccg cttcccggcc ctgctgcagg gagctcaaaa     1140
tggaggacgc ggcgctcggg agagcgggcg ggtgagtcac ccacacaaag gaaaagggcc     1200
tttccgtcct cagccgtcgc ttcatgtgac tccacggagt accgggcgcc gtccaggcac     1260
ctcgattagt tctcgagctt ttggagtacg tcgtctttag gttggggggga ggggttttat     1320 gcgatggagt ttccccacac tgagtgggtg gagactgaag ttaggccagc ttggcacttg     1380
atgtaattct ccttggaatt tgccctttttt gagtttggat cttggttcat tctcaagcct     1440
cagacagtgg ttcaaagttt ttttcttcca tttcaggtgt cgtgaggatc c             1491

<210> SEQ ID NO 47
<211> LENGTH: 1583
<212> TYPE: DNA
<213> ORGANISM: Artificial Sequence
<220> FEATURE:
<223> OTHER INFORMATION: chimeric gene regulatory unit

<400> SEQUENCE: 47
acgcgttgac attgattatt gagtagttat taatagtaat caattacggg gtcattagtt       60
catagcccat atatggagtt ccgcgttaca taacttacgg taaatggccc gcctggctga      120
ccgcccaacg acccccgccc attgacgtca ataatgacgt atgttcccat agtaacgcca      180
atagggactt tccattgacg tcaatggggtg gagtatttac ggtaaactgc ccacttggca      240
gtacatcaag tgtatcatat gccaagtccg cccccctattg acgtcaatga cggtaaatgg      300
cccgcctggc attatgccca gtacatgacc ttacgggact ttcctacttg gcagtacatc      360
tacgtattag tcatcgctat tacactagtc gtgaggctcc ggtgcccgtc agtgggcaga      420
gcgcacatcg cccacagtcc ccgagaagtt gggggggaggg gtcggcaatt gaaccggtgc      480
ctagagaagg tggcgcgggg taaactggga aagtgatgtc gtgtactggc tccgcctttt      540
tcccgagggt gggggagaac cgtatataag tgcagtagtc gccgtgaacg ttcttttttcg      600 caacgggttt gccgccagaa cacaggtaag tgccgtgtgt ggttcccgcg gggcctggcct      660 ctttacgggt tatggccctt gcgtgccttg aattacttcc acgcccctgg ctgcagtacg      720
tgattcttga tcccgagctt cgggttggaa gtgggtggga gagttcgagg ccttgcgctt      780
aaggagcccc ttcgcctcgt gcttgagttg aggcctggcc tgggcgctgg ggccgccgcg      840
tgcgaatctg gtggcacctt cgcgcctgtc tcgctgcttt cgataagtct ctagccattt      900 aaaattttttg atgacctgct gcgacgcttt tttctggca agatagtctt gtaaatgcgg      960
gccaagatct gcacactggt atttcggttt ttggggccgc gggcggcgac ggggcccgtg     1020
cgtcccagcg cacatgttcg gcgaggcggg gcctgcgagc gcggccaccg agaatcggac     1080
```

```
ggggtagtc tcaagctggc cggcctgctc tggtgcctgg cctcgcgccg ccgtgtatcg    1140
ccccgccctg ggcggcaagg ctggcccggt cggcaccagt tgcgtgagcg aaagatggc    1200 cgcttcccgg ccctgctgca gggagctcaa aatggaggac gcggcgctcg ggagagcggg   1260
cgggtgagtc acccacacaa aggaaaaggg cctttccgtc ctcagccgtc gcttcatgtg   1320
actccacgga gtaccgggcg ccgtccaggc acctcgatta gttctcgagc ttttggagta   1380
cgtcgtcttt aggttggggg gaggggtttt atgcgatgga gtttccccac actgagtggg   1440
tggagactga agttaggcca gcttggcact tgatgtaatt ctccttggaa tttgcccttt   1500
ttgagtttgg atcttggttc attctcaagc ctcagacagt ggttcaaagt ttttttcttc   1560
catttcaggt gtcgtgagga tcc                                          1583
```

<210> SEQ ID NO 48
<211> LENGTH: 1661
<212> TYPE: DNA
<213> ORGANISM: Artificial Sequence
<220> FEATURE:
<223> OTHER INFORMATION: chimeric gene regulatory unit

<400> SEQUENCE: 48

```
acgcgttgac attgattatt gactagttat taatagtaat caattacggg gtcattagtt    60
catagcccat atatggagtt ccgcgttaca taacttacgg taaatggccc gcctggctga   120
ccgcccaacg acccccgccc attgacgtca ataatgacgt atgttcccat agtaacgcca   180
atagggactt tccattgacg tcaatgggtg gagtatttac ggtaaactgc ccacttggca   240
gtacatcaag tgtatcatat gccaagtacg ccccctattg acgtcaatga cggtaaatgg   300
cccgcctggc attatgccca gtacatgacc ttatgggact ttcctacttg gcagtacatc   360
tacgtattag tcatcgctat tacactagtt cgaggtgagc cccacgttct gcttcactct   420
ccccatctcc cccccctccc cacccccaat tttgtattta tttattttt aattattttg    480 tgcagcgatg ggggcggggg ggggggggc gcgcgccagg cggggcgggg cggggcgagg   540
ggcggggcgg ggcgaggcgg agaggtgcgg cggcagccaa tcagagcggc gcgctccgaa   600
agtttccttt tatggcgagg cggcggcggc ggcggcccta taaaaagcga agcgcgcggc   660
gggcggccgc cttttttcgca acgggtttgc cgccagaaca caggtaagtg ccgtgtgtgg   720
ttcccgcggg cctggcctct ttacgggtta tggcccttgc gtgccttgaa ttacttccac    780
gcccctggct gcagtacgtg attcttgatc ccgagcttcg ggttggaagt gggtgggaga   840
gttcgaggcc ttgcgcttaa ggagccccctt cgcctcgtgc ttgagttgag gcctggcctg   900
ggcgctgggg ccgccgcgtg cgaatctggt ggcaccttcg cgcctgtctc gctgctttcg   960
ataagtctct agccatttaa aattttttgat gacctgctgc gacgcttttt ttctggcaag   1020
atagtcttgt aaatgcgggc caagatctgc acactggtat ttcggttttt ggggccgcgg   1080
gcggcgacgg ggcccgtgcg tcccagcgca catgttcggc gaggcgggc ctgcgagcgc    1140 ggccaccgag aatcggacgg gggtagtctc aagctggccg gcctgctctg tgtgcctggcc   1200 tcgcgccgcc gtgtatcgcc ccgccctggg cggcaaggct ggcccggtcg caccagttg    1260 cgtgagcgga aagatggccg cttccccgcc ctgctgcagg gagctcaaaa tggaggacgc   1320
ggcgctcggg agagcgggcg gtgagtcac ccacacaaag gaaaagggcc tttccgtcct    1380
cagccgtcgc ttcatgtgac tccacggagt accgggcgcc gtccaggcac ctcgattagt   1440
tctcgagctt ttggagtacg tcgtctttag gttggggga ggggtttat gcgatggagt    1500
```

```
ttccccacac tgagtgggtg gagactgaag ttaggccagc ttggcacttg atgtaattct    1560
ccttggaatt tgccctttt  gagtttggat cttggttcat tctcaagcct cagacagtgg    1620
ttcaaagttt ttttcttcca tttcaggtgt cgtgaggatc c                        1661

<210> SEQ ID NO 49
<211> LENGTH: 1712
<212> TYPE: DNA
<213> ORGANISM: Artificial Sequence
<220> FEATURE:
<223> OTHER INFORMATION: chimeric gene regulatory unit

<400> SEQUENCE: 49
acgcgtagtc aatgggaaaa acccattgga gccaagtaca ctgactcaat agggactttc      60
cattgggttt tgcccagtac ataaggtcaa taggggtga gtcaacagga aagtcccatt      120
ggagccaagt acattgagtc aatagggact ttccaatggg ttttgcccag tacataaggt     180
caatgggagg taagccaatg gttttttccc attactggca cgtatactga gtcattaggg     240
actttccaat gggttttgcc cagtacataa ggtcaatagg ggtgaatcaa caggaaagtc     300
ccattggagc caagtacact gagtcaatag ggactttcca ttgggttttg cccagtacaa     360
aaggtcaata gggggtgagt caatgggttt ttcccattat tggcacgtac ataaggtcaa     420
taggggtgag tcattgggtt tttccagcca atttaattaa aacgccatgt actttcccac     480
cattgacgtc aatgggctat tgaaactaat gcaacgtgac ctttaaacgg tactttccca     540
tagctgatta atgggaaagt accgttctcg agccaataca cgtcaatggg aagtgaaagg     600
gcagccaaaa cgtaacaccg ccccggtttt ccctggaaat tccatattgg cacgcattct     660
attggctgag ctgcgttcac gtgggtataa gaggcgcgac cagcgtcggt accgcggccg     720
cctttttcgc aacgggttg ccgccagaac acaggtaagt gccgtgtgtg gttcccgcgg     780
gcctggcctc tttacgggtt atggcccttg cgtgccttga attacttcca cgcccctggc     840
tgcagtacgt gattcttgat cccgagcttc gggttggaag tgggtgggag agttcgaggc     900
cttgcgctta aggagcccct tcgcctcgtg cttgagttga ggcctggcct gggcgctggg     960
gccgccgcgt gcgaatctgg tggcaccttc gcgcctgtct cgctgctttc gataagtctc    1020
tagccattta aaattttga  tgacctgctg cgacgctttt tttctggcaa gatagtcttg    1080
taaatgcggg ccaagatctg cacactggta tttcggtttt tggggccgcg gcggcgacg     1140 gggcccgtgc gtcccagcgc acatgttcgg cgaggcgggg cctgcgagcg cggccaccga    1200
gaatcggacg ggggtagtct caagctgcc ggcctgctct ggtgcctggc ctcgcgccgc     1260
cgtgtatcgc cccgccctgg gcggcaaggc tggcccggtc ggcaccagtt gcgtgagcgg    1320
aaagatggcc gcttcccggc cctgctgcag ggagctcaaa atggaggacg cggcgctcgg    1380
gagagcgggc gggtgagtca cccacacaaa ggaaaagggc ctttccgtcc tcagccgtcg    1440
cttcatgtga ctccacggag taccgggcgc cgtccaggca cctcgattag ttctcgagct    1500
tttggagtac gtcgtcttta ggttgggggg aggggtttta tgcgatggag tttccccaca    1560
ctgagtgggt ggagactgaa gttaggccag cttggcactt gatgtaattc tccttggaat    1620 ttgcccctttt tgagtttgga tcttggttca ttctcaagcc tcagacagtg gttcaaagtt    1680 ttttcttcc atttcaggtg tcgtgaggat cc                                   1712

<210> SEQ ID NO 50
<211> LENGTH: 1655
<212> TYPE: DNA
<213> ORGANISM: Artificial Sequence
```

<220> FEATURE:
<223> OTHER INFORMATION: chimeric gene regulatory unit

<400> SEQUENCE: 50

```
acgcgtagtc aatgggaaaa acccattgga gccaagtaca ctgactcaat agggactttc      60
cattgggttt tgcccagtac ataaggtcaa taggggtga gtcaacagga aagtcccatt     120
ggagccaagt acattgagtc aatagggact ttccaatggg ttttgcccag tacataaggt    180
caatgggagg taagccaatg ggttttcccc attactggca cgtatactga gtcattaggg    240
actttccaat gggttttgcc cagtacataa ggtcaatagg ggtgaatcaa caggaaagtc    300
ccattggagc caagtacact gagtcaatag ggactttcca tgggttttg cccagtacaa     360
aaggtcaata gggggtgagt caatgggttt tcccattat tggcacgtac ataaggtcaa     420
taggggtgac tagtcatggt gatgcggttt tggcagtaca ccaatgggcg tggatagcgg    480
tttgactcac ggggatttcc aagtctccac cccattgacg tcaatgggag tttgttttgg    540
caccaaaatc aacgggactt tccaaaatgt cgtaataacc ccgccccgtt gacgcaaatg    600
ggcggtaggc gtgtacggtg gaaggtctat ataagcagag ctcgtttagt gaaccggcgg    660
ccgccttttt cgcaacgggt tgccgccag aacacaggta agtgccgtgt gtggttcccg     720
cgggcctggc ctctttacgg gttatggccc ttgcgtgcct tgaattactt ccacgcccct    780
ggctgcagta cgtgattctt gatcccgagc ttcgggttgg aagtgggtgg gagagttcga    840
ggccttgcgc ttaaggagcc ccttcgcctc gtgcttgagt tgaggcctgg cctgggcgct    900
ggggccgccg cgtgcgaatc tggtggcacc ttcgcgcctg tctcgctgct ttcgataagt    960
ctctagccat ttaaaatttt tgatgacctg ctgcgacgct ttttttctgg caagatagtc   1020
ttgtaaatgc gggccaagat ctgcacactg gtatttcggt ttttggggcc gcgggcggcg   1080
acggggcccg tgcgtcccag cgcacatgtt cggcgaggcg gggcctgcga gcgcggccac   1140
cgagaatcgg acggggtag tctcaagctg gccggcctgc tctggtgcct ggcctcgcgc   1200
cgccgtgtat cgccccgccc tgggcggcaa ggctggcccg gtcggcacca gttgcgtgag   1260
cggaaagatg gccgcttccc ggccctgctg caggagctc aaaatggagg acgcggcgct    1320
cgggagagcg ggcgggtgag tcacccacac aaaggaaaag gccttccg tcctcagccg     1380
tcgcttcatg tgactccacg gagtaccggg cgccgtccag gcacctcgat tagttctcga   1440
gcttttggag tacgtcgtct ttaggttggg gggagggggtt ttatgcgatg gagtttcccc   1500
acactgagtg ggtggagact gaagttaggc cagcttggca cttgatgtaa ttctccttgg   1560
aatttgccct ttttgagttt ggatcttggt tcattctcaa gcctcagaca gtggttcaaa   1620
gttttttttct tccatttcag gtgtcgtgag gatcc                              1655
```

<210> SEQ ID NO 51
<211> LENGTH: 1542
<212> TYPE: DNA
<213> ORGANISM: Artificial Sequence
<220> FEATURE:
<223> OTHER INFORMATION: chimeric gene regulatory unit

<400> SEQUENCE: 51

```
acgcgtagtc aatgggaaaa acccattgga gccaagtaca ctgactcaat agggactttc     60
cattgggttt tgcccagtac ataaggtcaa taggggtga gtcaacagga aagtcccatt    120
ggagccaagt acattgagtc aatagggact ttccaatggg ttttgcccag tacataaggt   180
caatgggagg taagccaatg ggttttcccc attactggca cgtatactga gtcattaggg   240
```

| | |
|---|---|
| actttccaat gggttttgcc cagtacataa ggtcaatagg ggtgaatcaa caggaaagtc | 300 |
| ccattggagc caagtacact gagtcaatag ggactttcca ttgggttttg cccagtacaa | 360 |
| aaggtcaata gggggtgagt caatgggttt ttcccattat tggcacgtac ataaggtcaa | 420 |
| taggggtgac tagttccgc ccctaactcc gcccatcccg ccctaactc cgcccagttc | 480 |
| cgcccattct ccgccccatg ctgactaat tttttttatt tatgcagagg ccgaggccgc | 540 |
| ctcgcggccg cctttttcgc aacgggtttg ccgccagaac acaggtaagt gccgtgtgtg | 600 |
| gttcccgcgg gcctggcctc tttacgggtt atggcccttg cgtgccttga attacttcca | 660 |
| cgcccctggc tgcagtacgt gattcttgat cccgagcttc gggttggaag tgggtgggag | 720 |
| agttcgaggc cttgcgctta aggagcccct tcgcctcgtg cttgagttga ggcctggcct | 780 |
| gggcgctggg gccgccgcgt gcgaatctgg tggcacctcc gcgcctgtct cgctgctttc | 840 |
| gataagtctc tagccattta aaatttttga tgacctgctg cgacgctttt tttctggcaa | 900 |
| gatagtcttg taaatgcggg ccaagatctg cacactggta tttcggtttt tggggccgcg | 960 |
| ggcggcgacg ggcccgtgc gtcccagcgc acatgttcgg cgaggcgggg cctgcgagcg | 1020 |
| cggccaccga gaatcggacg ggggtagtct caagctggcc ggcctgctct ggtgcctggc | 1080 |
| ctcgcgccgc cgtgtatcgc cccgcccctgg gcggcaaggc tggcccggtc ggcaccagtt | 1140 |
| gcgtgagcgg aaagatggcc gcttcccggc cctgctgcag ggagctcaaa atggaggacg | 1200 |
| cggcgctcgg gagagcgggc gggtgagtca cccacacaaa ggaaaagggc ctttccgtcc | 1260 |
| tcagccgtcg cttcatgtga ctccacggag taccgggcgc cgtccaggca cctcgattag | 1320 |
| ttctcgagct tttggagtac gtcgtctta ggttgggggg aggggttta tgcgatggag | 1380 |
| tttccccaca ctgagtgggt ggagactgaa gttaggccag cttggcactt gatgtaattc | 1440 |
| tccttggaat ttgcccttt tgagtttgga tcttggttca ttctcaagcc tcagacagtg | 1500 |
| gttcaaagtt ttttcttcc atttcaggtg tcgtgaggat cc | 1542 |

<210> SEQ ID NO 52
<211> LENGTH: 1628
<212> TYPE: DNA
<213> ORGANISM: Artificial Sequence
<220> FEATURE:
<223> OTHER INFORMATION: chimeric gene regulatory unit

<400> SEQUENCE: 52

| | |
|---|---|
| acgcgtagtc aatgggaaaa acccattgga gccaagtaca ctgactcaat agggactttc | 60 |
| cattgggttt tgcccagtac ataaggtcaa taggggtga gtcaacagga aagtcccatt | 120 |
| ggagccaagt acattgagtc aatagggact ttccaatggg ttttgcccag tacataaggt | 180 |
| caatgggagg taagccaatg ggttttccc attactggca cgtatactga gtcattaggg | 240 |
| actttccaat gggttttgcc cagtacataa ggtcaatagg ggtgaatcaa caggaaagtc | 300 |
| ccattggagc caagtacact gagtcaatag ggactttcca ttgggttttg cccagtacaa | 360 |
| aaggtcaata gggggtgagt caatgggttt ttcccattat tggcacgtac ataaggtcaa | 420 |
| taggggtgac tagtcgtgag gctccggtgc ccgtcagtgg gcagagcgca catcgcccac | 480 |
| agtccccgag aagttggggg gaggggtcgg caattgaacc ggtgcctaga aaggtggcg | 540 |
| cggggtaaac tgggaaagtg atgtcgtgta ctggctccgc cttttcccg agggtggggg | 600 |
| agaaccgtat ataagtgcag tagtcgccgt gaacgttctt tttcgcaacg ggtttgccgc | 660 |
| cagaacacag gtaagtgccg tgtgtggttc ccgcgggcct ggcctcttta cgggttatgg | 720 |
| cccttgcgtg ccttgaatta cttccacgcc cctggctgca gtacgtgatt cttgatcccg | 780 |

```
agcttcgggt tggaagtggg tgggagagtt cgaggccttg cgcttaagga gccccttcgc      840
ctcgtgcttg agttgaggcc tggcctgggc gctggggccg ccgcgtgcga atctggtggc      900
accttcgcgc ctgtctcgct gctttcgata agtctctagc catttaaaat ttttgatgac      960
ctgctgcgac gcttttttc tggcaagata gtcttgtaaa tgcgggccaa gatctgcaca      1020
ctggtatttc ggttttgg gccgcgggcg gcgacgggc ccgtgcgtcc cagcgcacat       1080
gttcggcgag gcggggcctg cgagcgcggc caccgagaat cggacggggg tagtctcaag      1140
ctggccggcc tgctctggtg cctggcctcg cgccgccgtg tatcgccccg ccctgggcgg      1200
caaggctggc ccgtcggca ccagttgcgt gagcggaaag atggccgctt ccggccctg       1260 ctgcagggag ctcaaaatgg aggacgcggc gctcgggaga gcgggcgggt gagtcaccca      1320
cacaaaggaa aagggccttt ccgtcctcag ccgtcgcttc atgtgactcc acggagtacc      1380
gggcgccgtc caggcacctc gattagttct cgagcttttg gagtacgtcg tctttaggtt      1440
gggggagggg gttttatgcg atggagtttc cccacactga gtgggtggag actgaagtta      1500
ggccagcttg gcacttgatg taattctcct tggaatttgc ccttttgag tttggatctt       1560 ggttcattct caagcctcag acagtggttc aaagtttttt tcttccattt caggtgtcgt      1620
gaggatcc                                                              1628

<210> SEQ ID NO 53
<211> LENGTH: 1714
<212> TYPE: DNA
<213> ORGANISM: Artificial Sequence
<220> FEATURE:
<223> OTHER INFORMATION: chimeric gene regulatory unit

<400> SEQUENCE: 53
acgcgtagtc aatgggaaaa acccattgga gccaagtaca ctgactcaat agggactttc       60
cattgggttt tgcccagtac ataaggtcaa taggggtga gtcaacagga aagtcccatt       120
ggagccaagt acattgagtc aataggggact ttccaatggg ttttgcccag tacataaggt     180
caatgggagg taagccaatg gttttttccc attactggca cgtatactga gtcattaggg      240
actttccaat gggttttgcc cagtacataa ggtcaatagg ggtgaatcaa caggaaagtc      300
ccattggagc caagtacact gagtcaatag gactttcca ttgggttttg cccagtacaa       360
aaggtcaata gggggtgagt caatgggttt ttcccattat ggcacgtac ataaggtcaa        420 tagggggtgac tagttcgagg tgagccccac gttctgcttc actctcccca tctccccccc      480
ctccccaccc ccaatttgt atttatttat tttttaatta ttttgtgcag cgatgggggc       540
gggggggggg gggcgcgcg ccaggcgggg cggggcgggg cgaggggcgg ggcggggcga       600
ggcggagagg tgcggcggca gccaatcaga gcggcgcgct ccgaaagttt cctttatgg       660 cgaggcggcg gcggcggcgg ccctataaaa agcgaagcgc gcggcgggcg gccgcgcggc      720 cgccttttc gcaacgggtt tgccgccaga acacaggtaa gtgccgtgtg tggttcccgc       780
gggcctggcc tctttacggg ttatggccct tgcgtgcctt gaattacttc cacgcccctg      840
gctgcagtac gtgattcttg atcccgagct tcggttgga agtgggtggg agagttcgag      900
gccttgcgct taaggagccc cttcgcctcg tgcttgagtt gaggcctggc ctgggcgctg      960
gggccgccgc gtgcgaatct ggtggcacct tcgcgcctgt ctcgctgctt tcgataagtc     1020
tctagccatt taaaattttt gatgacctgc tgcgacgctt ttttctggc aagatagtct      1080 tgtaaatgcg ggccaagatc tgcacactgg tatttcggtt tttggggccg cgggcggcga    1140
```

```
cggggcccgt gcgtcccagc gcacatgttc ggcgaggcgg ggcctgcgag cgcggccacc    1200
gagaatcgga cggggtagt  ctcaagctgg ccggcctgct ctggtgcctg gcctcgcgcc    1260
gccgtgtatc gccccgccct gggcggcaag gctggcccgg tcggcaccag ttgcgtgagc    1320
ggaaagatgg ccgcttcccg gccctgctgc agggagctca aaatggagga cgcggcgctc    1380
gggagagcgg gcgggtgagt cacccacaca aaggaaaagg gcctttccgt cctcagccgt    1440
cgcttcatgt gactccacgg agtaccgggc gccgtccagg cacctcgatt agttctcgag    1500
cttttggagt acgtcgtctt taggttgggg ggaggggttt tatgcgatgg agtttcccca    1560
cactgagtgg gtggagactg aagttaggcc agcttggcac ttgatgtaat tctccttgga    1620
atttgccctt tttgagtttg gatcttggtt cattctcaag cctcagacag tggttcaaag    1680 ttttttttctt ccatttcagg tgtcgtgagg atcc                               1714
```

<210> SEQ ID NO 54
<211> LENGTH: 1282
<212> TYPE: DNA
<213> ORGANISM: Artificial Sequence
<220> FEATURE:
<223> OTHER INFORMATION: chimeric gene regulatory unit

<400> SEQUENCE: 54

```
acgcgttgtg gaatgtgtgt cagttagggt gtggaaagtc cccaggctcc ccagcaggca      60
gaagtatgca aagcatgcat ctcaattagt cagcaaccag gtgtggaaag tcccaggct     120 ccccagcagg cagaagtatg caaagcatgc atctcaatta gtcagcaacc atagtcccgc    180
ccctaactcc gcccatcccg ccctaactcc gcccagttc  cgccattct  ccgccccatg    240 gctgactaat ttttttatt  tatgcagagg ccgaggccgc ctcgcggccg ccttttttcgc   300 aacgggtttg ccgccagaac acaggtaagt gccgtgtgtg gttcccgcgg gcctggcctc    360
tttacgggtt atggcccttg cgtgccttga attacttcca cgcccctggc tgcagtacgt    420
gattcttgat cccgagcttc gggttggaag tgggtgggag agttcgaggc cttgcgctta    480
aggagcccct tcgcctcgtg cttgagttga ggcctggcct gggcgctggg gccgccgcgt    540
gcgaatctgg tggcaccttc gcgcctgtct cgctgctttc gataagtctc tagccattta    600 aaattttga  tgacctgctg cgacgctttt tttctggcaa gatagtcttg taaatgcggg    660
ccaagatctg cacactggta tttcggtttt tggggccgcg ggcggcgacg gggcccgtgc    720
gtcccagcgc acatgttcgg cgaggcgggg cctgcgagcg cggccaccga gaatcggacg    780
ggggtagtct caagctggcc ggcctgctct ggtgcctggc ctcgcgccgc cgtgtatcgc    840
cccgccctgg gcggcaaggc tggcccggtc ggcaccagtt gcgtgagcgg aaagatggcc    900
gcttcccggc cctgctgcag ggagctcaaa atggaggacg cggcgctcgg gagagcgggc    960
gggtgagtca cccacacaaa ggaaaagggc ctttccgtcc tcagccgtcg cttcatgtga   1020
ctccacggag taccgggcgc cgtccaggca cctcgattag ttctcgagct tttggagtac   1080
gtcgtcttta ggttgggggg aggggtttta tgcgatggag tttccccaca ctgagtgggt   1140
ggagactgaa gttaggccag cttggcactt gatgtaattc ccttggaat ttgcccttttt   1200 tgagtttgga tcttggttca ttctcaagcc tcagacagtg gttcaaagtt ttttcttcc    1260 atttcaggtg tcgtgaggat cc                                            1282
```

<210> SEQ ID NO 55
<211> LENGTH: 1402
<212> TYPE: DNA
<213> ORGANISM: Artificial Sequence
<220> FEATURE:
<223> OTHER INFORMATION: chimeric gene regulatory unit

<400> SEQUENCE: 55

| | | |
|---|---|---|
| acgcgttgtg gaatgtgtgt cagttagggt gtggaaagtc cccaggctcc ccagcaggca | 60 |
| gaagtatgca aagcatgcat ctcaattagt cagcaaccag gtgtggaaag tccccaggct | 120 |
| ccccagcagg cagaagtatg caaagcatgc atctcaatta gtcagcaacc atagactagt | 180 |
| catggtgatg cggttttggc agtacaccaa tgggcgtgga tagcggtttg actcacgggg | 240 |
| atttccaagt ctccacccca ttgacgtcaa tgggagtttg ttttggcacc aaaatcaacg | 300 |
| ggactttcca aaatgtcgta ataaccccgc ccgttgacg caaatgggcg gtaggcgtgt | 360 |
| acggtgggag gtctatataa gcagagctcg tttagtgaac cgtgcggccg ccttttttcgc | 420 |
| aacgggtttg ccgccagaac acaggtaagt gccgtgtgtg gttcccgcgg gcctggcctc | 480 |
| tttacgggtt atggcccttg cgtgccttga attacttcca cgccctggc tgcagtacgt | 540 |
| gattcttgat cccgagcttc gggttggaag tgggtgggag agttcgaggc cttgcgctta | 600 |
| aggagcccct tcgcctcgtg cttgagttga ggcctggcct gggcgctggg gccgccgcgt | 660 |
| gcgaatctgg tggcaccttc gcgcctgtct cgctgctttc gataagtctc tagccattta | 720 |
| aaattttttga tgacctgctg cgacgctttt tttctggcaa gatagtcttg taaatgcggg | 780 |
| ccaagatctg cacactggta tttcggtttt tggggccgcg ggcggcgacg gggcccgtgc | 840 |
| gtcccagcgc acatgttcgg cgaggcgggg cctgcgagcg cggccaccga gaatcggacg | 900 |
| ggggtagtct caagctggcc ggcctgctct ggtgcctggc ctcgcgccgc cgtgtatcgc | 960 |
| cccgccctgg gcggcaaggc tggcccggtc ggcaccagtt gcgtgagcgg aaagatggcc | 1020 |
| gcttcccggc cctgctgcag ggagctcaaa atggaggacg cggcgctcgg gagagcgggc | 1080 |
| gggtgagtca cccacacaaa ggaaaagggc cttccgtcc tcagccgtcg cttcatgtga | 1140 |
| ctccacggag taccgggcgc cgtccaggca cctcgattag ttctcgagct tttggagtac | 1200 |
| gtcgtctta ggttgggggg aggggttta tgcgatggag tttccccaca ctgagtgggt | 1260 |
| ggagactgaa gttaggccag cttggcactt gatgtaattc tccttggaat ttgccctttt | 1320 |
| tgagtttgga tcttggttca ttctcaagcc tcagacagtg gttcaaagtt ttttcttcc | 1380 |
| atttcaggtg tcgtgaggat cc | 1402 |

<210> SEQ ID NO 56
<211> LENGTH: 1464
<212> TYPE: DNA
<213> ORGANISM: Artificial Sequence
<220> FEATURE:
<223> OTHER INFORMATION: chimeric gene regulatory unit

<400> SEQUENCE: 56

| | | |
|---|---|---|
| acgcgttgtg gaatgtgtgt cagttagggt gtggaaagtc cccaggctcc ccagcaggca | 60 |
| gaagtatgca aagcatgcat ctcaattagt cagcaaccag gtgtggaaag tccccaggct | 120 |
| ccccagcagg cagaagtatg caaagcatgc atctcaatta gtcagcaacc atagactagt | 180 |
| agtcattggg ttttttccagc caatttaatt aaaacgccat gtactttccc accattgacg | 240 |
| tcaatgggct attgaaacta atgcaacgtg acctttaaac ggtactttcc catagctgat | 300 |
| taatgggaaa gtaccgttct cgagccaata cacgtcaatg ggaagtgaaa gggcagccaa | 360 |
| aacgtaacac cgccccggtt ttccctggaa attccatatt ggcacgcatt ctattggctg | 420 |
| agctgcgttc acgtgggtat aagaggcgcg accagcgtcg gtaccgcggc cgcctttttc | 480 |

```
gcaacgggtt tgccgccaga acacaggtaa gtgccgtgtg tggttcccgc gggcctggcc      540
tctttacggg ttatggccct tgcgtgcctt gaattacttc cacgccctg gctgcagtac       600 gtgattcttg atcccgagct tcgggttgga agtgggtggg agagttcgag gccttgcgct      660
taaggagccc cttcgcctcg tgcttgagtt gaggcctggc ctgggcgctg gggccgccgc      720
gtgcgaatct ggtggcacct tcgcgcctgt ctcgctgctt tcgataagtc tctagccatt      780 taaaatttt gatgacctgc tgcgacgctt tttttctggc aagatagtct tgtaaatgcg       840
ggccaagatc tgcacactgg tatttcggtt tttggggccg cgggcggcga cggggcccgt      900
gcgtcccagc gcacatgttc ggcgaggcgg ggcctgcgag cgcggccacc gagaatcgga      960 cggggggtagt ctcaagctgg ccggcctgct ctggtgcctg gcctcgcgcc gccgtgtatc    1020
gccccgccct gggcggcaag gctggcccgg tcggcaccag ttgcgtgagc ggaaagatgg     1080
ccgcttcccg gccctgctgc agggagctca aaatggagga cgcggcgctc gggagagcgg     1140
gcgggtgagt cacccacaca aaggaaaagg gcctttccgt cctcagccgt cgcttcatgt     1200
gactccacgg agtaccgggc gccgtccagg cacctcgatt agttctcgag cttttggagt     1260
acgtcgtctt taggttgggg ggaggggttt tatgcgatgg agtttcccca cactgagtgg     1320
gtggagactg aagttaggcc agcttggcac ttgatgtaat tctccttgga atttgccctt     1380
tttgagtttg gatcttggtt cattctcaag cctcagacag tggttcaaag tttttttctt     1440
ccatttcagg tgtcgtgagg atcc                                            1464
```

<210> SEQ ID NO 57
<211> LENGTH: 1374
<212> TYPE: DNA
<213> ORGANISM: Artificial Sequence
<220> FEATURE:
<223> OTHER INFORMATION: chimeric gene regulatory unit

<400> SEQUENCE: 57

```
acgcgttgtg gaatgtgtgt cagttagggt gtggaaagtc cccaggctcc ccagcaggca       60
gaagtatgca aagcatgcat ctcaattagt cagcaaccag gtgtggaaag tccccaggct      120
ccccagcagg cagaagtatg caaagcatgc atctcaatta gtcagcaacc atagactagt      180
cgtgaggctc cggtgcccgt cagtgggcag agcgcacatc gcccacagtc cccgagaagt      240
tggggggagg ggtcggcaat tgaaccggtg cctagagaag gtggcgcggg gtaaactggg      300
aaagtgatgt cgtgtactgg ctccgccttt ttcccgaggg tgggggagaa ccgtatataa      360
gtgcagtagt cgccgtgaac gttctttttc gcaacgggtt tgccgccaga acacaggtaa      420
gtgccgtgtg tggttcccgc gggcctggcc tctttacggg ttatggccct tgcgtgcctt      480
gaattacttc cacgccctg gctgcagtac gtgattcttg atcccgagct tcgggttgga       540
agtgggtggg agagttcgag gccttgcgct taaggagccc cttcgcctcg tgcttgagtt      600
gaggcctggc ctgggcgctg gggccgccgc gtgcgaatct ggtggcacct tcgcgcctgt      660
ctcgctgctt tcgataagtc tctagccatt taaaatttt gatgacctgc tgcgacgctt      720
tttttctggc aagatagtct tgtaaatgcg ggccaagatc tgcacactgg tatttcggtt      780
tttggggccg cgggcggcga cggggcccgt gcgtcccagc gcacatgttc ggcgaggcgg     840
ggcctgcgag cgcggccacc gagaatcgga cggggggtagt ctcaagctgg ccggcctgct    900
ctggtgcctg gcctcgcgcc gccgtgtatc gccccgccct gggcggcaag gctggcccgg     960
tcggcaccag ttgcgtgagc ggaaagatgg ccgcttcccg gccctgctgc agggagctca    1020
aaatggagga cgcggcgctc gggagagcgg gcgggtgagt cacccacaca aaggaaaagg    1080
```

```
gcctttccgt cctcagccgt cgcttcatgt gactccacgg agtaccgggc gccgtccagg    1140
cacctcgatt agttctcgag cttttggagt acgtcgtctt taggttgggg ggaggggttt    1200
tatgcgatgg agtttcccca cactgagtgg gtggagactg aagttaggcc agcttggcac    1260
ttgatgtaat tctccttgga atttgccctt tttgagtttg gatcttggtt cattctcaag    1320
cctcagacag tggttcaaag ttttttttctt ccatttcagg tgtcgtgagg atcc         1374
```

<210> SEQ ID NO 58
<211> LENGTH: 1455
<212> TYPE: DNA
<213> ORGANISM: Artificial Sequence
<220> FEATURE:
<223> OTHER INFORMATION: chimeric gene regulatory unit

<400> SEQUENCE: 58

```
acgcgttgtg gaatgtgtgt cagttagggt gtggaaagtc cccaggctcc ccagcaggca      60
gaagtatgca aagcatgcat ctcaattagt cagcaaccag gtgtggaaag tccccaggct    120
ccccagcagg cagaagtatg caaagcatgc atctcaatta gtcagcaacc atagactagt    180
tcgaggtgag ccccacgttc tgcttcactc tcccccatctc cccccctcc caccccccaa     240 ttttgtatt atttatttt taattattt gtgcagcgat ggggggcggg gggggggggg      300
cgcgcgccag gcggggcggg gcggggcgag gggcggggcg gggcgaggcg gagaggtgcg    360
gcggcagcca atcagagcgg cgcgctccga aagtttcctt ttatggcgag gcggcggcgg    420
cggcggccct ataaaagcg aagcgcgcgg cgggcggcgg ccgccttttt cgcaacgggt     480
ttgccgccag aacacaggta agtgccgtgt gtggttcccg cgggcctggc ctctttacgg    540
gttatggccc ttgcgtgcct tgaattactt ccacgcccct ggctgcagta cgtgattctt    600
gatcccgagc ttcgggttgg aagtgggtgg gagagttcga ggccttgcgc ttaaggagcc    660
ccttcgcctc gtgcttgagt tgaggcctgg cctgggcgct ggggccgccg cgtgcgaatc    720
tggtggcacc ttcgcgcctg tctcgctgct ttcgataagt ctctagccat ttaaaatttt    780
tgatgacctg ctgcgacgct ttttttctgg caagatagtc ttgtaaatgc gggccaagat    840
ctgcacactg gtatttcggt ttttggggcc gcgggcggcg acggggcccg tgcgtcccag    900
cgcacatgtt cggcgaggcg gggcctgcga gcgcggccac cgagaatcgg acggggtag    960 tctcaagctg gccggcctgc tctggtgcct ggcctcgcgc cgccgtgtat cgccccgccc   1020
tgggcggcaa ggctggcccg gtcggcacca gttgcgtgag cggaaagatg gccgcttccc   1080
ggccctgctg cagggagctc aaaatggagg acgcggcgct cgggagagcg ggcgggtgag   1140
tcacccacac aaaggaaaag ggcctttccg tcctcagccg tcgcttcatg tgactccacg   1200
gagtaccggg cgccgtccag gcacctcgat tagttctcga cttttggag tacgtcgtct   1260 ttaggttggg gggagggggtt ttatgcgatg gagtttcccc acactgagtg ggtggagact   1320
gaagttaggc cagcttggca cttgatgtaa ttctccttgg aatttgccct ttttgagttt   1380
ggatcttggt tcattctcaa gcctcagaca gtggttcaaa gttttttttct tccatttcag   1440 gtgtcgtgag gatcc                                                    1455
```

<210> SEQ ID NO 59
<211> LENGTH: 1618
<212> TYPE: DNA
<213> ORGANISM: Artificial Sequence
<220> FEATURE:
<223> OTHER INFORMATION: chimeric gene regulatory unit

<400> SEQUENCE: 59

```
acgcgttgac attgattatt gagtagttat taatagtaat caattacggg gtcattagtt      60
catagcccat atatggagtt ccgcgttaca taacttacgg taaatggccc gcctggctga     120
ccgcccaacg accccccgccc attgacgtca ataatgacgt atgttcccat agtaacgcca    180
atagggactt tccattgacg tcaatgggtg gagtatttac ggtaaactgc ccacttggca     240
gtacatcaag tgtatcatat gccaagtccg cccctattg acgtcaatga cggtaaatgg      300
cccgcctggc attatgccca gtacatgacc ttacgggact ttcctacttg gcagtacatc     360
tacgtattag tcatcgctat taccatggtg atgcggtttt ggcagtacac caatgggcgt     420
ggatagcggt ttgactcacg gggatttcca agtctccacc ccattgacgt caatgggagt     480
ttgttttggc accaaaatca acgggacttt ccaaaatgtc gtaataaccc cgccccgttg     540
acgcaaatgg gcggtaggcg tgtacggtgg gaggtctata taagcagagc tcgtttagtg     600
aaccggcggc cgcggagtcg ctgcgttgcc ttcgccccgt gccccgctcc gcgccgcctc     660
gcgccgcccg cccggctct gactgaccgc gttactccca caggtgagcg ggcgggacgg      720
cccttctcct ccgggctgta attagcgctt ggtttaatga cggctcgttt cttttctgtg     780
gctgcgtgaa agccttaaag ggctccggga gggcccttg tgcggggggg agcggctcgg      840
ggggtgcgtg cgtgtgtgtg tgcgtgggga gcgccgcgtg cggcccgcgc tgcccggcgg     900
ctgtgagcgc tgcgggcgcg gcgcggggct ttgtgcgctc cgcgtgtgcg cgaggggagc     960
gcggccgggg gcggtgcccc gcggtgcggg ggggctgcga ggggaacaaa ggctgcgtgc    1020
ggggtgtgtg cgtgggggg tgagcagggg gtgtgggcgc ggcggtcggg ctgtaaccc      1080
cccctgcacc cccctccccg agttgctgag cacggcccgg cttcgggtgc ggggctccgt    1140
gcggggcgtg gcgcggggct cgccgtgccg ggcggggggt ggcggcaggt gggggtgccg    1200
ggcggggcgg ggccgcctcg ggccggggag ggctcggggg aggggcgcgg cggccccgga    1260
gcgccggcg ctgtcgaggc gcggcgagcc gcagccattg cctttttatgg taatcgtgcg    1320
agagggcgca gggacttcct ttgtcccaaa tctggcggag ccgaaatctg ggaggcgccg    1380
ccgcacccc tctagcgggc gcgggcgaag cggtgcggcg ccggcaggaa ggaaatgggc     1440
ggggagggcc ttcgtgcgtc gccgcgccgc cgtccccttc tccatctcca gcctcgggc     1500
tgccgcaggg ggacggctgc cttcgggggg gacggggcag ggcgggttc ggcttctggc     1560
gtgtgaccgg cggggtttat atcttccctt ctctgttcct ccgcagccag ccggatcc      1618
```

<210> SEQ ID NO 60
<211> LENGTH: 1681
<212> TYPE: DNA
<213> ORGANISM: Artificial Sequence
<220> FEATURE:
<223> OTHER INFORMATION: chimeric gene regulatory unit

<400> SEQUENCE: 60

```
acgcgttgac attgattatt gagtagttat taatagtaat caattacggg gtcattagtt      60
catagcccat atatggagtt ccgcgttaca taacttacgg taaatggccc gcctggctga     120
ccgcccaacg accccccgccc attgacgtca ataatgacgt atgttcccat agtaacgcca    180
atagggactt tccattgacg tcaatgggtg gagtatttac ggtaaactgc ccacttggca     240
gtacatcaag tgtatcatat gccaagtccg cccctattg acgtcaatga cggtaaatgg      300
cccgcctggc attatgccca gtacatgacc ttacgggact ttcctacttg gcagtacatc     360
tacgtattag tcatcgctat tacagtcatt gggttttcc agccaattta attaaaacgc      420
```

```
catgtacttt cccaccattg acgtcaatgg gctattgaaa ctaatgcaac gtgaccttta      480
aacggtactt tcccatagct gattaatggg aaagtaccgt tctcgagcca atacacgtca      540
atgggaagtg aaagggcagc caaaacgtaa caccgccccg gttttccctg gaaattccat      600
attggcacgc attctattgg ctgagctgcg ttcacgtggg tataagaggc gcgaccagcg      660
tcggtaccgc ggccgcggag tcgctgcgtt gccttcgccc cgtgccccgc tccgcgccgc      720
ctcgcgccgc ccgccccggc tctgactgac cgcgttactc ccacaggtga gcgggcggga      780
cggcccttct cctccgggct gtaattagcg cttggtttaa tgacggctcg tttctttttct     840
gtggctgcgt gaaagcctta aagggctccg ggagggccct tgtgcgggg gggagcggct       900
cgggggggtgc gtgcgtgtgt gtgtgcgtgg ggagcgccgc gtgcggcccg cgctgcccgg    960
cggctgtgag cgctgcgggc gcggcgcggg gctttgtgcg ctccgcgtgt gcgcgagggg    1020
agcgcggccg ggggcggtgc cccgcggtgc gggggggctg cgagggggaac aaaggctgcg     1080
tgcggggtgt gtgcgtgggg gggtgagcag gggtgtggg cgcggcggtc gggctgtaac     1140
cccccctgc accccctcc ccgagttgct gagcacggcc cggcttcggg tgcggggctc       1200
cgtgcggggc gtggcgcggg gctcgccgtg ccggccgggg ggtggcggca ggtggggtg      1260
ccgggcgggg cggggccgcc tcgggccggg gagggctcgg gggaggggcg cggcggcccc    1320
ggagcgccgg cggctgtcga ggcgcggcga gccgcagcca ttgccttta tggtaatcgt       1380
gcgagagggc gcagggactt cctttgtccc aaatctggcg gagccgaaat ctgggaggcg      1440
ccgccgcacc ccctctagcg ggcgcgggcg aagcggtgcg gcgccggcag gaaggaaatg     1500
ggcggggagg gccttcgtgc gtcgccgcgc cgccgtcccc ttctccatct ccagcctcgg    1560
ggctgccgca ggggacggc tgccttcggg ggggacgggg cagggcgggg ttcggcttct      1620
ggcgtgtgac cggcggggtt tatatcttcc cttctctgtt cctccgcagc cagccggatc    1680
c                                                                     1681
```

<210> SEQ ID NO 61
<211> LENGTH: 1505
<212> TYPE: DNA
<213> ORGANISM: Artificial Sequence
<220> FEATURE:
<223> OTHER INFORMATION: chimeric gene regulatory unit

<400> SEQUENCE: 61

```
acgcgttgac attgattatt gactagttat taatagtaat caattacggg gtcattagtt       60
catagcccat atatggagtt ccgcgttaca taacttacgg taaatggccc gcctggctga      120
ccgcccaacg accccgccc attgacgtca ataatgacgt atgttcccat agtaacgcca      180
atagggactt tccattgacg tcaatgggtg gagtatttac ggtaaactgc ccacttggca      240
gtacatcaag tgtatcatat gccaagtacg ccccctattg acgtcaatga cggtaaatgg      300
cccgcctggc attatgccca gtacatgacc ttatgggact ttcctacttg gcagtacatc      360
tacgtattag tcatcgctat tactcccgcc cctaactccg cccatcccgc cctaactcc       420
gcccagttcc gcccattctc cgccccatgg ctgactaatt ttttttattt atgcagaggc      480
cgaggccgcc tcgcggccgc ggagtcgctg cgttgccttc gccccgtgcc ccgctccgcg      540
ccgcctcgcg ccgcccgccc cggctctgac tgaccgcgtt actcccacag gtgagcgggc      600
gggacgcc ttctcctccg gctgtaatt agcgcttggt ttaatgacgg ctcgtttctt        660
ttctgtggct gcgtgaaagc cttaaagggc tccgggaggg ccctttgtgc gggggggagc      720
```

```
ggctcggggg gtgcgtgcgt gtgtgtgtgc gtggggagcg ccgcgtgcgg cccgcgctgc    780
ccggcggctg tgagcgctgc gggcgcggcg cggggctttg tgcgctccgc gtgtgcgcga    840
ggggagcgcg gccggggggcg gtgccccgcg gtgcgggggg gctgcgaggg gaacaaaggc    900
tgcgtgcggg gtgtgtgcgt gggggggtga gcaggggggtg tgggcgcggc ggtcgggctg   960
taaccccccc ctgcacccccc ctccccgagt tgctgagcac ggcccggctt cgggtgcggg  1020
gctccgtgcg gggcgtggcg cggggctcgc cgtgccgggc gggggggtggc ggcaggtggg 1080 ggtgccgggc ggggcggggc cgcctcgggc cggggagggc tcggggggagg ggcgcggcgg 1140 ccccggagcg ccggcggctg tcgaggcgcg gcgagccgca gccattgcct tttatggtaa  1200
tcgtgcgaga gggcgcaggg acttcctttg tcccaaatct ggcggagccg aaatctggga  1260
ggcgccgccg cacccctct agcgggcgcg ggcgaagcgg tgcggcgccg gcaggaagga   1320
aatgggcggg gagggccttc gtgcgtcgcc gcgccgccgt ccccttctcc atctccagcc  1380
tcggggctgc cgcaggggga cggctgcctt cggggggggac ggggcagggc ggggttcggc 1440
ttctggcgtg tgaccggcgg ggtttatatc ttcccttctc tgttcctccg cagccagccg  1500
gatcc                                                               1505

<210> SEQ ID NO 62
<211> LENGTH: 1605
<212> TYPE: DNA
<213> ORGANISM: Artificial Sequence
<220> FEATURE:
<223> OTHER INFORMATION: chimeric gene regulatory unit

<400> SEQUENCE: 62
acgcgttgac attgattatt gagtagttat taatagtaat caattacggg gtcattagtt    60
catagcccat atatggagtt ccgcgttaca taacttacgg taaatggccc gcctggctga   120
ccgcccaacg accccgccc attgacgtca ataatgacgt atgttcccat agtaacgcca    180
atagggactt tccattgacg tcaatgggtg gagtatttac ggtaaactgc ccacttggca   240
gtacatcaag tgtatcatat gccaagtccg cccctattg acgtcaatga cggtaaatgg   300
cccgcctggc attatgccca gtacatgacc ttacgggact ttcctacttg gcagtacatc   360
tacgtattag tcatcgctat tacactagtc gtgaggctcc ggtgcccgtc agtgggcaga   420
gcgcacatcg cccacagtcc ccgagaagtt gggggggaggg gtcggcaatt gaaccggtgc   480
ctagagaagg tggcgcgggg taaactggga aagtgatgtc gtgtactggc tccgcctttt   540
tcccgagggt gggggagaac cgtatataag tgcagtagtc gccgtgaacg ttgcggccgc   600
ggagtcgctg cgttgccttc gccccgtgcc ccgctccgcg ccgcctcgcg ccgcccgccc   660
cggctctgac tgaccgcgtt actcccacag gtgagcgggc gggacggccc ttctcctccg   720
ggctgtaatt agcgcttggt ttaatgacgg ctcgtttctt ttctgtggct gcgtgaaagc   780
cttaaagggc tccggagggg ccctttgtgc gggggggagc ggctcggggg gtgcgtgcgt   840
gtgtgtgtgc gtggggagcg ccgcgtgcgg cccgcgctgc ccggcggctg tgagcgctgc   900
gggcgcggcg cggggctttg tgcgctccgc gtgtgcgcga ggggagcgcg gccggggggcg   960 gtgccccgcg gtgcgggggg gctgcgaggg gaacaaaggc tgcgtgcggg gtgtgtgcgt  1020
gggggggtga gcaggggggtg tgggcgcggc ggtcgggctg taaccccccc ctgcacccccc 1080 ctccccgagt tgctgagcac ggcccggctt cgggtgcggg gctccgtgcg gggcgtggcg  1140
cggggctcgc cgtgccgggc gggggggtggc ggcaggtggg ggtgccgggc ggggcggggc  1200
cgcctcgggc cggggagggc tcggggggagg ggcgcggcgg ccccggagcg ccggcggctg  1260
```

```
tcgaggcgcg gcgagccgca gccattgcct tttatggtaa tcgtgcgaga gggcgcaggg    1320
acttcctttg tcccaaatct ggcggagccg aaatctggga ggcgccgccg cacccctct     1380 agcgggcgcg ggcgaagcgg tgcggcgccg gcaggaagga aatgggcggg gagggccttc    1440
gtgcgtcgcc gcgccgccgt ccccttctcc atctccagcc tcggggctgc cgcaggggga    1500
cggctgcctt cggggggggac ggggcagggc ggggttcggc ttctggcgtg tgaccggcgg   1560
ggtttatatc ttcccttctc tgttcctccg cagccagccg gatcc                    1605
```

<210> SEQ ID NO 63
<211> LENGTH: 1670
<212> TYPE: DNA
<213> ORGANISM: Artificial Sequence
<220> FEATURE:
<223> OTHER INFORMATION: chimeric gene regulatory unit

<400> SEQUENCE: 63

```
acgcgttgac attgattatt gagtagttat taatagtaat caattacggg gtcattagtt      60
catagcccat atatggagtt ccgcgttaca aacttacgg taaatggccc gcctggctga     120
ccgcccaacg accccgccc attgacgtca ataatgacgt atgttcccat agtaacgcca     180
atagggactt tccattgacg tcaatgggtg gagtattac ggtaaactgc ccacttggca     240
gtacatcaag tgtatcatat gccaagtccg cccctattg acgtcaatga cggtaaatgg    300
cccgcctggc attatgccca gtacatgacc ttacgggact ttcctacttg gcagtacatc   360
tacgtattag tcatcgctat tacactagtt cgaggtgagc cccacgttct gcttcactct   420
ccccatctcc cccctccc cacccccaat tttgtattta tttttttt aattatttttg       480 tgcagcgatg ggggcggggg gggggggggc gcgcgccagg cggggcgggg cgggcgagg    540 ggcggggcgg ggcgaggcgg agaggtgcgg cggcagccaa tcagagcggc gcgctccgaa   600
agtttccttt tatggcgagg cggcggcggc ggcggcccta taaaaagcga agcgcgcggc    660
gggcgggagt cgctgcgttg ccttcgcccc gtgccccgct ccgcgccgcc tcgcgccgcc   720
cgccccggct ctgactgacc gcgttactcc cacaggtgag cgggcgggac ggcccttctc   780
ctccgggctg taattagcgc ttggtttaat gacggctcgt ttcttttctg tggctgcgtg   840
aaagccttaa agggctccgg gagggccctt tgtgcggggg ggagcggctc ggggggtgcg    900
tgcgtgtgtg tgtgcgtggg gagcgccgcg tgcggcccgc gctgcccggc ggctgtgagc    960
gctgcgggcg cggcgcgggg ctttgtgcgc tccgcgtgtg cgcgagggga gcgcggccgg   1020
gggcggtgcc ccgcggtgcg ggggggctgc gaggggaaca aaggctgcgt gcgggtgtg    1080 tgcgtggggg ggtgagcagg gggtgtgggc gcggcggtcg ggctgtaacc cccccctgca   1140
cccccctccc cgagttgctg agcacggccc ggcttcgggt gcggggctcc gtgcggggcg   1200
tggcgcgggg ctcgccgtgc cgggcggggg gtggcggcag gtgggggtgc cgggcggggc    1260
ggggccgcct cgggccgggg agggctcggg ggaggggcgc ggcggcccg gagcgccggc    1320 ggctgtcgag gcgcggcgag ccgcagccat tgccttttat ggtaatcgtg cgagagggcg   1380
cagggacttc ctttgtccca aatctggcgg agccgaaatc tgggaggcgc cgccgcaccc   1440
cctctagcgg gcgcgggcga gcggtgcgg cgccggcagg aaggaaatgg gcgggagggg   1500
ccttcgtgcg tcgccgcgcc gccgtcccct tctccatctc cagcctcggg gctgccgcag   1560
ggggacggct gccttcgggg gggacgggc agggcggggt tcggcttctg gcgtgtgacc    1620 ggcgggtt atatcttccc ttctctgttc ctccgcagcc agccggatcc                 1670
```

<210> SEQ ID NO 64
<211> LENGTH: 1726
<212> TYPE: DNA
<213> ORGANISM: Artificial Sequence
<220> FEATURE:
<223> OTHER INFORMATION: chimeric gene regulatory unit

<400> SEQUENCE: 64

```
acgcgtagtc aatgggaaaa acccattgga gccaagtaca ctgactcaat agggactttc      60
cattgggttt tgcccagtac ataaggtcaa tagggggtga gtcaacagga aagtcccatt     120
ggagccaagt acattgagtc aatagggact ttccaatggg ttttgcccag tacataaggt     180
caatgggagg taagccaatg ggttttcccc attactggca cgtatactga gtcattaggg     240
actttccaat gggttttgcc cagtacataa ggtcaatagg ggtgaatcaa caggaaagtc     300
ccattggagc caagtacact gagtcaatag ggactttcca ttgggttttg cccagtacaa     360
aaggtcaata gggggtgagt caatgggttt ttcccattat tggcacgtac ataaggtcaa     420
tagggggtgag tcattgggtt tttccagcca atttaattaa aacgccatgt actttcccac     480
cattgacgtc aatgggctat tgaaactaat gcaacgtgac ctttaaacgg tactttccca     540
tagctgatta atgggaaagt accgttctcg agccaataca cgtcaatggg aagtgaaagg     600
gcagccaaaa cgtaacaccg ccccggtttt ccctggaaat tccatattgg cacgcattct     660
attggctgag ctgcgttcac gtgggtataa gaggcgcgac cagcgtcggt accgcggccg     720
cggagtcgct gcgttgcctt cgccccgtgc cccgctccgc gccgcctcgc gccgcccgcc     780
ccggctctga ctgaccgcgt tactcccaca ggtgagcggg cggacgcc cttctcctcc     840
gggctgtaat tagcgcttgg tttaatgacg gctcgtttct tttctgtggc tgcgtgaaag     900
ccttaaaggg ctccgggagg gccctttgtg cgggggggag cggctcgggg ggtgcgtgcg     960
tgtgtgtgtg cgtggggagc gccgcgtgcg gcccgcgctg cccggcggct gtgagcgctg    1020
cgggcgcggc gcggggcttt gtgcgctccg cgtgtgcgcg aggggagcgc ggccggggc    1080
ggtgccccgc ggtgcggggg ggctgcgagg ggaacaaagg ctgcgtgcgg ggtgtgtgcg    1140
tgggggggtg agcaggggt gtgggcgcgg cggtcgggct gtaaccccc cctgcacccc    1200
cctccccgag ttgctgagca cggcccggct tcgggtgcgg ggctccgtgc ggggcgtggc    1260
gcggggctcg ccgtgccggg cggggggtgg cggcaggtgg gggtgccggg cggggcgggg    1320
ccgcctcggg ccggggaggg ctcggggag gggcgcggcg gccccggagc gccggcggct    1380
gtcgaggcgc ggcgagccgc agccattgcc ttttatggta atcgtgcgag agggcgcagg    1440
gacttccttt gtcccaaatc tggcggagcc gaaatctggg aggcgccgcc gcaccccctc    1500
tagcgggcgc gggcgaagcg gtgcggcgcc ggcaggaagg aaatgggcgg ggagggcctt    1560
cgtgcgtcgc gcgccgccg tccccttctc catctccagc ctcggggctg ccgcaggggg    1620
acggctgcct tcgggggga cggggcaggg cggggttcgg cttctggcgt gtgaccggcg    1680
ggtttatat cttcccttct ctgttcctcc gcagccagcc ggatcc              1726
```

<210> SEQ ID NO 65
<211> LENGTH: 1669
<212> TYPE: DNA
<213> ORGANISM: Artificial Sequence
<220> FEATURE:
<223> OTHER INFORMATION: chimeric gene regulatory unit

<400> SEQUENCE: 65

```
acgcgtagtc aatgggaaaa acccattgga gccaagtaca ctgactcaat agggactttc      60
```

```
cattgggttt tgcccagtac ataaggtcaa tagggggtga gtcaacagga aagtcccatt      120
ggagccaagt acattgagtc aatagggact ttccaatggg ttttgcccag tacataaggt      180
caatgggagg taagccaatg ggttttcccc attactggca cgtatactga gtcattaggg      240
actttccaat gggttttgcc cagtacataa ggtcaatagg ggtgaatcaa caggaaagtc      300
ccattggagc caagtacact gagtcaatag ggactttcca ttgggttttg cccagtacaa      360
aaggtcaata gggggtgagt caatgggttt ttcccattat tggcacgtac ataaggtcaa      420 tagggggtgac tagtcatggt gatgcggttt tggcagtaca ccaatgggcg tggatagcgg      480
tttgactcac ggggatttcc aagtctccac cccattgacg tcaatgggag tttgttttgg      540
caccaaaatc aacgggactt tccaaaatgt cgtaataacc ccgccccgtt gacgcaaatg      600
ggcggtaggc gtgtacggtg ggaggtctat ataagcagag ctcgtttagt gaaccggcgg      660
ccgcggagtc gctgcgttgc cttcgccccg tgccccgctc cgcgccgcct cgcgccgccc      720
gccccggctc tgactgaccg cgttactccc acaggtgagc gggcgggacg cccttctcc       780 tccgggctgt aattagcgct tggtttaatg acggctcgtt tcttttctgt ggctgcgtga      840
aagccttaaa gggctccggg agggcccttt gtgcgggggg gagcggctcg ggggggtgcgt     900 gcgtgtgtgt gtgcgtgggg agcgccgcgt gcggcccgcg ctgcccggcg gctgtgagcg     960
ctgcgggcgc ggcgcgggc tttgtgcgct ccgcgtgtgc gcgaggggag cgcggccggg     1020
ggcggtgccc cgcggtgcgg gggggctgcg aggggaacaa aggctgcgtg cggggtgtgt    1080
gcgtgggggg gtgagcaggg ggtgtgggcg cggcggtcgg gctgtaaccc cccctgcac     1140 cccccctcccc gagttgctga gcacggcccg gcttcgggtg cggggctccg tgcggggcgt    1200 ggcgcgggc tcgccgtgcc gggcgggggg tggcggcagg tggggtgcc gggcggggcg      1260 gggccgcctc gggccgggga gggctcgggg gaggggcgcg gcgcccccgg agcgccggcg    1320
gctgtcgagg cgcggcgagc cgcagccatt gcctttatg gtaatcgtgc gagagggcgc    1380
agggacttcc tttgtcccaa atctggcgga gccgaaatct gggaggcgcc gccgcacccc    1440
ctctagcggg cgcgggcgaa gcggtgcggc gccggcagga aggaaatggg cggggagggc    1500
cttcgtgcgt cgccgcgccg ccgtcccctt ctccatctcc agcctcgggg ctgccgcagg    1560
gggacggctg ccttcggggg ggacggggca gggcggggtt cggcttctgg cgtgtgaccg    1620
gcggggttta tatcttcccct ctctgttcc tccgcagcca gccggatcc                1669
```

<210> SEQ ID NO 66
<211> LENGTH: 1556
<212> TYPE: DNA
<213> ORGANISM: Artificial Sequence
<220> FEATURE:
<223> OTHER INFORMATION: chimeric gene regulatory unit

<400> SEQUENCE: 66

```
acgcgtagtc aatgggaaaa acccattgga gccaagtaca ctgactcaat agggactttc       60
cattgggttt tgcccagtac ataaggtcaa tagggggtga gtcaacagga aagtcccatt      120
ggagccaagt acattgagtc aatagggact ttccaatggg ttttgcccag tacataaggt      180
caatgggagg taagccaatg ggttttcccc attactggca cgtatactga gtcattaggg      240
actttccaat gggttttgcc cagtacataa ggtcaatagg ggtgaatcaa caggaaagtc      300
ccattggagc caagtacact gagtcaatag ggactttcca ttgggttttg cccagtacaa      360
aaggtcaata gggggtgagt caatgggttt ttcccattat tggcacgtac ataaggtcaa      420
```

```
tagggggtgac tagttcccgc ccctaactcc gcccatcccg cccctaactc cgcccagttc    480
cgcccattct ccgccccatg gctgactaat tttttttatt tatgcagagg ccgaggccgc    540
ctcgcggccg cggagtcgct gcgttgcctt cgccccgtgc cccgctccgc gccgcctcgc    600
gccgcccgcc ccggctctga ctgaccgcgt tactcccaca ggtgagcggg cgggacggcc    660
cttctcctcc gggctgtaat tagcgcttgg tttaatgacg gctcgtttct tttctgtggc    720
tgcgtgaaag ccttaaaggg ctccgggagg gcccttttgtg cggggggggag cggctcgggg   780 ggtgcgtgcg tgtgtgtgtg cgtggggagc gccgcgtgcg gccgcgctg cccggcggct    840 gtgagcgctg cgggcgcggc gcggggcttt gtgcgctccg cgtgtgcgcg aggggagcgc    900
ggccgggggc ggtgccccgc ggtgcgggg ggctgcgagg ggaacaaagg ctgcgtgcgg    960
ggtgtgtgcg tgggggggtg agcagggggt gtgggcgcgg cggtcgggct gtaacccccc   1020
cctgcacccc cctccccgag ttgctgagca cggcccggct tcgggtgcgg ggctccgtgc   1080
ggggcgtggc gcggggctcg ccgtgccggg cgggggtgg cggcaggtgg gggtgccggg    1140
cggggcgggg ccgcctcggg ccggggaggg ctcggggag gggcgcggcg gccccggagc    1200
gccggcggct gtcgaggcgc ggcgagccga agccattgcc ttttatggta atcgtgcgag   1260
agggcgcagg gacttccttt gtcccaaatc tggcggagcc gaaatctggg aggcgccgcc   1320 gcacccctc tagcgggcgc gggcgaagcg gtgcggcgcc ggcaggaagg aaatgggcgg   1380
ggagggcctt cgtgcgtcgc cgcgccgcg tccccttctc catctccagc ctcggggctg   1440
ccgcaggggg acggctgcct tcgggggga cggggcaggg cggggttcgg cttctggcgt   1500
gtgaccggcg ggtttatat cttcccttct ctgttcctcc gcagccagcc ggatcc       1556
```

<210> SEQ ID NO 67
<211> LENGTH: 1650
<212> TYPE: DNA
<213> ORGANISM: Artificial Sequence
<220> FEATURE:
<223> OTHER INFORMATION: chimeric gene regulatory unit

<400> SEQUENCE: 67

```
acgcgtagtc aatgggaaaa acccattgga gccaagtaca ctgactcaat agggactttc     60
cattgggttt tgcccagtac ataaggtcaa taggggtgac gtcaacagga aagtcccatt    120
ggagccaagt acattgagtc aatagggact ttccaatggg ttttgccag tacataaggt    180 caatgggagg taagccaatg ggttttttccc attactggca cgtatactga gtcattaggg   240
actttccaat gggttttgcc cagtacataa ggtcaatagg ggtgaatcaa caggaaagtc    300
ccattggagc caagtacact gagtcaatag ggactttcca ttgggttttg cccagtacaa    360
aaggtcaata gggggtgagt caatgggttt tcccattat tggcacgtac ataaggtcaa    420 tagggggtgac tagtcgtgag gctccggtgc ccgtcagtgg gcagagcgca catcgcccac   480
agtccccgag aagttggggg gagggtcgg caattgaacc ggtgcctaga gaaggtggcg    540
cggggtaaac tgggaaagtg atgtcgtgta ctggctccgc cttttttcccg agggtggggg    600 agaaccgtat ataagtgcag tagtcgccgt gaacgttgcg gccgcggagt cgctgcgttg    660
ccttcgcccc gtgccccgct ccgcgccgcc tcgcgccgcc cgcccggct ctgactgacc    720 gcgttactcc cacaggtgag cgggcggac ggcccttctc ctccgggctg taattagcgc    780 ttggttttaat gacggctcgt ttcttttctg tggctgcgtg aaagccttaa agggctccgg    840
gagggccctt tgtgcgggg ggagcggctc ggggggtgcg tgcgtgtgtg tgcgtgggg    900 gagcgccgcg tgcggcccgc gctgcccggc ggctgtgagc gctgcgggcg cggcgcgggg   960
```

```
ctttgtgcgc tccgcgtgtg cgcgagggga gcgcggccgg gggcggtgcc ccgcggtgcg    1020
ggggggctgc gaggggaaca aaggctgcgt gcggggtgtg tgcgtggggg ggtgagcagg    1080
gggtgtgggc gcggcggtcg ggctgtaacc ccccccctgca ccccccctccc cgagttgctg  1140 agcacggccc ggcttcgggt gcgggctcc gtgcggggcg tggcgcgggg ctcgccgtgc     1200
cgggcggggg gtggcggcag gtggggtgc cgggcggggc ggggccgcct cgggccgggg     1260
agggctcggg ggaggggcgc ggcggccccg gagcgccggc ggctgtcgag gcgcggcgag    1320
ccgcagccat tgccttttat ggtaatcgtg cgagagggcg cagggacttc ctttgtccca    1380
aatctggcgg agccgaaatc tgggaggcgc cgccgcaccc cctctagcgg gcgcgggcga    1440
agcggtgcgg cgccggcagg aaggaaatgg gcggggaggg ccttcgtgcg tcgccgcgcc    1500
gccgtcccct tctccatctc cagcctcggg gctgccgcag ggggacggct gccttcgggg    1560
gggacggggc agggcggggt tcggcttctg gcgtgtgacc ggcggggttt atatcttccc    1620
ttctctgttc ctccgcagcc agccggatcc                                     1650

<210> SEQ ID NO 68
<211> LENGTH: 1715
<212> TYPE: DNA
<213> ORGANISM: Artificial Sequence
<220> FEATURE:
<223> OTHER INFORMATION: chimeric gene regulatory unit

<400> SEQUENCE: 68
acgcgtagtc aatgggaaaa acccattgga gccaagtaca ctgactcaat agggactttc      60
cattgggttt tgcccagtac ataaggtcaa taggggtga gtcaacagga aagtcccatt      120
ggagccaagt acattgagtc aatagggact ttccaatggg ttttgcccag tacataaggt      180
caatgggagg taagccaatg ggttttccc attactggca cgtatactga gtcattaggg      240
actttccaat gggttttgcc cagtacataa ggtcaatagg ggtgaatcaa caggaaagtc      300
ccattggagc caagtacact gagtcaatag ggactttcca ttgggttttg cccagtacaa      360 aggtcaata gggggtgagt caatgggttt ttcccattat ggcacgtac ataaggtcaa       420 tagggggtgac tagttcgagg tgagccccac gttctgcttc actctcccca tctcccccc     480 ctccccaccc ccaattttgt atttatttat ttttaatta ttttgtgcag cgatgggggc     540
gggggggggg ggggcgcgcg ccaggcgggg cgggcgggg cgaggggcgg ggcggggcga      600
ggcggagagg tgcggcggca gccaatcaga gcggcgcgct ccgaaagttt cctttttatgg    660 cgaggcggcg gcgcggcgg ccctataaaa agcgaagcgc gcggcgggcg ggagtcgctg      720
cgttgccttc gccccgtgcc ccgctccgcg ccgcctcgcg ccgcccgccc ggctctgac     780 tgaccgcgtt actccacag gtgagcgggc gggacgccc ttctcctccg ggctgtaatt      840
agcgcttggt ttaatgacgg ctcgtttctt ttctgtggct gcgtgaaagc cttaagggc     900 tccgggaggg cccttttgtgc gggggggagc ggctcggggg gtgcgtgcgt gtgtgtgtgc    960
gtggggagcg ccgcgtgcgg cccgcgctgc ccggcggctg tgagcgctgc gggcgcggcg    1020 cgggctttg tgcgctccgc gtgtgcgcga ggggagcgcg gccggggcg gtgcccgcg       1080 gtgcggggg gctgcgaggg gaacaaaggc tgcgtgcggg gtgtgtgcgt ggggggggtga    1140 gcagggggtg tgggcgcggc ggtcggctg taaccccccc ctgcaccccc ctccccgagt     1200
tgctgagcac ggcccggctt cgggtgcggg gctccgtgcg gggcgtggcg cggggctcgc    1260
cgtgccgggc gggggtgc ggcaggtggg ggtgccgggc ggggcgggc cgcctcgggc       1320
```

-continued

```
cggggagggc tcggggagg ggcgcggcgg ccccggagcg ccggcggctg tcgaggcgcg    1380
gcgagccgca gccattgcct tttatggtaa tcgtgcgaga gggcgcaggg acttcctttg   1440
tcccaaatct ggcggagccg aaatctggga ggcgccgccg cacccctct agcgggcgcg    1500 ggcgaagcgg tgcggcgccg gcaggaagga aatgggcggg gagggccttc gtgcgtcgcc   1560
gcgccgccgt ccccttctcc atctccagcc tcggggctgc cgcaggggga cggctgcctt   1620 cggggggggac ggggcaggc ggggttcggc ttctggcgtg tgaccggcgg ggtttatatc   1680
ttcccttctc tgttcctccg cagccagccg gatcc                              1715
```

<210> SEQ ID NO 69
<211> LENGTH: 1296
<212> TYPE: DNA
<213> ORGANISM: Artificial Sequence
<220> FEATURE:
<223> OTHER INFORMATION: chimeric gene regulatory unit

<400> SEQUENCE: 69

```
acgcgttgtg gaatgtgtgt cagttagggt gtggaaagtc cccaggctcc ccagcaggca     60
gaagtatgca aagcatgcat ctcaattagt cagcaaccag gtgtggaaag tccccaggct    120
ccccagcagg cagaagtatg caaagcatgc atctcaatta gtcagcaacc atagtccccg    180
ccctaactcc gcccatcccg cccctaactc cgcccagttc cgcccattct ccgccccatg    240
gctgactaat ttttttatt tatgcagagg ccgaggccgc ctcgcggccg cggagtcgct    300
gcgttgcctt cgccccgtgc cccgctccgc gccgcctcgc gccgcccgcc ccggctctga    360
ctgaccgcgt tactcccaca ggtgagcggg cgggacggcc cttctcctcc gggctgtaat    420
tagcgcttgg tttaatgacg gctcgtttct tttctgtggc tgcgtgaaag ccttaaaggg    480 ctccggggagg gcccttttgtg cgggggggag cggctcgggg ggtgcgtgcg tgtgtgtgtg    540
cgtggggagc gccgcgtgcg gcccgcgctg ccggcggct gtgagcgctg cgggcgcggc    600
gcggggcttt gtgcgctccg cgtgtgcgcg agggagcgc ggccggggc ggtgccccgc    660 ggtgcggggg ggctgcgagg ggaacaaagg ctgcgtgcgg ggtgtgtgcg tggggggtg    720 agcagggggt gtgggcgcgg cggtcgggct gtaaccccccc cctgcacccc ctccccgag    780 ttgctgagca cggcccggct tcgggtgcgg ggctccgtgc ggggcgtggc gcgggctcg    840 ccgtgccggg cggggggtgg cggcaggtgg gggtgccggg cggggcgggg ccgcctcggg    900
ccggggaggg ctcggggggag gggcgcggcg gcccggagc gccggcggct gtcgaggcgc    960
ggcgagccgc agccattgcc ttttatggta atcgtgcgag agggcgcagg gacttccttt   1020
gtcccaaatc tggcggagcc gaaatctggg aggcgccgcc gcacccctc tagcgggcg    1080 gggcgaagcg gtgcggcgcc ggcaggaagg aaatgggcgg ggagggcctt cgtgcgtcgc   1140
cgcgccgccg tccccttctc catctccagc ctcggggctg ccgcaggggg acggctgcct   1200 tcgggggggga cggggcaggg cggggttcgg cttctggcgt tgaccggcg ggtttatat    1260 cttcccttct ctgttcctcc gcagccagcc ggatcc                             1296
```

<210> SEQ ID NO 70
<211> LENGTH: 1416
<212> TYPE: DNA
<213> ORGANISM: Artificial Sequence
<220> FEATURE:
<223> OTHER INFORMATION: chimeric gene regulatory unit

<400> SEQUENCE: 70

```
acgcgttgtg gaatgtgtgt cagttagggt gtggaaagtc cccaggctcc ccagcaggca     60
```

```
gaagtatgca aagcatgcat ctcaattagt cagcaaccag gtgtggaaag tccccaggct    120
ccccagcagg cagaagtatg caaagcatgc atctcaatta gtcagcaacc atagactagt    180
catggtgatg cggttttggc agtacaccaa tgggcgtgga tagcggtttg actcacgggg    240
atttccaagt ctccacccca ttgacgtcaa tgggagtttg ttttggcacc aaaatcaacg    300
ggactttcca aaatgtcgta ataaccccgc cccgttgacg caaatgggcg gtaggcgtgt    360
acggtgggag gtctatataa gcagagctcg tttagtgaac cgtgcggccg cggagtcgct    420
gcgttgcctt cgccccgtgc cccgctccgc gccgcctcgc gccgcccgcc ccggctctga    480
ctgaccgcgt tactcccaca ggtgagcggg cgggacggcc cttctcctcc gggctgtaat    540
tagcgcttgg tttaatgacg gctcgtttct tttctgtggc tgcgtgaaag ccttaaaggg    600
ctccgggagg gccctttgtg cggggggggag cggctcgggg ggtgcgtgcg tgtgtgtgtg    660
cgtggggagc gccgcgtgcg gcccgcgctg cccggcggct gtgagcgctg cgggcgcggc    720
gcggggcttt gtgcgctccg cgtgtgcgcg aggggagcgc ggccggggc ggtgccccgc    780 ggtgcggggg ggctgcgagg ggaacaaagg ctgcgtgcgg ggtgtgtgcg tggggggtg    840 agcaggggg gtgggcgcgg cggtcgggct gtaaccccc cctgcacccc cctccccgag    900
ttgctgagca cggcccggct tcgggtgcgg ggctccgtgc gggggcgtggc gcggggctcg    960 ccgtgccggg cggggggtgg cggcaggtgg gggtgccggg cggggcgggg ccgcctcggg   1020
ccggggaggg ctcggggggag gggcgcggcg gccccggagc gccggcggct gtcgaggcgc   1080
ggcgagccgc agccattgcc ttttatggta atcgtgcgag agggcgcagg gacttccttt   1140
gtcccaaatc tggcggagcc gaaatctggg aggcgccgcc gcaccccctc tagcgggcgc   1200
gggcgaagcg gtgcggcgcc ggcaggaagg aaatgggcgg ggagggcctt cgtgcgtcgc   1260
cgcgccgccg tccccttctc catctccagc ctcggggctg ccgcagggg acggctgcct   1320 tcgggggga cggggcaggg cggggttcgg cttctggcgt gtgaccggcg gggtttatat   1380
cttcccttct ctgttcctcc gcagccagcc ggatcc                            1416
```

<210> SEQ ID NO 71
<211> LENGTH: 1478
<212> TYPE: DNA
<213> ORGANISM: Artificial Sequence
<220> FEATURE:
<223> OTHER INFORMATION: chimeric gene regulatory unit

<400> SEQUENCE: 71

```
acgcgttgtg gaatgtgtgt cagttagggt gtggaaagtc cccaggctcc ccagcaggca     60
gaagtatgca aagcatgcat ctcaattagt cagcaaccag gtgtggaaag tccccaggct    120
ccccagcagg cagaagtatg caaagcatgc atctcaatta gtcagcaacc atagactagt    180
agtcattggg ttttccagc caatttaatt aaaacgccat gtactttccc accattgacg    240
tcaatgggct attgaaacta atgcaacgtg acctttaaac ggtactttcc catagctgat    300
taatgggaaa gtaccgttct cgagccaata cacgtcaatg ggaagtgaaa gggcagccaa    360
aacgtaacac cgccccggtt ttccctggaa attccatatt ggcacgcatt ctattggctg    420
agctgcgttc acgtgggtat aagaggcgcg accagcgtcg gtaccgcggc gcggagtcg    480 ctgcgttgcc ttcgccccgt gccccgctcc gccgcctc gccgcccg cccggctct    540 gactgaccgc gttactccca caggtgagcg ggcgggacgg cccttctcct ccgggctgta    600
attagcgctt ggtttaatga cggctcgttt cttttctgtg gctgcgtgaa agccttaaag    660
```

```
ggctccggga gggccctttg tgcggggggg agcggctcgg ggggtgcgtg cgtgtgtgtg      720
tgcgtgggga gcgccgcgtg cggcccgcgc tgcccggcgg ctgtgagcgc tgcgggcgcg      780
gcgcggggct ttgtgcgctc cgcgtgtgcg cgaggggagc gcggccgggg gcggtgcccc      840
gcggtgcggg ggggctgcga ggggaacaaa ggctgcgtgc ggggtgtgtg cgtggggggg      900
tgagcagggg gtgtgggcgc ggcggtcggg ctgtaacccc cccctgcacc cccctccccg      960
agttgctgag cacggcccgg cttcgggtgc ggggctccgt gcggggcgtg gcgcggggct     1020
cgccgtgccg ggcggggggt ggcggcaggt ggggtgccg gcggggcgg gccgcctcg      1080 ggccggggag ggctcggggg aggggcgcgg cggcccgga gcgccggcgg ctgtcgaggc      1140
gcggcgagcc gcagccattg cctttatgg taatcgtgcg agagggcgca gggacttcct      1200
ttgtcccaaa tctggcggag ccgaaatctg ggaggcgccg ccgcacccc tctagcgggc      1260 gcgggcgaag cggtgcggcg ccggcaggaa ggaaatgggc ggggagggcc ttcgtgcgtc      1320
gccgcgccgc cgtccccttc tccatctcca gcctcgggc tgccgcaggg ggacggctgc      1380
cttcgggggg gacggggcag ggcggggttc ggcttctggc gtgtgaccgg cggggtttat      1440
atcttccctt ctctgttcct ccgcagccag ccggatcc                            1478

<210> SEQ ID NO 72
<211> LENGTH: 1396
<212> TYPE: DNA
<213> ORGANISM: Artificial Sequence
<220> FEATURE:
<223> OTHER INFORMATION: chimeric gene regulatory unit

<400> SEQUENCE: 72
acgcgttgtg gaatgtgtgt cagttagggt gtggaaagtc cccaggctcc ccagcaggca       60
gaagtatgca aagcatgcat ctcaattagt cagcaaccag gtgtggaaag tccccaggct      120
ccccagcagg cagaagtatg caaagcatgc atctcaatta gtcagcaacc atagactagt      180
cgtgaggctc cggtgccgt cagtgggcag agcgcacatc gcccacagtc cccgagaagt      240 tgggggagg ggtcggcaat tgaaccggtg cctagagaag gtggcgcggg gtaaactggg      300
aaagtgatgt cgtgtactgg ctccgccttt ttcccgaggg tggggagaa ccgtatataa      360 gtgcagtagt cgccgtgaac gttgcggccg cggagtcgct gcgttgcctt cgccccgtgc      420
cccgctccgc gccgcctcgc gccgcccgcc ccggctctga ctgaccgcgt tactcccaca      480
ggtgagcggg cgggacggcc cttctcctcc gggctgtaat tagcgcttgg tttaatgacg      540
gctcgtttct tttctgtggc tgcgtgaaag ccttaaaggg ctccgggagg gcccttttgtg      600 cggggggag cggctcgggg ggtgcgtgcg tgtgtgtgtg cgtggggagc gccgcgtgcg      660
gcccgcgctg cccggcggct gtgagcgctg cgggcgcggc gcggggcttt gtgcgctccg      720
cgtgtgcgcg aggggagcgc ggccggggc ggtgccccgc ggtgcggggg ggctgcgagg      780
ggaacaaagg ctgcgtgcgg ggtgtgtgcg tggggggtg agcaggggt gtgggcgcgg      840 cggtcgggct gtaacccccc cctgcacccc cctccccgag ttgctgagca cggcccggct      900
tcgggtgcgg ggctccgtgc ggggcgtggc gcggggctcg ccgtgccggg cggggggtgg      960
cggcaggtgg gggtgccggg cggggcgggg ccgcctcggg ccggggaggg ctcggggag     1020 gggcgcggcg gcccggagc gccggcggct gtcgaggcgc ggcgagccgc agccattgcc      1080
ttttatggta atcgtgcgag agggcgcagg gacttccttt gtcccaaatc tggcggagcc      1140
gaaatctgga ggcgccgcc gcaccccctc tagcgggcgc gggcgaagcg gtgcggcgcc      1200
ggcaggaagg aaatgggcgg ggagggcctt cgtgcgtcgc cgcgccgccg tccccttctc      1260
```

```
catctccagc ctcggggctg ccgcaggggg acggctgcct tcggggggga cggggcaggg     1320
cggggttcgg cttctggcgt gtgaccggcg gggtttatat cttcccttct ctgttcctcc     1380
gcagccagcc ggatcc                                                    1396

<210> SEQ ID NO 73
<211> LENGTH: 1461
<212> TYPE: DNA
<213> ORGANISM: Artificial Sequence
<220> FEATURE:
<223> OTHER INFORMATION: chimeric gene regulatory unit

<400> SEQUENCE: 73
acgcgttgtg gaatgtgtgt cagttagggt gtggaaagtc cccaggctcc ccagcaggca      60
gaagtatgca aagcatgcat ctcaattagt cagcaaccag gtgtggaaag tccccaggct     120
ccccagcagg cagaagtatg caaagcatgc atctcaatta gtcagcaacc atagactagt     180
tcgaggtgag ccccacgttc tgcttcactc tccccatctc ccccccctcc caccccccaa     240
ttttgtattt atttattttt taattatttt gtgcagcgat ggggggcgggg gggggggggg     300 cgcgcgccag gcggggcggg gcggggcgag gggcggggcg gggcgaggcg gagaggtgcg     360
gcggcagcca atcagagcgg cgcgctccga aagtttcctt ttatggcgag gcggcggcgg     420
cggcggccct ataaaagcg aagcgcgcgg cgggcgggag tcgctgcgtt gccttcgccc     480
cgtgccccgc tccgcgccgc ctcgcgccgc ccgccccggc tctgactgac cgcgttactc     540
ccacaggtga gcgggcggga cggcccttct cctccgggct gtaattagcg cttggtttaa     600
tgacggctcg tttcttttct gtggctgcgt gaaagcctta aagggctccg ggagggccct     660
ttgtgcgggg gggagcggct cgggggggtgc gtgcgtgtgt gtgtgcgtgg ggagcgccgc     720
gtgcggcccg cgctgcccgg cggctgtgag cgctgcgggc gcggcgcggg gctttgtgcg     780
ctccgcgtgt gcgcgagggg agcgcggccg ggggcggtgc cccgcggtgc gggggggctg     840 cgagggggaac aaaggctgcg tgcggggtgt gtgcgtgggg gggtgagcag ggggtgtggg     900
cgcggcggtc gggctgtaac cccccccctgc accccctcc ccgagttgct gagcacggcc     960
cggcttcggg tgcggggctc cgtgcggggc gtggcgcggg gctcgccgtg ccggggcgggg    1020 ggtggcggca ggtgggggtg ccggcgggg cggggccgcc tcgggccggg gagggctcgg    1080 gggagggcg cggcggcccc ggagcgccgg cggctgtcga ggcgcggcga gccgcagcca    1140 ttgccttta tggtaatcgt gcgagagggc gcagggactt cctttgtccc aaatctggcg    1200
gagccgaaat ctgggaggcg ccgccgcacc ccctctagcg ggcgcgggcg aagcggtgcg    1260
gcgccggcag gaaggaaatg ggcggggagg gccttcgtgc gtcgccgcgc cgccgtcccc    1320
ttctccatct ccagcctcgg ggctgccgca gggggacggc tgccttcggg ggggacgggg    1380
cagggcgggg ttcggcttct ggcgtgtgac cggcggggtt tatatcttcc cttctctgtt    1440
cctccgcagc cagccggatc c                                              1461

<210> SEQ ID NO 74
<211> LENGTH: 737
<212> TYPE: PRT
<213> ORGANISM: Homo sapiens

<400> SEQUENCE: 74

Met Ser Asp Gln Asp His Ser Met Asp Glu Met Thr Ala Val Val Lys
1               5                   10                  15

Ile Glu Lys Gly Val Gly Gly Asn Asn Gly Gly Asn Gly Asn Gly Gly
```

```
                    20                  25                  30
Gly Ala Phe Ser Gln Ala Arg Ser Ser Thr Gly Ser Ser Ser Ser
                35                  40                  45
Thr Gly Gly Gly Gln Gly Ala Asn Gly Trp Gln Ile Ile Ser Ser
                50                  55                  60
Ser Ser Gly Ala Thr Pro Thr Ser Lys Glu Gln Ser Gly Ser Thr
65                  70                  75                  80
Asn Gly Ser Asn Gly Ser Glu Ser Ser Lys Asn Arg Thr Val Ser Gly
                    85                  90                  95
Gly Gln Tyr Val Val Ala Ala Pro Asn Leu Gln Asn Gln Gln Val
                100                 105                 110
Leu Thr Gly Leu Pro Gly Val Met Pro Asn Ile Gln Tyr Gln Val Ile
                    115                 120                 125
Pro Gln Phe Gln Thr Val Asp Gly Gln Gln Leu Gln Phe Ala Ala Thr
                    130                 135                 140
Gly Ala Gln Val Gln Gln Asp Gly Ser Gly Gln Ile Gln Ile Pro
145                 150                 155                 160
Gly Ala Asn Gln Gln Ile Ile Thr Asn Arg Gly Ser Gly Asn Ile
                165                 170                 175
Ile Ala Ala Met Pro Asn Leu Leu Gln Gln Ala Val Pro Leu Gln Gly
                    180                 185                 190
Leu Ala Asn Asn Val Leu Ser Gly Gln Thr Gln Tyr Val Thr Asn Val
                    195                 200                 205
Pro Val Ala Leu Asn Gly Asn Ile Thr Leu Leu Pro Val Asn Ser Val
                    210                 215                 220
Ser Ala Ala Thr Leu Thr Pro Ser Ser Gln Ala Val Thr Ile Ser Ser
225                 230                 235                 240
Ser Gly Ser Gln Glu Ser Gly Ser Gln Pro Val Thr Ser Gly Thr Thr
                    245                 250                 255
Ile Ser Ser Ala Ser Leu Val Ser Ser Gln Ala Ser Ser Ser Ser Phe
                260                 265                 270
Phe Thr Asn Ala Asn Ser Tyr Ser Thr Thr Thr Thr Ser Asn Met
                275                 280                 285
Gly Ile Met Asn Phe Thr Thr Ser Gly Ser Ser Gly Thr Asn Ser Gln
                    290                 295                 300
Gly Gln Thr Pro Gln Arg Val Ser Gly Leu Gln Gly Ser Asp Ala Leu
305                 310                 315                 320
Asn Ile Gln Gln Asn Gln Thr Ser Gly Gly Ser Leu Gln Ala Gly Gln
                    325                 330                 335
Gln Lys Glu Gly Glu Gln Asn Gln Gln Thr Gln Gln Gln Gln Ile Leu
                    340                 345                 350
Ile Gln Pro Gln Leu Val Gln Gly Gly Gln Ala Leu Gln Ala Leu Gln
                    355                 360                 365
Ala Ala Pro Leu Ser Gly Gln Thr Phe Thr Thr Gln Ala Ile Ser Gln
                    370                 375                 380
Glu Thr Leu Gln Asn Leu Gln Leu Gln Ala Val Pro Asn Ser Gly Pro
385                 390                 395                 400
Ile Ile Ile Arg Thr Pro Thr Val Gly Pro Asn Gly Gln Val Ser Trp
                    405                 410                 415
Gln Thr Leu Gln Leu Gln Asn Leu Gln Val Gln Asn Pro Gln Ala Gln
                    420                 425                 430
Thr Ile Thr Leu Ala Pro Met Gln Gly Val Ser Leu Gly Gln Thr Ser
                    435                 440                 445
```

-continued

```
Ser Ser Asn Thr Thr Leu Thr Pro Ile Ala Ser Ala Ala Ser Ile Pro
    450                 455                 460

Ala Gly Thr Val Thr Val Asn Ala Ala Gln Leu Ser Ser Met Pro Gly
465                 470                 475                 480

Leu Gln Thr Ile Asn Leu Ser Ala Leu Gly Thr Ser Gly Ile Gln Val
                485                 490                 495

His Pro Ile Gln Gly Leu Pro Leu Ala Ile Ala Asn Ala Pro Gly Asp
            500                 505                 510

His Gly Ala Gln Leu Gly Leu His Gly Ala Gly Gly Asp Gly Ile His
        515                 520                 525

Asp Asp Thr Ala Gly Gly Glu Gly Glu Asn Ser Pro Asp Ala Gln
    530                 535                 540

Pro Gln Ala Gly Arg Arg Thr Arg Arg Glu Ala Cys Thr Cys Pro Tyr
545                 550                 555                 560

Cys Lys Asp Ser Glu Gly Arg Gly Ser Gly Asp Pro Gly Lys Lys
                565                 570                 575

Gln His Ile Cys His Ile Gln Gly Cys Gly Lys Val Tyr Gly Lys Thr
            580                 585                 590

Ser His Leu Arg Ala His Leu Arg Trp His Thr Gly Glu Arg Pro Phe
        595                 600                 605

Met Cys Thr Trp Ser Tyr Cys Gly Lys Arg Phe Thr Arg Ser Asp Glu
    610                 615                 620

Leu Gln Arg His Lys Arg Thr His Thr Gly Glu Lys Lys Phe Ala Cys
625                 630                 635                 640

Pro Glu Cys Pro Lys Arg Phe Met Arg Ser Asp His Leu Ser Lys His
                645                 650                 655

Ile Lys Thr His Gln Asn Lys Lys Gly Gly Pro Gly Val Ala Leu Ser
            660                 665                 670

Val Gly Thr Leu Pro Leu Asp Ser Gly Ala Gly Ser Glu Gly Ser Gly
        675                 680                 685

Thr Ala Thr Pro Ser Ala Leu Ile Thr Thr Asn Met Val Ala Met Glu
    690                 695                 700

Ala Ile Cys Pro Glu Gly Ile Ala Arg Leu Ala Asn Ser Gly Ile Asn
705                 710                 715                 720

Val Met Gln Val Ala Asp Leu Gln Ser Ile Asn Ile Ser Gly Asn Gly
                725                 730                 735

Phe

<210> SEQ ID NO 75
<211> LENGTH: 781
<212> TYPE: PRT
<213> ORGANISM: Mus musculus

<400> SEQUENCE: 75

Met Ser Asp Gln Asp His Ser Met Asp Glu Val Thr Ala Val Val Lys
1               5                   10                  15

Ile Glu Lys Asp Val Gly Gly Asn Asn Gly Ser Gly Asn Gly Gly
            20                  25                  30

Gly Ala Ala Phe Ser Gln Thr Arg Ser Ser Thr Gly Ser Ser Ser
        35                  40                  45

Ser Ser Gly Gly Gly Gly Gln Glu Ser Gln Pro Ser Pro Leu Ala
    50                  55                  60

Leu Leu Ala Ala Thr Cys Ser Arg Ile Glu Ser Pro Asn Glu Asn Ser
65                  70                  75                  80
```

```
Asn Asn Ser Gln Gly Pro Ser Gln Gly Gly Thr Gly Glu Leu Asp
                85                  90                  95

Leu Thr Ala Ala Gln Leu Ser Gln Gly Ala Asn Gly Trp Gln Ile Ile
            100                 105                 110

Ser Ser Ser Ser Gly Ala Thr Pro Thr Ser Lys Glu Gln Ser Gly Asn
        115                 120                 125

Ser Thr Asn Gly Ser Glu Ser Ser Lys Asn Arg Thr Val Ser Gly Gly
    130                 135                 140

Gln Tyr Val Val Ala Ala Thr Pro Asn Leu Gln Asn Gln Gln Val Leu
145                 150                 155                 160

Thr Gly Leu Pro Gly Val Met Pro Asn Ile Gln Tyr Gln Val Ile Pro
                165                 170                 175

Gln Phe Gln Thr Val Asp Gly Gln Gln Leu Gln Phe Ala Ala Thr Gly
            180                 185                 190

Ala Gln Val Gln Gln Asp Gly Ser Gly Gln Ile Gln Ile Ile Pro Gly
        195                 200                 205

Ala Asn Gln Gln Ile Ile Pro Asn Arg Gly Ser Gly Gly Asn Ile Ile
    210                 215                 220

Ala Ala Met Pro Asn Leu Leu Gln Gln Ala Val Pro Leu Gln Gly Leu
225                 230                 235                 240

Ala Asn Asn Val Leu Ser Gly Gln Thr Gln Tyr Val Thr Asn Val Pro
                245                 250                 255

Val Ala Leu Asn Gly Asn Ile Thr Leu Leu Pro Val Asn Ser Val Ser
            260                 265                 270

Ala Ala Thr Leu Thr Pro Ser Ser Gln Ala Gly Thr Ile Ser Ser Ser
        275                 280                 285

Gly Ser Gln Glu Ser Ser Ser Gln Pro Val Thr Ser Gly Thr Ala Ile
    290                 295                 300

Ser Ser Ala Ser Leu Val Ser Ser Gln Ala Ser Ser Ser Ser Phe Phe
305                 310                 315                 320

Thr Asn Ala Asn Ser Tyr Ser Thr Thr Thr Thr Ser Asn Met Gly
                325                 330                 335

Ile Met Asn Phe Thr Ser Ser Gly Ser Ser Gly Thr Ser Ser Gln Gly
            340                 345                 350

Gln Thr Pro Gln Arg Val Gly Gly Leu Gln Gly Ser Asp Ser Leu Asn
        355                 360                 365

Ile Gln Gln Asn Gln Thr Ser Gly Gly Ser Leu Gln Gly Ser Gln Gln
    370                 375                 380

Lys Glu Gly Glu Gln Ser Gln Gln Thr Gln Gln Gln Ile Leu Ile
385                 390                 395                 400

Gln Pro Gln Leu Val Gln Gly Gly Gln Ala Leu Gln Ala Leu Gln Ala
                405                 410                 415

Ala Pro Leu Ser Gly Gln Thr Phe Thr Thr Gln Ala Ile Ser Gln Glu
            420                 425                 430

Thr Leu Gln Asn Leu Gln Leu Gln Ala Val Gln Asn Ser Gly Pro Ile
        435                 440                 445

Ile Ile Arg Thr Pro Thr Val Gly Pro Asn Gly Gln Val Ser Trp Gln
    450                 455                 460

Thr Leu Gln Leu Gln Asn Leu Gln Val Gln Asn Pro Gln Ala Gln Thr
465                 470                 475                 480

Ile Thr Leu Ala Pro Met Gln Gly Val Ser Leu Gly Gln Thr Ser Ser
                485                 490                 495
```

```
Ser Asn Thr Thr Leu Thr Pro Ile Ala Ser Ala Ala Ser Ile Pro Ala
            500             505             510

Gly Thr Val Thr Val Asn Ala Ala Gln Leu Ser Ser Met Pro Gly Leu
            515             520             525

Gln Thr Ile Asn Leu Ser Ala Leu Gly Thr Ser Gly Ile Gln Val His
            530             535             540

Gln Leu Pro Gly Leu Pro Leu Ala Ile Ala Asn Thr Pro Gly Asp His
545                 550             555                 560

Gly Thr Gln Leu Gly Leu His Gly Ser Gly Gly Asp Gly Ile His Asp
            565             570             575

Glu Thr Ala Gly Gly Glu Gly Glu Asn Ser Ser Asp Leu Gln Pro Gln
            580             585             590

Ala Gly Arg Arg Thr Arg Arg Glu Ala Cys Thr Cys Pro Tyr Cys Lys
            595             600             605

Asp Ser Glu Gly Arg Ala Ser Gly Asp Pro Gly Lys Lys Lys Gln His
            610             615             620

Ile Cys His Ile Gln Gly Cys Gly Lys Val Tyr Gly Lys Thr Ser His
625             630             635             640

Leu Arg Ala His Leu Arg Trp His Thr Gly Glu Arg Pro Phe Met Cys
            645             650             655

Asn Trp Ser Tyr Cys Gly Lys Arg Phe Thr Arg Ser Asp Glu Leu Gln
            660             665             670

Arg His Lys Arg Thr His Thr Gly Glu Lys Lys Phe Ala Cys Pro Glu
            675             680             685

Cys Pro Lys Arg Phe Met Arg Ser Asp His Leu Ser Lys His Ile Lys
            690             695             700

Thr His Gln Asn Lys Lys Gly Gly Pro Gly Val Ala Leu Ser Val Gly
705             710             715             720

Thr Leu Pro Leu Asp Ser Gly Ala Gly Ser Glu Gly Thr Ala Thr Pro
            725             730             735

Ser Ala Leu Ile Thr Thr Asn Met Val Ala Met Glu Ala Ile Cys Pro
            740             745             750

Glu Gly Ile Ala Arg Leu Ala Asn Ser Gly Ile Asn Val Met Gln Val
            755             760             765

Thr Glu Leu Gln Ser Ile Asn Ile Ser Gly Asn Gly Phe
770             775             780

<210> SEQ ID NO 76
<211> LENGTH: 10
<212> TYPE: DNA
<213> ORGANISM: Artificial Sequence
<220> FEATURE:
<223> OTHER INFORMATION: Sp1 binding site

<400> SEQUENCE: 76 kgggcggrry                                                                 10
```

PROMOTERS FOR HIGH LEVEL EXPRESSION

CROSS-REFERENCE TO RELATED APPLICATIONS

This patent application is a U.S. National Phase Application under 35 U.S.C. § 371 of International Application No. PCT/SG2015/050166, filed Jun. 17, 2015, entitled NOVEL PROMOTERS FOR HIGH LEVEL EXPRESSION, which makes reference to and claims the benefit of priority of Singapore Patent Application No. 10201403371T, filed Jun. 18, 2014, the content of which was incorporated by reference for all purposes, including an incorporation of any element or part of the description, claims or drawings not contained herein and referred to in Rule 20.5(a) of the PCT, pursuant to Rule 4.18 of the PCT.

INCORPORATION BY REFERENCE

This patent application incorporates by reference the material (i.e., Sequence Listing) in the ASCII text file named P109649_sequence_listing_finalized_ST25.txt, created on Dec. 14, 2016, having a file size of 135,616 bytes.

FIELD OF THE INVENTION

The present invention lies in the field of recombinant promoter variants capable of driving strong and sustained heterologous gene expression in in vitro and in vivo applications such as gene therapy and recombinant protein expression.

BACKGROUND OF THE INVENTION

Strong promoters are desired for high level recombinant protein production, in order to provide large quantities of a desired recombinant protein permitting a wide range of possible uses including industrial processes, diagnosis and disease treatment.

A typical promoter used for recombinant protein production contains a promoter element, an immediate upstream enhancer and if required other cis-acting regulatory elements. Optionally, transcription factors, which work in synergy to enhance transcription activity, are recruited to the site by specific sequence motifs.

Increasing recombinant protein expression through improvements in transcription and through preventing promoter silencing is desirable for optimizing yield. In order to be able to provide functional proteins, mammalian proteins are often expressed in mammalian cell lines as these can ensure the required post-translational modifications, such as "native" mammalian glycosylation patterns and molecular folding steps. Thus, mammalian cells are an important host for the production of clinically relevant recombinant proteins. The most widely used approach for this purpose is to establish a cell line with an actively expressed recombinant gene stably integrated in its genome. Alternatively, proteins can be transiently produced in cells for a limited period of time without the necessity of recombinant gene integration.

Chinese hamster ovary cells (CHO) cells have been the most commonly used mammalian host for large-scale commercial production of therapeutic proteins. The first CHO cell line was derived through single cell cloning in 1957. The cell line CHO-K1 was later derived from this ancestral cell line and it contains a slightly lower amount of DNA than the original CHO. Subsequently, another derivative of the original CHO cell line was mutagenized to yield CHO-DG44, a cell line with deletions of both dhfr alleles. While CHO cells are used in studies of genetics, toxicity screening, nutrition and gene expression, the most prominent use is recombinant protein expression.

Process development using CHO cell lines focuses on achieving the maximum amount of active product. Optimization of the amount of active product can be achieved via increasing the specific productivity (i.e., the product per cell) and/or by cell line development. Cell line development may include both sub-cloning the cell line to select higher producing clones and use of gene amplification.

Another way to achieve higher recombinant protein yields is to increase the cell yield (i.e., cells per volume) of the process. This may be accomplished through process development (e.g., batch, fed-batch, perfusion, etc.) and medium development. By increasing the cells per volume per day, higher levels of product may be produced.

However, even though efficiency and output in recombinant protein production has substantially increased in recent years, there is still the need in the art for alternative methods that allow an even higher expression level.

SUMMARY OF THE INVENTION

The inventors of the present application have found that said need can be met by novel chimeric gene regulatory units.

In a first aspect the present invention therefore relates to an isolated nucleic acid molecule comprising a functional chimeric gene regulatory unit comprising (a) a functional enhancer nucleotide sequence, (b) a functional core promoter nucleotide sequence and (c) at least one nucleotide sequence encoding for an intron, wherein the enhancer nucleotide sequence is 5' to the promoter nucleotide sequence and the intron nucleotide sequence is 3' to the promoter sequence and wherein at least one nucleotide sequence of the enhancer nucleotide sequence, the promoter nucleotide sequence or the at least one nucleotide sequence encoding for the intron is derived from a different species than the other nucleotide sequences.

In various embodiments, the isolated nucleic acid molecule further comprises at least one nucleotide sequence encoding for a polypeptide, peptide or RNA molecule, wherein said sequence is operably linked to the chimeric gene regulatory unit. The at least one nucleotide sequence encoding for a polypeptide, peptide or RNA molecule of interest may lie 3' to the intron nucleotide sequence, preferably directly adjacent to the intron sequence. In various embodiments, where the nucleotide sequence encodes for a polypeptide of interest, said polypeptide of interest is a polypeptide chain of a naturally occurring or artificial immunoglobulin. In various embodiments, the polypeptide of interest may be an antibody or fragment thereof. The antibody may be a human or humanized antibody, or a fragment thereof.

In various embodiments, the chimeric gene regulation unit has an increased resistance to transcriptional silencing.

In various embodiments, the isolated nucleic acid molecule further comprises at least one nucleotide sequence encoding for a recognition site of a restriction endonuclease. The at least one nucleotide sequence encoding for a recognition site of a restriction endonuclease may be (i) 3' to the enhancer nucleotide sequence and 5' to the promoter nucleotide sequence or (ii) 3' to the promoter nucleotide sequence and 5' to the at least one nucleotide sequence encoding for an intron.

In various embodiments, the enhancer sequence is derived from viruses, preferably from double-stranded DNA viruses. Said viruses may be of the group of Herpesviridae and Polyomaviridae, preferably of the group consisting of human cytomegalovirus, murine cytomegalovirus, and simian virus 40.

In various embodiments, any one or more of the enhancer sequence, the promoter sequence and the intron sequence are derived from human cytomegalovirus, murine cytomegalovirus, simian virus 40, the human EF-1α gene, and the chicken β-actin gene. More preferably, the promoter may be derived from human cytomegalovirus, murine cytomegalovirus, simian virus 40, the human EF-1α gene, or the chicken β-actin gene, the enhancer may be derived from human cytomegalovirus, murine cytomegalovirus, or simian virus 40, and/or the intron sequence may be derived from human cytomegalovirus, the human EF-1α gene, or the chicken β-actin gene.

In various embodiments, the enhancer sequence comprises, consists essentially of or consists of (i) a nucleotide sequence as set forth in any one of SEQ ID NO:1; SEQ ID NO:2; SEQ ID NO:3; or a complement thereof; or (ii) a nucleotide sequence that shares at least 75% sequence identity with a nucleotide sequence of (i) or a complement thereof.

In various embodiments, the promoter sequence comprises, consists essentially of or consists of (i) a nucleotide sequence as set forth in any one of SEQ ID NO:4; SEQ ID NO:5; SEQ ID NO:6; SEQ ID NO:7; SEQ ID NO:8; or a complement thereof; or (ii) a nucleotide sequence that shares at least 75% sequence identity with a nucleotide sequence of (I) or a complement thereof.

In various embodiments, the intron nucleotide sequence comprises, consists essentially of or consists of (i) a nucleotide sequence as set forth in any one of SEQ ID NO:9; SEQ ID NO:10; SEQ ID NO:11; or a complement thereof; or (ii) a nucleotide sequence that shares at least 75% sequence identity with a nucleotide sequence of (i) or a complement thereof.

In various embodiments, the chimeric gene regulatory unit comprises, consists essentially of or consists of
(1) the nucleotide sequences as set forth in SEQ ID NO:1; SEQ ID NO:4; and SEQ ID NO:11; or complements thereof;
(2) the nucleotide sequences as set forth in SEQ ID NO:2; SEQ ID NO:5; and SEQ ID NO:11; or complements thereof;
(3) the nucleotide sequences as set forth in SEQ ID NO:2; SEQ ID NO:4; and SEQ ID NO:11; or complements thereof;
(4) the nucleotide sequences as set forth in SEQ ID NO:2; SEQ ID NO:4; and SEQ ID NO:9; or complements thereof;
(5) the nucleotide sequences as set forth in SEQ ID NO:1; SEQ ID NO:5; and SEQ ID NO:11; or complements thereof;
(6) the nucleotide sequences as set forth in SEQ ID NO:1; SEQ ID NO:5; and SEQ ID NO:9; or complements thereof;
(7) the nucleotide sequences as set forth in SEQ ID NO:1; SEQ ID NO:7; and SEQ ID NO:11; or complements thereof;
(8) the nucleotide sequences as set forth in SEQ ID NO:1; SEQ ID NO:5; and SEQ ID NO:11; or complements thereof;
(9) the nucleotide sequences as set forth in SEQ ID NO:2; SEQ ID NO:7; and SEQ ID NO:9; or complements thereof;
(10) the nucleotide sequences as set forth in SEQ ID NO:2; SEQ ID NO:6; and SEQ ID NO:10; or complements thereof;
(11) the nucleotide sequences as set forth in SEQ ID NO:3; SEQ ID NO:7; and SEQ ID NO:10; or complements thereof;
(12) the nucleotide sequences as set forth in SEQ ID NO:1; SEQ ID NO:6; and SEQ ID NO:11; or complements thereof;
(13) the nucleotide sequences as set forth in SEQ ID NO:3; SEQ ID NO:5; and SEQ ID NO:10; or complements thereof;
(14) the nucleotide sequences as set forth in SEQ ID NO:1; SEQ ID NO:7; and SEQ ID NO:10; or complements thereof;
(15) the nucleotide sequences as set forth in SEQ ID NO:2; SEQ ID NO:6; and SEQ ID NO:11; or complements thereof;
(16) the nucleotide sequences as set forth in SEQ ID NO:2; SEQ ID NO:6; and SEQ ID NO:9; or complements thereof;
(17) the nucleotide sequences as set forth in SEQ ID NO:2; SEQ ID NO:7; and SEQ ID NO:11; or complements thereof;
(18) the nucleotide sequences as set forth in SEQ ID NO:1; SEQ ID NO:8; and SEQ ID NO:10; or complements thereof;
(19) the nucleotide sequences as set forth in SEQ ID NO:2; SEQ ID NO:5; and SEQ ID NO:10; or complements thereof;
(20) the nucleotide sequences as set forth in SEQ ID NO:3; SEQ ID NO:5; and SEQ ID NO:11; or complements thereof;
(21) the nucleotide sequences as set forth in SEQ ID NO:2; SEQ ID NO:5; and SEQ ID NO:9; or complements thereof;
(22) the nucleotide sequences as set forth in SEQ ID NO:2; SEQ ID NO:4; and SEQ ID NO:10; or complements thereof;
(23) the nucleotide sequences as set forth in SEQ ID NO:1; SEQ ID NO:7; and SEQ ID NO:11; or complements thereof;
(24) the nucleotide sequences as set forth in SEQ ID NO:2; SEQ ID NO:7; and SEQ ID NO:10; or complements thereof;
(25) the nucleotide sequences as set forth in SEQ ID NO:1; SEQ ID NO:5; and SEQ ID NO:10; or complements thereof; or
(26) a nucleotide sequence that shares at least 75% sequence identity with one nucleotide sequence of (1)-(25) or a complement thereof.

In various embodiments, the isolated nucleic acid molecule of the invention comprising the functional chimeric gene regulatory unit and the at least one nucleotide sequence encoding for a polypeptide, peptide or RNA molecule of interest has increased expression activity to express the polypeptide, peptide or RNA molecule of interest in CHO (Chinese Hamster Ovary) K1 or CHO DG44 cells compared to an isolated nucleic acid molecule comprising a naturally occurring gene regulatory unit and a nucleotide sequence encoding for the same polypeptide, peptide or RNA molecule of interest. The chimeric gene regulatory unit having increased expression activity in CHO K1 cells may comprise, consist essentially of or consist of (i) a nucleotide sequence as set forth in SEQ ID NO: 30, SEQ ID NO: 35, SEQ ID NO:59, SEQ ID NO:60, SEQ ID NO:62, SEQ ID NO: 64, SEQ ID NO: 65; or a complement thereof; or (ii) a nucleotide sequence that shares at least 75% sequence identity with a nucleotide sequence of (i) or a complement thereof. The chimeric gene regulatory unit having increased expression activity in CHO DG44 cells may comprise, consist essentially of or consist of (i) a nucleotide sequence as set forth in SEQ ID Nos. 34, 36, 37, 45, 47-52, 56, 57, 59-62, 64-67, 71 or a complement thereof; or (ii) a nucleotide sequence that shares at least 75% sequence identity with a nucleotide sequence of (i) or a complement thereof.

In various embodiments, the promoter comprises at least one binding site for a transcription factor. The transcription factor may be specificity protein 1 (Sp1) transcription factor. The Sp1 transcription factor may comprise, consist essentially of or consist of a polypeptide sequence as set forth in any one of SEQ ID NO:74 and SEQ ID NO:75, or a fragment thereof. In various embodiments, the at least one binding site for a transcription factor comprises, consists essentially of or consists of the nucleotide sequence set forth in SEQ ID NO:76 (5'-(G/T)GGGCGG(G/A)(G/A)(C/T)-3').

In another aspect, the present invention relates to a vector comprising the isolated nucleic acid molecule as described herein, preferably a plasmid.

In still another aspect, the present invention is also directed to a host cell comprising the isolated nucleic acid molecule or the vector as described herein. The host cell may be a eukaryotic cell, such as a CHO cell, preferably a CHO K1 cell or a CHO DG44 cell.

Another aspect of the invention is directed to the use of the isolated nucleic acid molecule of the invention for facilitating or enhancing the expression of a polypeptide, peptide or RNA of interest, wherein said isolated nucleic acid molecule comprises a nucleotide sequence encoding the polypeptide, peptide or RNA of interest, wherein said nucleotide sequence encoding the polypeptide, peptide or RNA of interest is operably linked to the chimeric gene regulatory unit of the isolated nucleic acid molecule.

Still another aspect is related to a method of producing a polypeptide, peptide or RNA of interest, comprising:

(i) providing the isolated nucleic acid molecule as described herein, wherein said isolated nucleic acid molecule comprises a nucleotide sequence encoding the polypeptide, peptide or RNA of interest, said nucleotide sequence encoding the polypeptide, peptide or RNA of interest being operably linked to the chimeric gene regulatory unit of the isolated nucleic acid molecule; and (ii) producing the polypeptide, peptide or RNA of interest by in vitro transcription and translation or in a suitable host cell under conditions that allow production of the polypeptide, peptide or RNA of interest. In such methods, the host cell may be a eukaryotic cell, such as a CHO cell, preferably a CHO K1 cell or a CHO DG44 cell.

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

Figure 1:
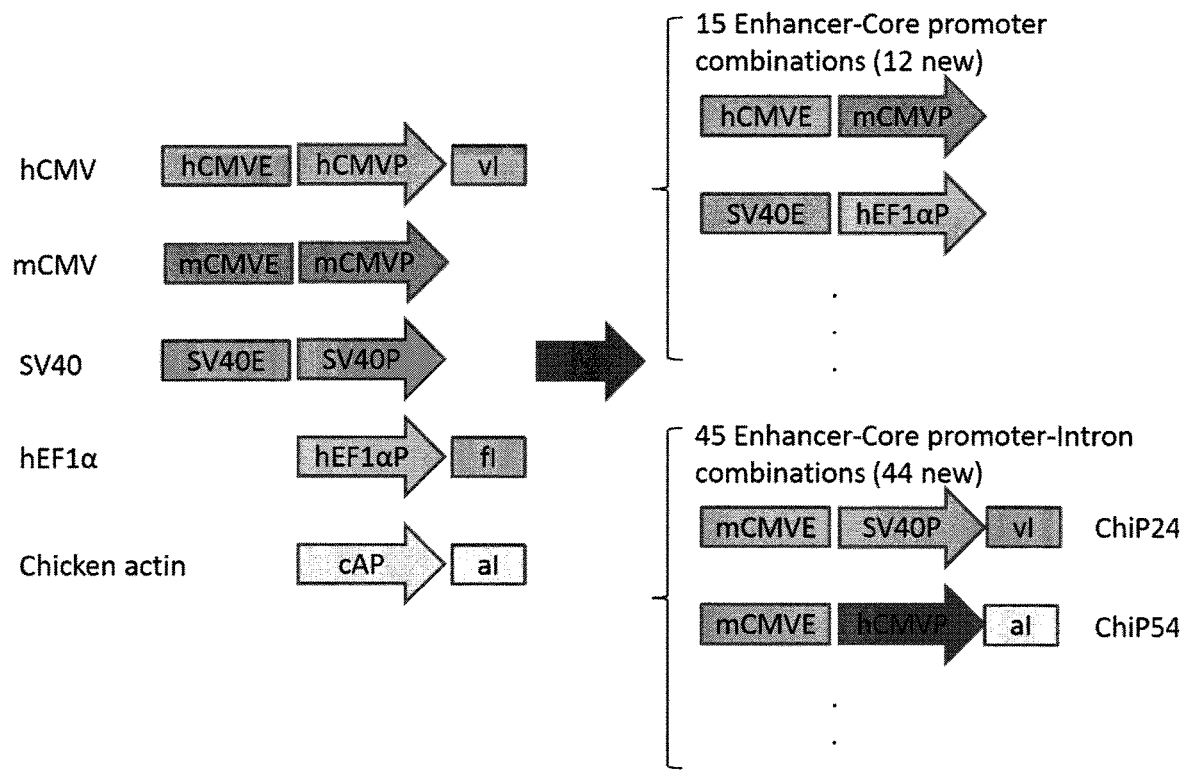
FIG. 1 shows a schematic overview of the design of the chimeric gene regulatory unit. Five natural gene regulatory units occurring upstream of the human cytomegalovirus immediate early gene (hCMV), of the murine cytomegalovirus immediate early gene (mCMV), the simian virus 40 (SV40), the human elongation factor-1α gene (hEF-1α) and the chicken β-actin gene (cA) were dissected into enhancers (E), core promoters (CP) and introns (I). These enhancers, core promoters, and introns from different sources were then combined to generate fifty-seven new enhancer-core promoter and enhancer-core promoter-intron combinations, referred to as chimeric gene regulatory units or hybrid promoters.

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. In case of conflict, the present document, including definitions, will control.

The object of the present invention is to provide novel chimeric gene regulatory units for high level expression of a molecule of interest.

In one first aspect, the present invention relates to an isolated nucleic acid molecule comprising a functional chimeric gene regulatory unit comprising (a) a functional enhancer nucleotide sequence, (b) a functional promoter nucleotide sequence and (c) at least one nucleotide sequence encoding for an intron, wherein the enhancer nucleotide sequence is 5' to the promoter nucleotide sequence and the intron nucleotide sequence is 3' to the promoter sequence and wherein at least one nucleotide sequence of the enhancer nucleotide sequence, the promoter nucleotide sequence or the at least one nucleotide sequence encoding for the intron is derived from a different species than the other nucleotide sequences.

As used herein the term "functional" refers to an entity, which possesses either the native biological activity of the naturally-occurring entity of its type, or any specific desired activity, for example in case of a promoter as judged by its ability to initiate gene transcription.

As used herein the term "isolated nucleic acid molecule" relates to nucleic acid molecules that may appear independent of their natural genetic context and/or background and are preferably separated from other nucleic acids or cellular components. The separation may occur by purification, for which various techniques are known in the art.

The term "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), any phosphoester analogs thereof, such as phosphorothioates and thioesters, in either single stranded form, or as a double-stranded helix as well as artificial nucleic acid analogs such as peptide nucleic acid, morpholino- and locked nucleic acid, as well as glycol nucleic acid and threose nucleic acid. Each of these artificial nucleic acid analogs is distinguished from naturally occurring DNA or RNA by changes to the backbone of the molecule. In preferred embodiments the isolated nucleic acid molecule is a DNA molecule.

"At least one", as used herein, relates to one or more, in particular 1, 2, 3, 4, 5, 6, 7, 8, 9, 10 or more.

The articles "a" and "an" are used herein to refer to one or to more than one (i.e., to at least one) of the grammatical object of the article. By way of example, "an element" means at least one element and can include more than one element.

The term "sequence", as used herein in relation to nucleic acids, relates to the primary sequence of nucleic acid molecules.

As used herein the term "functional chimeric gene regulatory unit" or "hybrid promoter" refers to the combination of enhancer, core promoter and at least one intron as described herein.

As used herein the term "chimeric" or "hybrid" refers to the fact that different elements of the regulatory unit are derived from different genes, i.e. in nature the combinations of elements of the regulatory unit as described herein do not exist. This may be achieved by using at least one of the elements from a different species and combining it with the other elements of the regulatory unit. At least one of the enhancer, the core promoter and the intron is thus heterologous with respect to at least one of the other two.

As used herein the term "functional enhancer" refers to a short region of DNA that can activate transcription (of a gene), for example by being capable of binding proteins (activators).

In general the term "promoter" refers to a region of DNA that initiates transcription of a particular gene.

As used herein the term "functional promoter" or "core promoter" refers to the core region in a promoter, which is the minimal portion of the promoter required to properly initiate gene transcription.

As used herein the term "intron" refers to a nucleotide sequence within a gene that is removed by RNA splicing during maturation of the final RNA product. The term intron refers to both the DNA sequence within a gene and the corresponding sequence in RNA transcripts. Sequences that are joined together in the final mature RNA after RNA splicing are exons.

The term "5'" as used herein refers to the directionality, i.e., the end-to-end chemical orientation of a single strand of nucleic acid. The chemical convention of naming carbon atoms in the nucleotide sugar-ring numerically gives rise to a 5-end and a 3-end. The relative positions of structures along a strand of nucleic acid, including genes and various protein binding sites, are usually noted as being either upstream (towards the 5-end) or downstream (towards the 3-end). This naming convention is important because nucleic acids can only be synthesized in vivo in the 5-to-3'direction, as the polymerase that assembles new strands only attaches new nucleotides to the 3-hydroxyl (—OH) group, via a phosphodiester bond.

In various embodiments, the isolated nucleic acid molecule further comprises at least one nucleotide sequence encoding for a peptide, polypeptide or RNA molecule of interest. Said molecules of interest are those to be expressed using the novel chimeric gene regulatory units if high level expression is desired. Preferably, it is a recombinant polypeptide or protein.

As used herein, the term "peptide" relates to two or more amino acids linked by a peptide bond and thus includes dipeptides, oligopeptides, and polypeptides.

The term "polypeptide", as used herein, refers to a long, continuous peptide chain, preferably of at least 50 amino acids in length.

The term "protein", as used herein, relates to one or more polypeptides arranged in a biologically functional way. A protein may consist of more than one polypeptide chains, such as an antibody, which consists of two light chains and two heavy chains, with each of the chains being a polypeptide. A protein may be bound to ligands such as coenzymes and cofactors or to another protein or other macromolecule.

In various embodiments, said sequence encoding the molecule of interest is operably linked to the chimeric gene regulatory unit. In preferred embodiments, the at least one nucleotide sequence encoding for a molecule of interest lies 3' (downstream) relative to the intron nucleotide sequence. In more preferred embodiments, the at least one nucleotide sequence encoding a molecule of interest lies directly adjacent to the intron sequence.

"Directly adjacent" means that the intron sequence and the coding sequence are directly linked by a phosphodiester bond and that no linker nucleotide sequence is interposed between the two elements.

As used herein the term "operably linked" means associated in such a way that the chimeric gene regulatory unit may control expression of the molecule of interest.

It is advantageous that the at least one nucleotide sequence encoding for a molecule of interest lies directly adjacent to the intron sequence, because this increases the chances of correct and high level expression.

In various embodiments, where the at least one nucleotide sequence encoding for a molecule of interest encodes for a polypeptide of interest, said polypeptide is a polypeptide chain of a naturally occurring or artificial immunoglobulin. In preferred embodiments, the polypeptide of interest is a protein and the protein is an antibody. In more preferred embodiments, the antibody is a human or humanized antibody, or a fragment thereof. It is understood that in such embodiments, wherein expression of an immunoglobulin, specifically an antibody is desired, the isolated nucleic acid molecules comprises nucleotide sequences that encode for more than one polypeptide. For example, in case antibody expression is desired, the isolated nucleic acid molecule may comprise two nucleic acid sequences encoding for a polypeptide of interest, namely one sequence encoding the heavy chain and one sequence encoding the light chain. In such embodiments, the different coding sequences may be directly linked or may be separated by linker nucleotide sequences. Said linker nucleotide sequences may be functional in that they allow ribosomal binding and may thus for example include internal ribosomal entry sites (IRES).

As used herein and in line with the above, the term "immunoglobulin" refers to a protein consisting of one or more polypeptides substantially encoded by immunoglobulin genes.

In various embodiments, the chimeric gene regulation unit has an increased resistance to transcriptional silencing.

The term "transcriptional silencing" refers to any mechanism, whereby gene expression is down-regulated on transcriptional level, e.g. via DNA methylation, histone modifications and chromatin remodeling, which make the DNA permanently inaccessible for future transcription.

It is advantageous if the chimeric gene regulation unit has an increased resistance to transcriptional silencing, as this will result in higher overall yields of expressed product.

In various embodiments, the isolated nucleic acid molecule further comprises at least one nucleotide sequence encoding for a recognition site of a restriction endonuclease.

In preferred embodiments, said at least one nucleotide sequence encoding for a recognition site of a restriction endonuclease is 3' to the enhancer nucleotide sequence and 5' to the promoter nucleotide sequence. Alternatively, in various preferred embodiments, said nucleotide sequence encoding for a recognition site of a restriction endonuclease is 3' to the promoter nucleotide sequence and 5' to the at least one nucleotide sequence encoding for an intron. This location allows separating and combining the different elements of the regulatory unit in a specific manner, e.g. linking enhancer, promoter and intron sequences.

As used herein, the term "restriction endonuclease" is intended to mean an enzyme that recognizes a specific nucleotide sequence in a nucleic acid and cleaves the nucleic acid. A restriction endonuclease can recognize a sequence that is, for example, 4, 5, 6, 7 or more nucleotides long. A restriction endonuclease can recognize more than one sequence, for example, two or more variants of a degenerate sequence that includes one of two or more different nucleotides at a particular position. Alternatively, a restriction endonuclease can be specific for a single recognition sequence.

As used herein, the term "recognition site" is intended to mean a portion of the nucleic acid having a nucleotide sequence that specifically binds to a particular binding moiety such as a restriction endonuclease, more specifically the substrate recognition and binding site of a restriction endonuclease. Typically, a restriction endonuclease recognition site is cleaved by a restriction endonuclease.

In various embodiments, the enhancer sequence is derived from viruses. In preferred embodiments, the enhancer sequence is derived from double-stranded DNA viruses. In more preferred embodiments, the enhancer sequence is derived from viruses consisting of the group of Herpesviridae and Polyomaviridae. In still more preferred embodiments, the enhancer sequence is derived from the group consisting of human cytomegalovirus; murine cytomegalovirus; and simian virus 40.

Cytomegalovirus is a viral genus of the Herpesviridae abbreviated as CMV. The species that infects humans is commonly known as human CMV (hCMV). Other CMV viruses such as murine cytomegalovirus in mice are found in several mammal species, but species isolated from animals differ from hCMV in terms of genomic structure.

Simian virus 40 (SV40) is a polyomavirus that is found in both monkeys and humans.

In various embodiments, the enhancer sequence comprises, consists essentially of or consists of (i) a nucleotide sequence as set forth in any one of SEQ ID NO:1; SEQ ID NO:2; SEQ ID NO:3; or a complement thereof; or (ii) a nucleotide sequence that shares at least 75%, 80%, 85%, 86%, 87%, 88%, 89%, 90%, 91%, 92%, 93%, 94%, 95%, 96%, 97%, 97.5%, 98.0%, 98.5%, 99.0%, or 99.5% sequence identity with a nucleotide sequence of (i) or a complement thereof.

"Complement", as used herein, relates to a nucleic acid molecule which is complementary to another nucleic acid molecule when both nucleic acid molecules are aligned antiparallel to each other in that essentially all nucleotides of either of the nucleic acid molecules form Watson-Crick base pairs with the corresponding nucleotides on the other molecule. In various embodiments, the complements are full complements in that each nucleotide of the respective molecule or sequence forms a Watson-Crick base pair with a corresponding nucleotide on the other strand.

The term "sequence identity," as used herein, is generally expressed as a percentage and refers to the percent of amino acid residues or nucleotides, as appropriate, that are identical as between two sequences when optimally aligned. For the purposes of this invention, sequence identity means the sequence identity determined using the well-known Basic Local Alignment Search Tool (BLAST), which is publicly available through the National Cancer Institute/National Institutes of Health (Bethesda, Md.) and has been described in printed publications (see, e.g., Altschul et al., J. Mol. Biol, 215(3), 403-10 (1990)).

In various embodiments, the sequence of the core promoter is derived from the group consisting of human cytomegalovirus; murine cytomegalovirus; simian virus 40; the human EF-1α gene promoter; and the chicken β-actin gene promoter.

Elongation factor 1-alpha 1 (EF-1α) is a protein that in humans is encoded by the EEF1A1 gene. This gene encodes an isoform of the alpha subunit of the elongation factor-1 complex, which is responsible for the enzymatic delivery of aminoacyl tRNAs to the ribosome.

In various embodiments, the core promoter sequence comprises, consists essentially of or consists of (i) a nucleotide sequence as set forth in any one of SEQ ID NO:4; SEQ ID NO:5; SEQ ID NO:6; SEQ ID NO:7; SEQ ID NO:8; or a complement thereof; or (ii) a nucleotide sequence that shares at least 75%, 80%, 85%, 86%, 87%, 88%, 89%, 90%, 91%, 92%, 93%, 94%, 95%, 96%, 97%, 97.5%, 98.0%, 98.5%, 99.0%, or 99.5% sequence identity with a nucleotide sequence of (i) or a complement thereof.

In various embodiments, the intron nucleotide sequence is selected from a sequence derived from the group consisting of human cytomegalovirus; the human EF-1α gene; and the chicken β-actin gene.

In various embodiments, the intron nucleotide sequence comprises, consists essentially of or consists of (i) a nucleotide sequence as set forth in any one of SEQ ID NO:9; SEQ ID NO:10; SEQ ID NO:11; or a complement thereof; (ii) a nucleotide sequence that shares at least 75%, 80%, 85%, 86%, 87%, 88%, 89%, 90%, 91%, 92%, 93%, 94%, 95%, 96%, 97%, 97.5%, 98.0%, 98.5%, 99.0%, or 99.5% sequence identity with a nucleotide sequence of (i) or a complement thereof.

The above elements may be combined, such that the chimeric gene regulatory unit comprises, consists essentially of or consists of (1) the nucleotide sequences as set forth in SEQ ID NO:1; SEQ ID NO:4; and SEQ ID NO:11; or complements thereof;
(2) the nucleotide sequences as set forth in SEQ ID NO:2; SEQ ID NO:5; and SEQ ID NO:11; or complements thereof;
(3) the nucleotide sequences as set forth in SEQ ID NO:2; SEQ ID NO:4; and SEQ ID NO:11; or complements thereof;
(4) the nucleotide sequences as set forth in SEQ ID NO:2; SEQ ID NO:4; and SEQ ID NO:9; or complements thereof;
(5) the nucleotide sequences as set forth in SEQ ID NO:1; SEQ ID NO:5; and SEQ ID NO:11; or complements thereof;
(6) the nucleotide sequences as set forth in SEQ ID NO:1; SEQ ID NO:5; and SEQ ID NO:9; or complements thereof;
(7) the nucleotide sequences as set forth in SEQ ID NO:1; SEQ ID NO:7; and SEQ ID NO:11; or complements thereof; or
(8) a nucleotide sequence that shares at least 75%, 80%, 85%, 86%, 87%, 88%, 89%, 90%, 91%, 92%, 93%, 94%, 95%, 96%, 97%, 97.5%, 98.0%, 98.5%, 99.0%, or 99.5% sequence identity with one nucleotide sequence of (1)-(7) or a complement thereof.

Such chimeric gene regulatory units are advantageous as it was surprisingly found that they exhibit higher recombinant protein production levels in CHO KG1 cells compared with wild type gene regulatory units or different chimeric gene regulatory units.

The term "wild-type" (WT), as used herein, refers to the typical, most common or conventional form as it occurs in nature.

In various embodiments, the isolated nucleic acid molecule of the invention comprising the functional chimeric gene regulatory unit and the at least one nucleotide sequence encoding for a molecule of interest has increased expression activity in that it expresses a molecule of interest in Chinese Hamster Ovary (CHO) K1 cells in higher levels relative to an isolated nucleic acid molecule comprising a naturally occurring gene regulatory unit and a nucleotide sequence encoding for the same molecule of interest. In preferred embodiments, the increased expression activity of the functional chimeric gene regulatory unit is at least 1.1-fold, 1.15-fold, 1.2-fold, 1.4-fold, 1.5-fold, 1.6-fold or 1.75-fold higher compared to the naturally occurring gene regulatory unit.

CHO cells are advantageous due to their ability to produce glycoproteins with post-translational modifications compatible to humans, their refractory nature to human viruses, the availability of well-established gene amplification systems for CHO cells coupled with the cells ability to adapt and grow in serum-free suspension culture. These characteristics render the CHO cells ideal for large scale high-titer cultures in the industry.

In various embodiments, the chimeric gene regulatory unit comprises, consists essentially of or consists of (i) a nucleotide sequence as set forth in SEQ ID NO: 30, SEQ ID NO: 35, SEQ ID NO:59, SEQ ID NO:60, SEQ ID NO:62, SEQ ID NO: 64, SEQ ID NO: 65 or a complement thereof; or (ii) a nucleotide sequence that shares at least 75%, 80%, 85%, 86%, 87%, 88%, 89%, 90%, 91%, 92%, 93%, 94%, 95%, 96%, 97%, 97.5%, 98.0%, 98.5%, 99.0%, or 99.5% sequence identity with a nucleotide sequence of (i) or a complement thereof. It was found that said constructs provide for increased expression activity in CHO K1 cells. Particularly preferred is a chimeric gene regulatory unit that comprises, consists essentially of or consists of the nucleotide sequence as set forth in SEQ ID NO:35 or a nucleotide sequence that shares at least 75%, 80%, 85%, 86%, 87%, 88%, 89%, 90%, 91%, 92%, 93%, 94%, 95%, 96%, 97%, 97.5%, 98.0%, 98.5%, 99.0%, or 99.5% sequence identity with said nucleotide sequence of SEQ ID NO:35 or the respective complements of these sequences. It was found that said sequence is particularly advantageous—even though it may not provide the highest titer—because the time used to generate stably transfected cell pools with said chimeric gene regulatory unit is significantly shorter—e.g. three weeks instead of two weeks—compared to the chimeric promoters set forth in SEQ ID Nos. 30, 59, 60, 62, 64 and 65.

In various other embodiments, the chimeric gene regulatory unit comprises, consists essentially of or consists of
(1) the nucleotide sequences as set forth in SEQ ID NO:2; SEQ ID NO:4; and SEQ ID NO:11; or complements thereof;
(2) the nucleotide sequences as set forth in SEQ ID NO:2; SEQ ID NO:5; and SEQ ID NO:11; or complements thereof;
(3) the nucleotide sequences as set forth in SEQ ID NO:1; SEQ ID NO:5; and SEQ ID NO:11; or complements thereof;
(4) the nucleotide sequences as set forth in SEQ ID NO:2; SEQ ID NO:7; and SEQ ID NO:9; or complements thereof;
(5) the nucleotide sequences as set forth in SEQ ID NO:2; SEQ ID NO:6; and SEQ ID NO:10; or complements thereof;
(6) the nucleotide sequences as set forth in SEQ ID NO:3; SEQ ID NO:7; and SEQ ID NO:10; or complements thereof;
(7) the nucleotide sequences as set forth in SEQ ID NO:1; SEQ ID NO:6; and SEQ ID NO:11; or complements thereof;
(8) the nucleotide sequences as set forth in SEQ ID NO:3; SEQ ID NO:5; and SEQ ID NO:10; or complements thereof;
(9) the nucleotide sequences as set forth in SEQ ID NO:1; SEQ ID NO:7; and SEQ ID NO:10; or complements thereof;
(10) the nucleotide sequences as set forth in SEQ ID NO:2; SEQ ID NO:6; and SEQ ID NO:11; or complements thereof;
(11) the nucleotide sequences as set forth in SEQ ID NO:2; SEQ ID NO:6; and SEQ ID NO:9; or complements thereof;
(12) the nucleotide sequences as set forth in SEQ ID NO:2; SEQ ID NO:7; and SEQ ID NO:11; or complements thereof;
(13) the nucleotide sequences as set forth in SEQ ID NO:1; SEQ ID NO:8; and SEQ ID NO:10; or complements thereof;
(14) the nucleotide sequences as set forth in SEQ ID NO:2; SEQ ID NO:5; and SEQ ID NO:10; or complements thereof;
(15) the nucleotide sequences as set forth in SEQ ID NO:3; SEQ ID NO:5; and SEQ ID NO:11; or complements thereof;
(16) the nucleotide sequences as set forth in SEQ ID NO:1; SEQ ID NO:4; and SEQ ID NO:11; or complements thereof;
(17) the nucleotide sequences as set forth in SEQ ID NO:2; SEQ ID NO:5; and SEQ ID NO:9; or complements thereof;
(18) the nucleotide sequences as set forth in SEQ ID NO:2; SEQ ID NO:4; and SEQ ID NO:10; or complements thereof;
(19) the nucleotide sequences as set forth in SEQ ID NO:1; SEQ ID NO:7; and SEQ ID NO:11; or complements thereof;
(20) the nucleotide sequences as set forth in SEQ ID NO:2; SEQ ID NO:7; and SEQ ID NO:10; or complements thereof;
(21) the nucleotide sequences as set forth in SEQ ID NO:1; SEQ ID NO:5; and SEQ ID NO:10; or complements thereof; or
(22) a nucleotide sequence that shares at least 75%, 80%, 85%, 86%, 87%, 88%, 89%, 90%, 91%, 92%, 93%, 94%, 95%, 96%, 97%, 97.5%, 98.0%, 98.5%, 99.0%, or 99.5% sequence identity with one nucleotide sequence of (1)-(21) or a complement thereof.

Such chimeric gene regulatory units are advantageous as it was surprisingly found that they exhibit higher recombinant protein production levels in CHO DG44 cells compared with wild type gene regulatory units or different chimeric gene regulatory units.

Accordingly, in various embodiments, the isolated nucleic acid molecule of the invention comprising the functional chimeric gene regulatory unit and the at least one nucleotide sequence encoding for a molecule of interest has increased expression activity to express a molecule of interest in Chinese Hamster Ovary (CHO) DG44 cells compared to an isolated nucleic acid molecule comprising a naturally occurring gene regulatory unit and a nucleotide sequence encoding for the molecule of interest. In preferred embodiments, the increased expression activity of the functional chimeric gene regulatory unit is at least 1.1-fold, 1.2-fold, 1.3-fold, 1.4-fold, 1.5-fold, 1.6-fold or 1.7-fold higher compared to the naturally occurring gene regulatory unit.

In various embodiments, the chimeric gene regulatory unit having increased expression activity in CHO DG44 cells comprises, consists essentially of or consists of (i) a nucleotide sequence as set forth in SEQ ID Nos. 34, 36, 37, 45, 47-52, 56, 57, 59-62, 64-67, 71 or a complement thereof; or (ii) a nucleotide sequence that shares at least 75%, 80%, 85%, 86%, 87%, 88%, 89%, 90%, 91%, 92%, 93%, 94%, 95%, 96%, 97%, 97.5%, 98.0%, 98.5%, 99.0%, or 99.5% sequence identity with a nucleotide sequence of (i), or a complement thereof.

Such chimeric gene regulatory units are advantageous as it was surprisingly found that they exhibit higher recombinant protein production levels as achieved with wild type gene regulatory units or different chimeric gene regulatory units.

In various embodiments, the chimeric gene regulatory unit comprises at least one binding site for a transcription factor.

In preferred embodiments, the at least one binding site for a transcription factor is comprised in the enhancer, the core promoter or the intron.

As used herein the term "transcription factor" refers to a protein that binds to specific DNA sequences, thereby controlling the rate of transcription of genetic information from DNA to messenger RNA (mRNA). Transcription factors perform this function alone or with other proteins in a complex, by promoting (as an activator), or blocking (as a repressor) the recruitment of RNA polymerase to specific genes. A defining feature of transcription factors is that they contain one or more DNA-binding domains (DBDs), which attach to specific sequences of DNA adjacent to the genes that they regulate. Herein, it is preferred that the recruited transcription factors activate RNA polymerase binding and function.

In preferred embodiments, the transcription factor is specificity protein 1 (Sp1) transcription factor. This may be advantageous as it has been shown that the SP1 binding site may enhance expression during long term culture. The Sp1 transcription factor may comprise, consist essentially of or consist of the polypeptide sequence as set forth in SEQ ID NO:74 or SEQ ID NO:75, or may be a fragment thereof, with said fragment being functional in that it retains at least 50% activity of the full length sequence. Alternatively, in other preferred embodiments, the at least one binding site for a transcription factor contained in the nucleic acid molecules described herein comprises, consists essentially of or consists of the nucleotide sequence set forth in SEQ ID NO:76 (5'-(G/T)GGGCGG(G/A)(G/A)(C/T)-3').

The use of a transcription factor is advantageous as it represents an additional tool for controlling and improving the rate of transcription of genetic information from DNA to messenger RNA and hence achieving higher expression levels.

In a further aspect, the invention relates to a vector comprising the isolated nucleic acid molecule of the invention.

As used herein the term "vector" refers to a nucleic acid molecule used as a vehicle to artificially carry foreign genetic material into another cell, where it can be replicated and/or expressed. The four major types of vectors are plasmids, viral vectors, cosmids, and artificial chromosomes. Common to all engineered vectors are an origin of replication, a multicloning site, and a selectable marker. The vector itself is generally a nucleic acid sequence that consists of an insert (transgene) and a larger sequence that serves as the "backbone" of the vector. The purpose of a vector, which transfers genetic information to another cell, is typically to isolate, multiply, or express the insert in the target cell. In preferred embodiments, the vector is a plasmid.

In a still further aspect, the invention relates to a host cell comprising the isolated nucleic acid molecule of the invention and/or the vector of the invention.

The term "host cell" as used herein means an organism that harbors the nucleic acid molecules comprising the chimeric gene regulatory unit as described herein. They may be integrated into the genome of the host cell or exist in separate form in the cell.

In various embodiments, said host cell is a eukaryotic cell. In preferred embodiments, said host cell is a mammalian cell. In even more preferred embodiments said host cell is a Chinese hamster ovary (CHO) cell. In more preferred embodiments, the host cell is a CHO K1 cell or a CHO DG44 cell.

The nucleic acid molecules described herein can be used to facilitate or enhance the expression of a given molecule of interest in a cell. It is understood that in such embodiments, said isolated nucleic acid molecule also comprises a nucleotide sequence encoding the molecule of interest being operably linked to the chimeric gene regulatory unit of the isolated nucleic acid molecule.

In such methods for the expression of molecules of interest, in particular polypeptides, the actual expression may be performed by by in vitro transcription and translation or, more preferably, recombinantly in a suitable host cell under conditions that allow production of the molecule of interest.

The host cell may be a cell as described above.

Conditions that allow production of the molecule of interest include the various parameters of cell culture, including selection of the medium and the cultivating conditions, such as temperature, time, etc. All of these factors are well-known to those skilled in the art and can be easily adapted by using routine techniques.

It is understood that all embodiments disclosed herein in relation to the nucleic acids of the invention are similarly applicable to the vectors, host cells, uses and methods, described herein, and vice versa.

The present invention is further illustrated by the following examples. However, it should be understood, that the invention is not limited to the exemplified embodiments.

EXAMPLES

Five natural promoters occurring upstream of the human cytomegalovirus immediate early gene (hCMV), of the murine cytomegalovirus immediate early gene (mCMV), the simian virus 40 (SV40), the human elongation factor-1α gene (hEF-1α) and the chicken β-actin gene (cA) were dissected into enhancers (E), core promoters (CP) and introns (I) (FIG. 1). These enhancers, core promoters, and introns from different sources were then recombined to generate fifty-seven new enhancer-core promoter and enhancer-core promoter-intron combinations, referred to as chimeric gene regulatory units or hybrid promoters.

Table 1 shows the different elements used for generation of the chimeric gene regulatory units while Table 2 shows the tested combinations.

TABLE 1

Naturally occurring enhancers, promoters, and introns

| Origin | Enhancer | SEQ ID No. | Core Promoter | SEQ ID No. | Intron | SEQ ID No. |
|---|---|---|---|---|---|---|
| Human CMV (hCMV) | hCMVE | 1 | hCMVP | 4 | hCMV IntronA (vI) | 9 |
| Murine CMV (mCMV) | mCMVE | 2 | mCMVP | 5 | | |
| SV40 | SV40E | 3 | SV40P | 6 | | |

TABLE 1-continued

Naturally occurring enhancers, promoters, and introns

| Origin | Enhancer | SEQ ID No. | Core Promoter | SEQ ID No. | Intron | SEQ ID No. |
|---|---|---|---|---|---|---|
| Human EF gene (hEF) | | | hEFP | 7 | EF Intron (fI) | 10 |
| Chicken beta actin (cA) | | | cAP | 8 | cA Intron (aI) | 11 |

TABLE 2

Assessed gene regulatory units

| | Name | Enhancer | Core promoter | Intron | SEQ ID No |
|---|---|---|---|---|---|
| 1 | WT hCMV | HCMVE | hCMVP | | 12 |
| 2 | WT mCMV | MCMVE | mCMVP | | 13 |
| 3 | WT SV40 | SV40E | SV40P | | 14 |
| 4 | WT hEF | | hEFP | fI | 15 |
| 5 | WT cA | | cAP | aI | 16 |
| 6 | hCmC | hCMVE | mCMVP | | 17 |
| 7 | hCS | hCMVE | SV40P | | 18 |
| 8 | hCE | hCMVE | hEFP | | 19 |
| 9 | hCA | hCMVE | CAP | | 20 |
| 10 | mChC | mCMVE | hCMVP | | 21 |
| 11 | mCS | mCMVE | SV40P | | 22 |
| 12 | mCE | mCMVE | hEFP | | 23 |
| 13 | mCA | mCMVE | CAP | | 24 |
| 14 | ShC | SV40E | hCMVP | | 25 |
| 15 | SmC | SV40E | mCMVP | | 26 |
| 16 | SE | SV40E | hEFP | | 27 |
| 17 | SA | SV40E | CAP | | 28 |
| 18 | WT hCMVvI | hCMVE | hCMVP | vI | 29 |
| 19 | hCmCvI | hCMVE | mCMVP | vI | 30 |
| 20 | hCSvI | hCMVE | SV40P | vI | 31 |
| 21 | hCEvI | hCMVE | hEFP | vI | 32 |
| 22 | hCAvI | hCMVE | CAP | vI | 33 |
| 23 | mCMVvI | mCMVE | mCMVP | vI | 34 |
| 24 | mChCvI | mCMVE | hCMVP | vI | 35 |
| 25 | mCSvI | mCMVE | SV40P | vI | 36 |
| 26 | mCEvI | mCMVE | hEFP | vI | 37 |
| 27 | mCAvI | mCMVE | CAP | vI | 38 |
| 28 | SV40vI | SV40E | SV40P | vI | 39 |
| 29 | ShCvI | SV40E | hCMVP | vI | 40 |
| 30 | SmCvI | SV40E | mCMVP | vI | 41 |
| 31 | SEvI | SV40E | hEFP | vI | 42 |
| 32 | SAvI | SV40E | CAP | vI | 43 |
| 33 | hCMVfI | hCMVE | hCMVP | fI | 44 |
| 34 | hCmCfI | hCMVE | mCMVP | fI | 45 |
| 35 | hCSfI | hCMVE | SV40P | fI | 46 |
| 36 | hCEfI | hCMVE | hEFP | fI | 47 |
| 37 | hCAfI | hCMVE | CAP | fI | 48 |
| 38 | mCMVfI | mCMVE | mCMVP | fI | 49 |
| 39 | mChCfI | mCMVE | hCMVP | fI | 50 |
| 40 | mCSfI | mCMVE | SV40P | fI | 51 |
| 41 | mCEfI | mCMVE | hEFP | fI | 52 |
| 42 | mCAfI | mCMVE | CAP | fI | 53 |
| 43 | SV40fI | SV40E | SV40P | fI | 54 |
| 44 | ShCfI | SV40E | hCMVP | fI | 55 |
| 45 | SmCfI | SV40E | mCMVP | fI | 56 |
| 46 | SEfI | SV40E | hEFP | fI | 57 |
| 47 | SAfI | SV40E | CAP | fI | 58 |
| 48 | hCMVaI | hCMVE | hCMVP | aI | 59 |
| 49 | hCmCaI | hCMVE | mCMVP | aI | 60 |
| 50 | hCSaI | hCMVE | SV40P | aI | 61 |
| 51 | hCEaI | hCMVE | hEFP | aI | 62 |
| 52 | hCAaI | hCMVE | CAP | aI | 63 |
| 53 | mCMVaI | mCMVE | mCMVP | aI | 64 |
| 54 | mChCaI | mCMVE | hCMVP | aI | 65 |
| 55 | mCSaI | mCMVE | SV40P | aI | 66 |
| 56 | mCEaI | mCMVE | hEFP | aI | 67 |
| 57 | mCAaI | mCMVE | CAP | aI | 68 |
| 58 | SV40aI | SV40E | SV40P | aI | 69 |
| 59 | ShCaI | SV40E | hCMVP | aI | 70 |
| 60 | SmCaI | SV40E | mCMVP | aI | 71 |
| 61 | SEaI | SV40E | hEFP | aI | 72 |
| 62 | SAaI | SV40E | CAP | aI | 73 |

Figure 2:
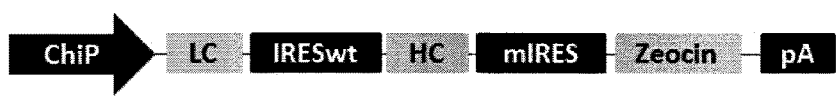
FIG. 2 shows a schematic representation of monoclonal antibody expressing vectors for comparison of different chimeric promoters. (A) Antibody expression vector for comparison of chimeric promoters in CHO K1 cells. (B) Antibody expression vector for comparison of chimeric promoters in CHO DG44 cells. ChiP: chimeric gene regulatory unit; LC: antibody light chain encoding sequence; HC: antibody heavy chain encoding sequence; Zeo: zeocin encoding sequence; DHFR: dihydrofolate reductase encoding sequence; IRESwt: wild-type encephalomyocarditis virus internal ribosome entry site; mIRES, mutated IRES with reduced translation efficiency; pA: polyadenlyation signal.
Figure 2:

The different chimeric gene regulatory units were then inserted into antibody expression vectors for comparison of chimeric promoters in CHO K1 and CHO DG44 cells with the arrangement of the different elements in the vectors schematically shown in FIG. 2.

Figure 3:
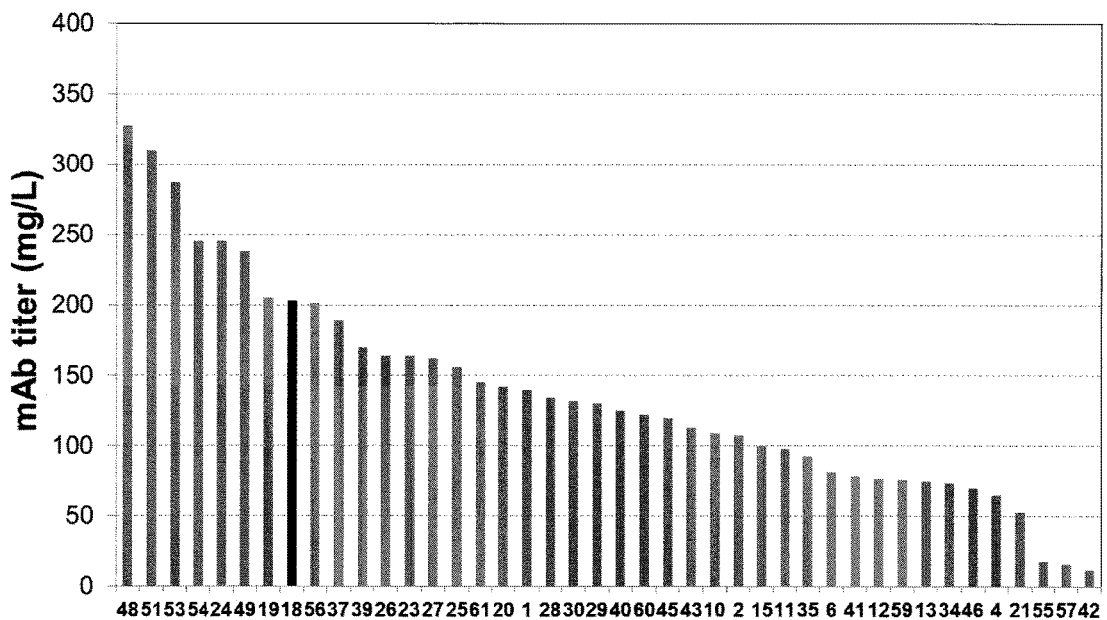
FIG. 3 shows the results of the comparison of the newly generated chimeric gene regulatory units according to FIG. 2 and Table 2 with the wild type promoters for expression level in stably transfected CHO K1 (A) and CHO DG44 (B) cells. Stably transfected pools were generated by transfection of CHO K1/CHO DG44 cells with monoclonal antibody (mAb) expressing vectors containing different chimeric promoters and selection of stable transfectants using zeocin. Antibody titers of stably transfected pools were determined in shake flask batch cultures. The black bar represents the titer from the strongest wild type promoter. Seven hybrid promoters exhibited higher recombinant protein production than any wild type promoters in CHO K1 cells. 21 hybrid promoters exhibit higher expression than any wild type promoters in CHO DG44 cells.
Figure 3:
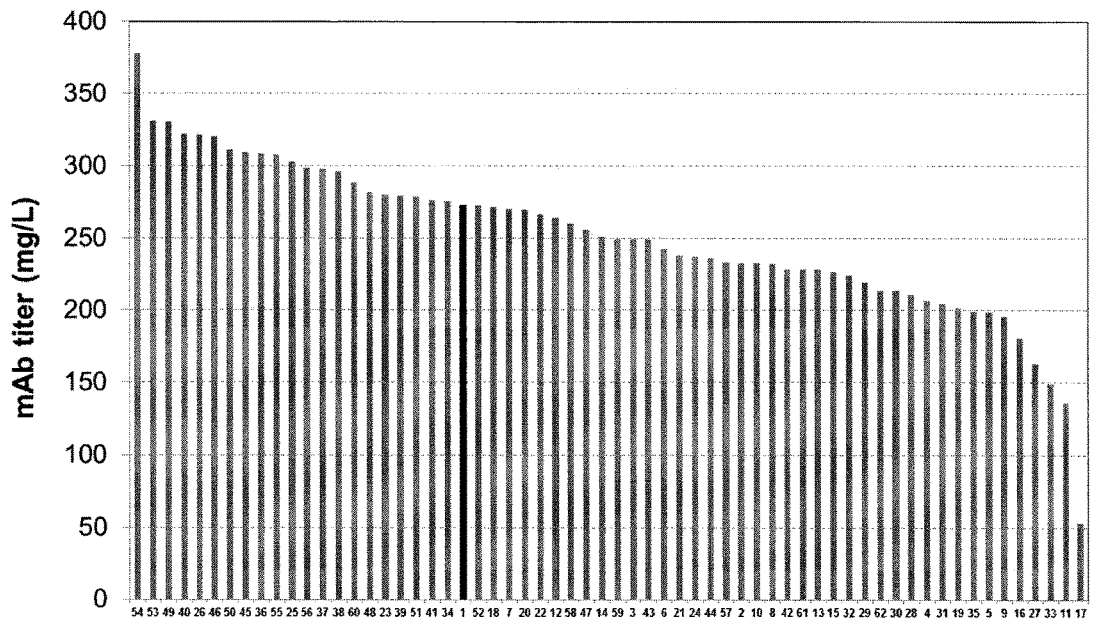

Stably transfected CHO K1 pools were generated by transfecting $1 \times 10^7$ CHO K1 cells with 5 µg of an appropriate linearized mAb expressing plasmid containing a specific chimeric promoter and zeocin selection marker gene (FIG. 2A). Transfections were carried out using NUCLEOFECTOR™ kit V (Lonza, VCA1003) and program U-24 on a NUCLEOFECTOR™ II electroporation system (Lonza, Cologne, Germany) following the manufacturer's instructions. The transfected cells were then resuspended in 2 mL protein free medium in 6-well suspension culture plate. At 24 h post-transfection, the transfected cell culture were centrifuged at ~100×g for 5 min. Cell pellets were then resuspended in 25 mL protein free medium containing 600 µg/mL zeocin in 125 mL shake flasks to select for stable transfectants. The stably transfected pools were deemed successfully generated when viability of stably transfected pools recovered above 95%. Productivity of each stably transfected pool was determined in 125 mL shake flask batch cultures. Cells were seeded at $2 \times 10^5$ cells/mL. Cell density and viability were monitored using Vi-Cell every day until viability dropped to below 50%. The supernatant was collected at the end of culture and analyzed for mAb concentration using a nephelometric method on an IMMAGE® 800 immunochemistry system (Beckman Coulter, Buckinghamshire, England). The IMMAGE® 800 immunohistochemistry system uses anti-human Fc region antibodies for IgG detection. The average titer of duplicated pools generated using each promoter was shown in FIG. 3A.

Transfection of CHO DG44 cells were carried out using the same protocol as for CHO K1 cells. The transfected cells were then resuspended in 2 mL protein free medium containing hypoxanthine and thymine (HT) in 6-well suspension culture plate. At 24 h post-transfection, the transfected cell culture were centrifuged at ~100×g for 5 min. Cell pellets were then resuspended in 25 mL protein free medium without HT in 125 mL shake flasks to select for stable transfectants. When viability of stably transfected pools recovered above 95%, stepwise methotrexate (MTX, Sigma, M8407) amplification was carried out with concentrations of 50 nM to 500 nM. Productivity of amplified pools at 500 nM was determined using the same protocol as for stably transfected CHO K1 cells. The average titer of duplicated pools generated using each promoter was shown in FIG. 3b.

What is claimed is:

1. An isolated nucleic acid molecule comprising a functional chimeric gene regulatory unit comprising:
   (a) a functional enhancer nucleotide sequence selected from the group consisting of a human cytomegalovirus, a murine cytomegalovirus, a simian virus 40, and a combination thereof; wherein the functional enhancer nucleotide sequence comprises SEQ ID NO:1; SEQ ID NO:2; SEQ ID NO:3, or a complement thereof;
   (b) a functional core promoter nucleotide sequence selected from the group consisting of a human cytomegalovirus, a murine cytomegalovirus, a simian virus 40, a human EF-1α gene, a chicken β-actin gene, and a combination thereof, wherein the functional core promoter nucleotide sequence comprises SEQ ID NO:4; SEQ ID NO:5; SEQ ID NO:6; SEQ ID NO:7; SEQ ID NO:8; or a complement thereof; and
   (c) at least one nucleotide sequence encoding for an intron selected from the group consisting of a human cytomegalovirus, human EF-1α gene, a chicken β-actin gene, and a combination thereof, wherein the intron nucleotide sequence comprises SEQ ID NO:9; SEQ ID NO:10; SEQ ID NO:11; or a complement thereof; wherein the enhancer nucleotide sequence is 5' to the promoter nucleotide sequence and the intron nucleotide sequence is 3' to the promoter sequence; and wherein the chimeric gene regulatory unit comprises a nucleotide sequence as set forth in SEQ ID Nos. 30, 34, 35, 36, 37, 45, 47-52, 56, 57, 59-62, 64-67, 71 or a complement thereof.

2. The isolated nucleic acid molecule of claim 1, further comprising at least one nucleotide sequence encoding for a polypeptide, peptide or RNA molecule, wherein said sequence said sequence is operably linked to the chimeric gene regulatory unit.

3. The isolated nucleic acid molecule of claim 2, wherein the at least one nucleotide sequence encoding for a polypeptide, peptide or RNA molecule of interest lies 3' to the intron nucleotide sequence.

4. The isolated nucleic acid molecule of claim 3, wherein the at least one nucleotide sequence encoding for a polypeptide, peptide or RNA molecule of interest lies directly adjacent to the intron sequence.

5. The isolated nucleic acid molecule of claim 2, wherein the polypeptide of interest is a polypeptide chain of a naturally occurring or artificial immunoglobulin.

6. The isolated nucleic acid molecule of claim 1, wherein the chimeric gene regulation unit has an increased resistance to transcriptional silencing.

7. The isolated nucleic acid molecule of claim 1, wherein the isolated nucleic acid molecule further comprises at least one nucleotide sequence encoding for a recognition site of a restriction endonuclease.

8. The isolated nucleic acid molecule of claim 7, wherein the at least one nucleotide sequence encoding for a recognition site of a restriction endonuclease is (i) 3' to the enhancer nucleotide sequence and 5' to the promoter nucleotide sequence or (ii) 3' to the promoter nucleotide sequence and 5' to the at least one nucleotide sequence encoding for an intron.

9. The isolated nucleic acid molecule of claim 1, wherein the isolated nucleic acid molecule of the invention comprising the functional chimeric gene regulatory unit and the at least one nucleotide sequence encoding for a polypeptide, peptide or RNA molecule of interest has increased expression activity to express the polypeptide, peptide or RNA molecule of interest in CHO (Chinese Hamster Ovary) K1 or CHO DG44 cells compared to an isolated nucleic acid molecule comprising a naturally occurring gene regulatory unit and a nucleotide sequence encoding for the same polypeptide, peptide or RNA molecule of interest.

10. The isolated nucleic acid molecule of claim 1, wherein the promoter comprises at least one binding site for a transcription factor.

11. A method of producing a polypeptide, peptide or RNA of interest comprising:
(i) providing an isolated nucleic acid molecule comprising a functional chimeric gene regulatory unit comprising:
(a) a functional enhancer nucleotide sequence selected from the group consisting of a human cytomegalovirus, a murine cytomegalovirus, a simian virus 40, and a combination thereof; wherein the functional enhancer nucleotide sequence comprises SEQ ID NO:1; SEQ ID NO:2; SEQ ID NO:3, or a complement thereof, (b) a functional core promoter nucleotide sequence selected from the group consisting of a human cytomegalovirus, a murine cytomegalovirus, a simian virus 40, a human EF-Ia gene, a chicken R-actin gene, and a combination thereof, wherein the functional core promoter nucleotide sequence comprises SEQ ID NO:4; SEQ ID NO:5; SEQ ID NO:6; SEQ ID NO:7; SEQ ID NO:8; or a complement thereof, and (c) at least one nucleotide sequence encoding for an intron selected from the group consisting of a human cytomegalovirus, a human EF-Ia gene, a chicken 3-actin gene, and a combination thereof, wherein the wherein the intron nucleotide sequence comprises SEQ ID NO:9; SEQ ID NO: 10; SEQ ID NO: 11; or a complement thereof, wherein the enhancer nucleotide sequence is 5' to the promoter nucleotide sequence and the intron nucleotide sequence is 3' to the promoter sequence; and wherein the chimeric gene regulatory unit comprises a nucleotide sequence as set forth in SEQ ID Nos. 30, 34, 35, 36, 37, 45, 47-52, 56, 57, 59-62, 64-67, 71 or a complement thereof said isolated nucleic acid molecule comprises a nucleotide sequence encoding the polypeptide, peptide or RNA of interest, said nucleotide sequence encoding the polypeptide, peptide or RNA of interest being operably linked to the chimeric gene regulatory unit of the isolated nucleic acid molecule; and (ii) producing the polypeptide, peptide or RNA of interest by in vitro transcription and translation or in a host cell under conditions that allow production of the polypeptide, peptide or RNA of interest.

12. An isolated recombinant host cell comprising an isolated nucleic acid molecule comprising a functional chimeric gene regulatory unit comprising:
(a) a functional enhancer nucleotide sequence selected from the group consisting of a human cytomegalovirus, a murine cytomegalovirus, a simian virus 40, a human EF-1α gene, a chicken β-actin gene, and a combination thereof; wherein the functional enhancer nucleotide sequence comprises SEQ ID NO:1; SEQ ID NO:2; SEQ ID NO:3, or a complement thereof;
(b) a functional core promoter nucleotide sequence selected from the group consisting of a human cytomegalovirus, a murine cytomegalovirus, a simian virus 40, a human EF-1α gene, a chicken β-actin gene, and a combination thereof, wherein the functional core promoter nucleotide sequence comprises SEQ ID NO:4; SEQ ID NO:5; SEQ ID NO:6; SEQ ID NO:7; SEQ ID NO:8; or a complement thereof; and
(c) at least one nucleotide sequence encoding for an intron selected from the group consisting of a human cytomegalovirus, a murine cytomegalovirus, a simian virus 40, a human EF-1α gene, a chicken β-actin gene, and a combination thereof, wherein the wherein the intron nucleotide sequence comprises SEQ ID NO:9; SEQ ID NO:10; SEQ ID NO:11; or a complement thereof, wherein the enhancer nucleotide sequence is 5' to the promoter nucleotide sequence and the intron nucleotide sequence is 3' to the promoter sequence; wherein the enhancer nucleotide sequence is from a different species than the functional core promoter nucleotide sequence and the at least one nucleotide sequence encoding for the intron; and wherein the chimeric gene regulatory unit comprises a nucleotide sequence as set forth in SEQ ID Nos. 30, 34, 35, 36, 37, 45, 47-52, 56, 57, 59-62, 64-67, 71 or a complement thereof.

* * * * *